United States Patent
Lan et al.

(10) Patent No.: US 11,124,830 B2
(45) Date of Patent: *Sep. 21, 2021

(54) SINGLE CELL GENOMIC SEQUENCING USING HYDROGEL BASED DROPLETS

(71) Applicant: The Regent of the University of California, Oakland, CA (US)

(72) Inventors: Freeman Lan, San Francisco, CA (US); Benjamin Demaree, Berkeley, CA (US); Iain Clark, San Francisco, CA (US); Adam R. Abate, Daly City, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/849,344

(22) Filed: Apr. 15, 2020

(65) Prior Publication Data

US 2020/0277672 A1    Sep. 3, 2020

Related U.S. Application Data

(63) Continuation of application No. 16/468,652, filed as application No. PCT/US2017/068006 on Dec. 21, 2017.

(60) Provisional application No. 62/437,605, filed on Dec. 21, 2016.

(51) Int. Cl.
*C12Q 1/6869* (2018.01)
*C12Q 1/6806* (2018.01)

(52) U.S. Cl.
CPC ......... *C12Q 1/6869* (2013.01); *C12Q 1/6806* (2013.01); *C12Q 2565/629* (2013.01); *C12Q 2600/156* (2013.01)

(58) Field of Classification Search
CPC ................ C12Q 1/6869; C12Q 1/6806; C12Q 2565/629; C12Q 2600/156
See application file for complete search history.

(56) References Cited

U.S. PATENT DOCUMENTS

| | | | |
|---|---|---|---|
| 7,638,276 B2 | 12/2009 | Griffiths et al. | |
| RE41,780 E | 9/2010 | Anderson et al. | |
| 8,067,159 B2 | 11/2011 | Brown et al. | |
| 8,257,925 B2 | 9/2012 | Brown et al. | |
| 8,765,485 B2 | 7/2014 | Link et al. | |
| 9,150,852 B2 | 10/2015 | Samuels et al. | |
| 10,161,007 B2 | 12/2018 | Abate et al. | |
| 10,745,762 B2 | 8/2020 | Abate et al. | |
| 2002/0086042 A1 | 7/2002 | Delrieu et al. | |
| 2003/0156993 A1 | 8/2003 | Staats | |
| 2003/0180737 A1 | 9/2003 | Gu et al. | |
| 2005/0019902 A1 | 1/2005 | Mathies et al. | |
| 2005/0112639 A1 | 5/2005 | Wang et al. | |
| 2005/0172476 A1 | 8/2005 | Stone et al. | |
| 2007/0039866 A1 | 2/2007 | Schroeder et al. | |
| 2007/0077572 A1 | 4/2007 | Tawfik et al. | |
| 2007/0141593 A1 | 6/2007 | Lee et al. | |
| 2007/0231880 A1 | 10/2007 | Chang-yen et al. | |
| 2008/0014589 A1 | 1/2008 | Link et al. | |
| 2009/0045064 A1 | 2/2009 | Simmons et al. | |
| 2009/0098555 A1 | 4/2009 | Roth et al. | |
| 2010/0015614 A1 | 1/2010 | Beer et al. | |
| 2010/0028915 A1 | 2/2010 | Gualberto et al. | |
| 2010/0055677 A1 | 3/2010 | Colston, Jr. et al. | |
| 2010/0137163 A1 | 6/2010 | Link et al. | |
| 2010/0173394 A1 | 7/2010 | Colston, Jr. et al. | |
| 2010/0285975 A1 | 11/2010 | Mathies et al. | |
| 2011/0053798 A1 | 3/2011 | Hindson et al. | |
| 2011/0056575 A1 | 3/2011 | Hong et al. | |
| 2011/0059556 A1 | 3/2011 | Strey et al. | |
| 2011/0086352 A1 | 4/2011 | Bashir et al. | |
| 2011/0103176 A1 | 5/2011 | Van Dam et al. | |
| 2011/0104816 A1 | 5/2011 | Pollack et al. | |
| 2011/0118151 A1 | 5/2011 | Eshoo et al. | |
| 2011/0160078 A1 | 6/2011 | Fodor et al. | |
| 2011/0217736 A1 | 9/2011 | Hindson | |
| 2011/0311978 A1 | 12/2011 | Makarewicz, Jr. et al. | |
| 2012/0010086 A1 | 1/2012 | Froehlich et al. | |
| 2012/0045765 A1 | 2/2012 | Curran et al. | |
| 2012/0122714 A1 | 5/2012 | Samuels et al. | |
| 2012/0132288 A1 | 5/2012 | Weitz et al. | |
| 2012/0190032 A1 | 7/2012 | Ness et al. | |
| 2012/0190033 A1 | 7/2012 | Ness et al. | |
| 2012/0196288 A1 | 8/2012 | Beer | |

(Continued)

FOREIGN PATENT DOCUMENTS

| AU | 2013203624 A1 | 5/2013 |
|---|---|---|
| AU | 2013302867 A1 | 2/2015 |

(Continued)

OTHER PUBLICATIONS

Le Goff et al. Hydrogel microparticles for biosensing. European Polymer Journal 2015; 72: 386-412 (Year: 2015).*
Caruccio, N. Preparation of Next-Generation Sequencing Libraries Using Nextera™ Technology: Simultaneous DNA Fragmentation and Adaptor Tagging by In Vitro Transposition Methods in Molecular Biology 2011; 733: 241-255 (Year: 2011).*
Novak et al. Single-Cell Multiplex Gene Detection and Sequencing with Microfluidically Generated Agarose Emulsions. Angewandte Chemie International Edition 2011; 50: 390-395 (Year: 2011).*
Spencer et al. The ISME Journal 2016; 10: 427-436 (Year: 2016).*
Extended European Search Report received for European Patent Application Serial No. 13829925.0 dated Feb. 8, 2016, 7 pages.

(Continued)

Primary Examiner — Angela M. Bertagna
(74) Attorney, Agent, or Firm — Edward J. Baba; Bozicevic, Field & Francis LLP

(57) ABSTRACT

The present disclosure provides ultrahigh-throughput single cell genomic sequencing methods, referred to herein as "SiC-seq", which methods include encapsulating single cells in molten gel droplets to facilitate bulk cell lysis and purification of genomic DNA in microgels. Systems and devices for practicing the subject methods are also provided.

15 Claims, 39 Drawing Sheets

Specification includes a Sequence Listing.

(56) References Cited

U.S. PATENT DOCUMENTS

| | | |
|---|---|---|
| 2012/0219947 A1 | 8/2012 | Yurkovetsky et al. |
| 2012/0220494 A1 | 8/2012 | Samuels et al. |
| 2012/0258870 A1 | 10/2012 | Schwartz et al. |
| 2012/0264646 A1 | 10/2012 | Link et al. |
| 2012/0270739 A1 | 10/2012 | Rava et al. |
| 2012/0309002 A1 | 12/2012 | Link |
| 2012/0316074 A1 | 12/2012 | Saxonov |
| 2013/0032235 A1 | 2/2013 | Johnstone et al. |
| 2013/0046030 A1 | 2/2013 | Rotem et al. |
| 2013/0084572 A1 | 4/2013 | Hindson et al. |
| 2013/0095469 A1 | 4/2013 | Koltay et al. |
| 2013/0116130 A1 | 5/2013 | Fu et al. |
| 2013/0130919 A1 | 5/2013 | Chen et al. |
| 2013/0189700 A1 | 7/2013 | So et al. |
| 2013/0203605 A1 | 8/2013 | Shendure et al. |
| 2013/0210639 A1 | 8/2013 | Link et al. |
| 2013/0236901 A1 | 9/2013 | Potier et al. |
| 2013/0295567 A1 | 11/2013 | Link et al. |
| 2013/0295587 A1 | 11/2013 | Sjobom |
| 2014/0057799 A1 | 2/2014 | Johnson et al. |
| 2014/0154695 A1 | 6/2014 | Miller et al. |
| 2014/0155295 A1 | 6/2014 | Hindson et al. |
| 2014/0179544 A1 | 6/2014 | Steenblock et al. |
| 2014/0199731 A1 | 7/2014 | Agresti et al. |
| 2014/0272988 A1 | 9/2014 | Zador et al. |
| 2014/0323316 A1 | 10/2014 | Drmanac et al. |
| 2014/0378345 A1 | 12/2014 | Hindson et al. |
| 2014/0378349 A1 | 12/2014 | Hindson et al. |
| 2015/0232942 A1 | 8/2015 | Abate et al. |
| 2015/0298091 A1 | 10/2015 | Weitz et al. |
| 2016/0177375 A1 | 6/2016 | Abate et al. |
| 2016/0265043 A1 | 9/2016 | Geng et al. |
| 2017/0009274 A1 | 1/2017 | Abate et al. |
| 2017/0022538 A1 | 1/2017 | Abate et al. |
| 2017/0121756 A1 | 5/2017 | Abate et al. |
| 2018/0056288 A1 | 3/2018 | Abate et al. |
| 2018/0216160 A1 | 8/2018 | Abate et al. |
| 2018/0237836 A1 | 8/2018 | Abate et al. |
| 2019/0127789 A1* | 5/2019 | Weitz .................. C12Q 1/6855 |
| 2019/0169700 A1 | 6/2019 | Abate et al. |
| 2019/0218594 A1 | 7/2019 | Abate et al. |
| 2019/0241965 A1 | 8/2019 | Abate et al. |
| 2019/0330701 A1 | 10/2019 | Abate et al. |

FOREIGN PATENT DOCUMENTS

| | | |
|---|---|---|
| AU | 2016215298 A1 | 8/2017 |
| AU | 2016215304 A1 | 8/2017 |
| AU | 2017382905 A1 | 7/2019 |
| AU | 2019226236 A1 | 9/2019 |
| CA | 2881783 A1 | 2/2014 |
| CA | 3001986 A1 | 4/2016 |
| CA | 2974299 A1 | 8/2016 |
| CA | 2974306 A1 | 8/2016 |
| CA | 3047328 A1 | 6/2018 |
| CN | 1693478 A | 11/2005 |
| CN | 104736725 A | 6/2015 |
| CN | 107107058 A | 8/2017 |
| CN | 107429426 A | 12/2017 |
| CN | 107530654 A | 1/2018 |
| CN | 108350488 A | 7/2018 |
| CN | 110088290 A | 8/2019 |
| CN | 110462053 A | 11/2019 |
| DE | 10339452 A1 | 3/2005 |
| EP | 1547677 A1 | 6/2005 |
| EP | 2145955 B1 | 2/2012 |
| EP | 2565650 A1 | 3/2013 |
| EP | 2882872 A2 | 6/2015 |
| EP | 3160654 A2 | 5/2017 |
| EP | 3209419 A1 | 8/2017 |
| EP | 3253479 A2 | 12/2017 |
| EP | 3253910 A1 | 12/2017 |
| EP | 3337907 A1 | 6/2018 |
| GB | 2519906 A | 5/2015 |
| GB | 2539836 A | 12/2016 |
| JP | 2013503630 A | 2/2013 |
| JP | 2014521334 A | 8/2014 |
| JP | 2015533079 A | 11/2015 |
| JP | 2018505671 A | 3/2018 |
| JP | 2018508198 A | 3/2018 |
| JP | 2018525004 A | 9/2018 |
| WO | 9412216 A1 | 6/1994 |
| WO | 2007140015 A2 | 12/2007 |
| WO | 2009050512 A2 | 4/2009 |
| WO | 2009054870 A2 | 4/2009 |
| WO | 2009111014 A2 | 9/2009 |
| WO | 2010148039 A2 | 12/2010 |
| WO | 2011047307 A1 | 4/2011 |
| WO | 2012011091 A2 | 1/2012 |
| WO | 2012048341 A1 | 4/2012 |
| WO | 2012083225 A2 | 6/2012 |
| WO | 2012109600 A2 | 8/2012 |
| WO | 2012142213 A2 | 10/2012 |
| WO | 2012162267 A2 | 11/2012 |
| WO | WO2013015793 A1 | 1/2013 |
| WO | 2013095469 A2 | 6/2013 |
| WO | 2013119753 A1 | 8/2013 |
| WO | 2013126741 A1 | 8/2013 |
| WO | 2013130512 A2 | 9/2013 |
| WO | 2013134261 A1 | 9/2013 |
| WO | 2013173394 A2 | 11/2013 |
| WO | 2014028378 A2 | 2/2014 |
| WO | 2014028537 A1 | 2/2014 |
| WO | 2014047556 A1 | 3/2014 |
| WO | 2014083435 A2 | 6/2014 |
| WO | 2014093676 A1 | 6/2014 |
| WO | 2014108323 A1 | 7/2014 |
| WO | 2014138132 A2 | 9/2014 |
| WO | 2014151658 A1 | 9/2014 |
| WO | 2014153071 A1 | 9/2014 |
| WO | 2015031691 A1 | 3/2015 |
| WO | 2015069798 A1 | 5/2015 |
| WO | 2015120398 A1 | 8/2015 |
| WO | 2015157369 A1 | 10/2015 |
| WO | WO2015179848 A1 | 11/2015 |
| WO | 2015189336 A1 | 12/2015 |
| WO | 2015200717 A2 | 12/2015 |
| WO | 2016064755 A2 | 4/2016 |
| WO | 2016065056 A1 | 4/2016 |
| WO | 2016126865 A1 | 8/2016 |
| WO | 2016126871 A2 | 8/2016 |
| WO | WO2017031125 A1 | 2/2017 |
| WO | WO2018031691 A1 | 2/2018 |
| WO | WO2018119301 A1 | 6/2018 |
| WO | WO2019099908 A1 | 5/2019 |

OTHER PUBLICATIONS

Extended European Search Report received for European Patent Application Serial No. 15812857.9 dated Oct. 17, 2017, 7 pages.

Extended European Search Report received for European Patent Application Serial No. 15853268.9 dated Sep. 3, 2018, 12 pages.

Extended European Search Report received for European Patent Application Serial No. 16747224.0 dated May 24, 2018, 9 pages.

Extended European Search Report received for European Patent Application Serial No. 16747229.9 dated Sep. 10, 2019, 8 pages.

Extended European Search Report received for European Patent Application Serial No. 16837703.4 dated Nov. 29, 2018, 9 pages.

First search received for Chinese Patent Application Serial No. 2013800532581 dated Feb. 22, 2016, 2 pages.

First search received for Chinese Patent Application Serial No. 2015800704110 dated Dec. 13, 2018, 2 pages.

International Preliminary Report on Patentability received for PCT Application Serial No. PCT/US2013/054517 dated Feb. 26, 2015, 14 pages.

International Preliminary Report on Patentability received for PCT Application Serial No. PCT/US2015/037822 dated Jan. 5, 2017, 7 pages.

International Preliminary Report on Patentability received for PCT Application Serial No. PCT/US2015/056743 dated May 4, 2017, 9 pages.

(56) References Cited

OTHER PUBLICATIONS

International Preliminary Report on Patentability received for PCT Application Serial No. PCT/US2016/016438 dated Aug. 17, 2017, 10 pages.
International Preliminary Report on Patentability received for PCT Application Serial No. PCT/US2016/016444 dated Aug. 17, 2017, 40 pages.
International Preliminary Report on Patentability received for PCT Application Serial No. PCT/US2016/047199 dated Mar. 1, 2018, 8 pages.
International Preliminary Report on Patentability received for PCT Application Serial No. PCT/US2017/046159 dated Feb. 21, 2019, 9 pages.
International Preliminary Report on Patentability received for PCT Application Serial No. PCT/US2017/068006 dated Jul. 4, 2019, 7 pages.
International Preliminary Report on Patentability received for PCT Application Serial No. PCT/US2017/68006 dated Jul. 4, 2019, 7 pages.
International Search Report and Written Opinion received for PCT Application Serial No. PCT/US2013/054517 dated Feb. 21, 2014, 19 pages.
International Search Report and Written Opinion received for PCT Application Serial No. PCT/US2015/037822 dated Feb. 2, 2016, 9 pages.
International Search Report and Written Opinion received for PCT Application Serial No. PCT/US2015/056743 dated Mar. 3, 2016, 12 pages.
International Search Report and Written Opinion received for PCT Application Serial No. PCT/US2016/016438 dated Jun. 10, 2016, 14 pages.
International Search Report and Written Opinion received for PCT Application Serial No. PCT/US2016/016444 dated Jul. 27, 2016, 43 pages.
International Search Report and Written Opinion received for PCT Application Serial No. PCT/US2016/047199 dated Dec. 12, 2016, 10 pages.
International Search Report and Written Opinion received for PCT Application Serial No. PCT/US2017/046159 dated Nov. 21, 2017, 12 pages.
International Search Report and Written Opinion received for PCT Application Serial No. PCT/US2017/068006 dated Mar. 26, 2018, 9 pages.
Abate, Adam R, et al., "Efficient encapsulation with plug-triggered drop formation", vol. 84(3), Phys Rev E Stat Nonlin Soft Matter Phys., Sep. 22, 2011, 031502.
Abate, Adam R, et al., "Faster multiple emulsification with drop splitting", vol. 11(11), Lab Chip, Jun. 7, 2011, 1911-1915.
Abate, Adam R, et al., "High-throughput injection with microfluidics using picoinjectors", PNAS vol. 107(45), Nov. 9, 2010, 19163-19166.
Abate, Adam R, et al., "Microfluidic sorting with high-speed single-layer membrane valves", Applied Physics Letters 96, 2010, 03509-1-203509-3.
Abate, Adam R, et al., "One-step formation of multiple emulsions in microfluidics", vol. 11(2) Lab on a Chip, Oct. 2010, 253-258.
Agresti, Jeremy J, et al., "Ultrahigh-throughput screening in drop-based microfluidics for directed evolution", See Corrected Version—Proc Natl Acad Sci USA, 107, 2010, 4004-4009.
Agresti, Jeremy J, et al., "Ultrahigh-throughput screening in drop-based microftuidics for directed evolution", Corrected Version—Proc Natl Acad Sci USA, 107(14), 2010, 6550-6551.
Ahn, Keunho, et al., "Electrocoalescence of drops synchronized by size-dependent flow in microfluidic channels", vol. 88, Applied Physics Letters, 264105-1-264105-3.
Ali, M Monsur, et al., "Rolling circle amplification: a versatile tool for chemical biology, materials science and medicine", vol. 43(10), Chem Soc Rev., Mar. 18, 2014, 3324-3341.
Allen, Lisa Z, et al., "Single virus genomics: a new tool for virus discovery", PLoS One vol. 6(3), Mar. 23, 2011, e17722.

Arriaga, Laura R, et al., "Ultrathin Shell Double Emulsion Templated Giant Unilamellar Lipid Vesicles with Controlled Microdomain Formation", vol. 10(5), Mar. 12, 2014, 950-956.
Atten, P, "Electrocoalescence of Water Droplets in an Insulating Liquid", vol. 30, 259-269.
Barenholz, Y, et al., "A simple method for the preparation of homogeneous phospholipid vesicles", Biochemistry 16(12), 2806-2810.
Baret, Jean C, et al., "Fluorescence-activated droplet sorting (FADS): efficient microfluidic cell sorting based on enzymatic activity", vol. 9(13), Lab on a Chip, Apr. 23, 2009, 1850-1858.
Battaglia, Giuseppe, et al., "Polymeric vesicle permeability: a facile chemical assay", vol. 22(11), Langmuir, 4910-4913.
Beer, NR, et al., "On-chip single-copy real-time reverse-transcription PCR in isolated picoliter droplets", Anal Chem., vol. 80(6), 1854-1858.
Bernath, K, et al., "In vitro compartmentalization by double emulsions: sorting and gene enrichment by fluorescence activated cell sorting", vol. 325(1), Analytical Biochemistry, 151-157.
Bird, R E, et al., "Single-chain antigen-binding proteins" <!Citation**> , Oct. 21, 1988, 423-426.
Blainey, Paul C, "The future is now: single-cell genomics of bacteria and archaea", FEMS microbiology reviews 37(3), May 2013, 407- 427.
Brouzes, E, et al., "Droplet microfluidic technology for single-cell high-throughput screening", vol. 106(34), Proc Natl Acad Sci U S A., 14195-14200.
Brown, Robert B, et al., "Current techniques for single-cell lysis", J R Soc Interface, 5 Suppl 2, Oct. 6, 2008, S131-S138.
Caron, G. Nebe-Von, et al., "Assessment of bacterial viability status by flow cytometry and single cell sorting", vol. 84(6), Journal of Applied Microbiology, Jul. 17, 1997, 988-998.
Chabert, M, et al., "Droplet fusion by alternating current (AC) field electrocoalescence in microchannels", Electrophoresis vol. 26(19), 3706-3715.
Chaffer, Christine L, et al., "A Perspective on Cancer Cell Metastasis", Science vol. 331(6024), Mar. 25, 2011, 1559-1564.
Chen, Chin-Ming, et al., "Influence of pH on the stability of oil-in-water emulsions stabilized by a splittable surfactant", Colloids and Surfaces A: Physicochemical and Engineering Aspects, vol. 170 (2-3), 173-179.
Teh, Shia-Yen, et al., "Droplet microfluidics", Lab on a chip, vol. 8, Issue 2, Jan. 11, 2008, 198-220.
Extended European Search Report received for European Patent Application Serial No. 17885180.4 dated Jul. 20, 2020, 11 pages.
Extended European Search Report received for European Patent Application Serial No. 17840230.1 dated Apr. 30, 2020, 12 pages.
Demaree, Benjamin, et al., "An Ultrahigh-throughput Microfluidic Platform for Single-cell Genome Sequencing", Journal of Visualized Experiments 135 (e57598), 2018, 1-13.
Gong, Jian, et al., "Characterization and Design of Digitizing Processes for Uniform and Controllable Droplet Volume in EWOD Digital Microfluidics", Solid-State Sensors, Actuators, and Microsystems Workshop, 2006, 159-162.
Ichii, Tetsuo, et al., "Amplification of RNA in Growing and Dividing Micro-Droplets", 14th International Conf on Miniaturized Systems for Chemistry and Life Sciences, 2010, 2089-2091.
Kumaresan, Palani, et al., "High-Throughput Single Copy DNA Amplification and Cell Analysis in Engineered Nanoliter Droplets", Anal. Chem. 80, 2008, 3522-3529.
Lan, Freeman, et al., "Single-cell genome sequencing at ultra-high-throughput with microfluidic droplet barcoding", Nature Biotechnology 35(7), 2017, 640-646.
Lim, Shaun W., et al., "Ultrahigh-throughput sorting of microfluidic drops with flow cytometry", Lab Chip, 2013, vol. 13, pp. 4563-4572.
Pekin, Deniz, et al., "Quantitative and sensitive detection of rare mutations using droplet-based microfluidics", Lab Chip 11, 2011, 2156-2166.
Rakszewska, Agata, et al., "One drop at a time: toward droplet microfluidics as a versatile tool for single-cell analysis", NPG Asia Materials 6(10), 2014, 1-11.

(56) References Cited

OTHER PUBLICATIONS

Shembekar, Nachiket, et al., "Droplet-based microfluidics in drug discovery, transcriptomics and high-throughput molecular genetics", Lab on a Chip 16(8), 2016, 1314-1331.

Abate, Adam R., et al., (2008) "Photoreactive coating for high-contrast spatial patterning of microfluidic device wettability", vol. 8(12), Lab on a Chip, pp. 2157-2160.

Chung, Changkwon, et al., (2010) "Droplet dynamics passing through obstructions in confined microchannel flow" Microfluidics and Nanofluidics, vol. 9(6), pp. 1151-1163.

Clausell-Tormos, J., et al., (2008) "Droplet-based microfluidic platforms for the encapsulation and screening of Mammalian cells and multicellular organisms" Chemistry and Biology, vol. 15(5), pp. 427-437.

Dejournette, Cheryl J., et al., (2013) "Creating Biocompatible Oil-Water Interfaces without Synthesis: Direct Interactions between Primary Amines and Carboxylated Perfluorocarbon Surfactants", Analytical chemistry, vol. 85 (21), pp. 10556-10564.

Dietrich, G J., et al., (2005) "Effects of UV irradiation and hydrogen peroxide on DNA fragmentation, motility and fertilizing ability of rainbow trout (*Oncorhynchus mykiss*) spermatozoa", Theriogenology vol. 64(8), pp. 1809-1822.

Duffy, David C., et al., (1998) "Rapid Prototyping of Microfluidic Systems in Poly (dimethylsiloxane)", Anal. Chem., vol. 70(23), pp. 4974-4984.

Eastburn, Dennis J., et al., (2013) "Picoinjection enables digital detection of RNA with droplet rt-PCR" PLoS One vol. 8(4), p. e62961.

Eastburn, Dennis J., et al., (2013) "Ultrahigh-Throughput Mammalian Single-Cell Reverse-Transcriptase Polymerase Chain Reaction in Microfluidic Drops", Anal. Chem. 85 (16), pp. 8016-8021.

Edd, Jon F., et al., (2008) "Controlled encapsulation of single-cells into monodisperse picolitre drops", Lab Chip, vol. 8(8), pp. 1262-1264.

Frenz, Lucas, et al., (2009) "Reliable microfluidic on-chip incubation of droplets in delay-lines", Lab on a Chip vol. 9(10), pp. 1344-1348.

Fu, Yusi, et al., (2015) "Uniform and accurate single-cell sequencing based on emulsion whole-genome amplification" Proc. Nall. Acad. Sci. USA, vol. 112(38), pp. 11923-11928.

Garstecki, Piotr, et al., (2006) "Formation of droplets and bubbles in a microfluidic T-junction-scaling and mechanism of break-up", Lab on a Chip, vol. 6(3), pp. 437-446.

Gevensleben, Heidrun, et al., (2013) "Non-invasive Detection of HER2 Amplification with Plasma DNA Digital PCR", Clinical Cancer Research, vol. 19(12), pp. 3276-3284.

Gribskov, M, et al., (1986) "Sigma factors from *E. coil, B. subtilis*, phage SP01, and phage T4 are homologous proteins", Nucleic Acids Res., vol. 14(16), pp. 6745-6763.

Grover, Alka, et al., (2009) Multiple displacement amplification as a pre-polymerase chain reaction (pre-PCR) to detect ultra low population of Ralstonia solanacearum (Smith 1896) Yabuchi et al. (1996), Letters in Applied Microbiology, vol. 49(5), pp. 539-543.

Hayward, Ryan C., et al., (2006) "Dewetting instability during the formation of polymersomes from block-copolymer-stabilized double emulsions", Langmuir, vol. 22(10), pp. 457-4461.

Herminghaus, S, (1999) "Dynamical Instability of Thin Liquid Films Between Conducting Media", Physical Review Letter, vol. 83(12), pp. 2359-2361.

Hindson, et al., (2011) "High-throughput droplet digital PCR system for Absolute Quatitation of DNA copy number", Analytical chemistry, 83(22), pp. 8604-8610.

Holland, P M., et al., (1991) "Detection of specific polymerase chain reaction product by utilizing the 5'----3' exonuclease activity of Thermus aquaticus DNA polymerase" Proc Natl Acad Sci USA, 88 (16), pp. 7276-7280.

Holtze, C, et al., (2008) "Biocompatible surfactants for water-in-fluorocarbon emulsions", Lab Chip 8(10), pp. 1632-1639.

Horton, Robert M., et al., (2013) "Gene splicing by overlap extension: tailor-made genes using the polymerase chain reaction", Biotechniques, vol. 54, pp. 129-133.

Hu, Hoa, et al., (2009) "Mutation screening in 86 known X-linked mental retardation genes by droplet-based multiplex PCR and massive parallel sequencing" Hugo J., vol. 3 (1-4), pp. 41-49.

Huebner, Ansgar, et al., (2008) "Microdroplets: A sea of applications?" Lab on a Chip, vol. 8(8), pp. 1244-1254.

Hunkapiller, Tim, et al., (1986) "Immunology: The growing immunoglobulin gene superfamily", Nature vol. 323, pp. 15-16.

Hunt, Josephine A., et al., (1994) "Effect of pH on the stability and surface composition of emulsions made with whey protein isolate", Journal of Agricultural and Food Chemistry, vol. 42(10), pp. 2131-2135.

Huston, J S., et al., (1988) "Protein engineering of antibody binding sites: recovery of specific activity in an anti-digoxin single-chain Fv analogue produced in *Escherichia coli*" Proc. Natl. Acad. Sci. U.S.A. vol. 85(16), pp. 5879-5883.

Kawasaki, Ernest S., (1990) "Sample Preparation From Blood, Cells, and Other Fluids",Chapter 18 of PCR Protocols: A guide to methods and Applications, pp. 146-152.

Ki, Jang-Seu, et al., (2004) "Integrated Method for Single-Cell DNA Extraction, PCR Amplification, and Sequencing of Ribosomal DNA from Harmful Dinoflagellates Cochlodinium polykrikoides and Alexandrium catenella", Marine Biotechnology, vol. 6, pp. 587-593.

Kiss, Margaret M., et al., (2008) "High-Throughput Quantitative Polymerase Chain Reaction in Picoliter Droplets" Anal Chem, vol. 80(23), pp. 8975-8981.

Kritikou, Ekat, (2005) "It's cheaper in the Picolab", Nat Rev Genet, vol. 6, p. 668.

Küster, Simon K., et al., (2013) "Interfacing Droplet Microfluidics with Matrix-Assisted Laser Desorption/Ionization Mass Spectrometry: Label-Free Content Analysis of Single Droplets", Anal Chem, vol. 85(3), pp. 1285-1289.

Lagally, E T., et al., (2001) "Single-Molecule DNA Amplification and Analysis in an Integrated Microfluidic Device" Analytical Chemistry, vol. 73(3), pp. 565-570.

Lanzavecchia, Antonio, et al., (1987) "The use of hybrid hybridomas to target human cytotoxic T lymphocytes", Eur. J. Immunology, vol. 17(1), pp. 105-111.

Leary, James F., (1994) "Strategies for rare cell detection and isolation" Methods Cell Biol., vol. 42, pp. 331-358.

Lim, Shaun W., et al., (2013) "Ultrahigh-throughput sorting of microfluidic drops with flow cytometry", Lab on a Chip, vol. 13, pp. 4563-4572.

Link, D R., et al., (2004) "Geometrically mediated breakup of drops in microfluidic devices", Phys. Rev. Lett., vol. 92(5), p. 054503.

Livak, K J., et al., (2001) "Analysis of Relative Gene Expression Data Using Real-Time Quantitative PCR and the 2(-Delta Delta C(T)) Method" Methods, vol. 25(4), pp. 402-408.

Longo, M C., et al., (1990) "Use of uracil DNA glycosylase to control carry-over contamination in polymerase chain reactions" Gene, vol. 93(1), pp. 125-128.

Malloggi, Florent, et al., (2007) "Electrowetting-controlled droplet generation in a microfluidic flow-focusing device", Journal of Physics Condensed Matter, vol. 19(46), 462101, pp. 1-7.

Marcus, Joshua S., et al., (2006) "Parallel Picoliter rt-PCR Assays Using Microfluidics", Analytical Chemistry, vol. 78(3), pp. 956-958.

Markou, Athina, et al., (2011) "Molecular Characterization of Circulating Tumor Cells in Breast Cancer by a Liquid Bead Array Hybridization Assay" Clinical Chemistry vol. 57(3), pp. 421-430.

Mary, Pascaline, et al., (2011) "Controlling droplet incubation using close-packed plug flow", Biomicrofluidics, vol. 5(2), p. 24101.

Mazutis, Linas, et al., (2013) "Single-cell analysis and sorting using droplet-based microfluidics", Nature protocols, vol. 8(5), pp. 870-891.

McDonald, J C., et al., (2000) "Fabrication of microfluidic systems in poly(dimethylsiloxane)", Electrophoresis, vol. 21(1), pp. 27-40.

Metzker, Michael L., (2010) "Sequencing technologies—the next generation" Nature Reviews Genetics, vol. 11, pp. 31-46.

(56) References Cited

OTHER PUBLICATIONS

Miyazaki, Kentaro, (2020) "Random DNA fragmentation with endonuclease V: application to DNA shuffling" vol. 30(24), p. 139.
Miyazaki, Ryo, et al., (2013) "A new large-DNA-fragment delivery system based on integrase activity from an integrative and conjugative element", Appl Environ Microbiol vol. 79(14), pp. 4440-4447.
Moon, Sangjun, et al., (2011) "Drop-on-Demand Single Cell Isolation and Total RNA Analysis", vol. 6 Issue 3, pp. 1-10.
Morton, Keith J., et al., (2008) "Crossing microfluidic streamlines to lyse, label and wash cells", Lab Chip vol. 8(9), pp. 1448-1453.
Mui, B. L., et al., (1993) "Osmotic properties oflarge unilamellar vesicles prepared by extrusion", vol. 64(2), pp. 443-453.
Nagrath, Sunitha, et al., (2007) "Isolation of rare circulating tumour cells in cancer patients by microchip technology", Nature, vol. 450, pp. 1235-1239.
Nakano, Michihiko, et al., (2005) "Single-molecule reverse transcription polymerase chain reaction using water-in-oil emulsion", vol. 99(3), pp. 293-295.
Nikolova, Albena N., et al., (1996) "Effect of grafted PEG-2000 on the size and permeability of vesicles", vol. 1304(2), pp. 120-128.
Nishikawa, Yohei, et al., (2015) "Monodisperse Picoliter Droplets for Low-Bias and Contamination-Free Reactions in Single-Cell Whole Genome Amplification", PLoS One vol. 10(9), e0138733.
Novak, Richard, et al., (2011) "Single-cell multiplex gene detection and sequencing with microfluidically generated agarose emulsions", Angew Chem Int Ed Engl., vol. 50(2), pp. 390-395.
Nunes, J K., et al., (2013) "Dripping and jetting in microfluidic multiphase flows applied to particle and fibre synthesis", Journal of Physics D: Applied Physics, vol. 46(11).
O'Donovan, Brian, et al., (2012) "Electrode-free picoinjection of microfluidic drops", Lab on a chip, vol. 12, pp. 4029-4032.
Oberholzer, Thomas, et al., (1995) "Polymerase chain reaction in liposomes", vol. 2(10), pp. 677-682.
Okochi, Mina, et al., (2010) "Droplet-based gene expression analysis using a device with magnetic force-based-droplet-handling system", Journal of Bioscience and Bioengineering, vol. 109(2), pp. 193-197.
Perry, David J., (1999) "Solid-Phase Sequencing of Biotinylated PCR Products with Streptavidin-Coated Magnetic Beads", Hemostasis and Thrombosis Protocols, vol. 31, pp. 49-54.
Piatek, Amy S., et al., (1998) "Molecular beacon sequence analysis for detecting drug resistance in *Mycobacterium* tuberculosis" Nature Biotechnology, vol. 16(4), pp. 359-363.
Priest, Craig, et al., (2006) "Controlled electrocoalescence in microfluidics: Targeting a single lamella", Appl Phys Lett, vol. 89, pp. 134101-1-134101-3.
Roche, (2011) "emPCR Amplification Method Manual—Lib L LV for GS FLX+ Series-XL+", 454 Sequencing, Life Science Corp., pp. 1-12.
Rolando, Monica, et al., (2013) "Legionella pneumophila Effector RomA Uniquely Modifies Host Chromatin to Repress Gene Expression and Promote Intracellular Bacterial Replication", Cell Host & Microbe, vol. 13(4), pp. 395-405.
Sciambi, Adam, et al., (2013) "Adding reagent to droplets with controlled rupture of encapsulated double emulsions", Biomicrofluidics, vol. 7(4), pp. 044112-1-044112-6.
Sciambia, Adam, et al., (2015) "Accurate microfluidic sorting of droplets at 30 kHz", Lab Chip, vol. 15(1), 47-51.
Seemann, Ralf, et al., (2011) "Droplet based microfluidics", IOP Science, vol. 75, 016601.
Shui, Lingling, et al., (2011), "Microfluidic DNA fragmentation for on-chip genomic analysis", Nanotechnology, vol. 22(49), 494013.
Sidore, Angus M., et al., (2016) "Enhanced sequencing coverage with digital droplet multiple displacement amplification", Nucleic Acids Res., vol. 44(7), e66.
Siegel, Adam, et al., (2007), "Microsolidics: Fabrication of Three-Dimensional Metallic Microstructures in Poly (dimethylsiloxane)", Advanced Materials, vol. 19(5), pp. 727-733.

Song, Helen, et al., (2006) "Reactions in droplets in microfluidic channels", Angew Chem Int Ed Engl, vol. 45(44), pp. 7336-7356.
Squires, Tom M., et al., (2005) "Microfluidics: Fluid physics at the nanoliter scale", Reviews of modern physics, vol. 77(3), pp. 977-1026.
Stone, H. A., et al., (2004) "Engineering flows in small devices: microfluidics toward a lab-on-achip", vol. 36, pp. 381-411.
Scott, Shannon L., et al., (2010) "Isolation of circulating tumor cells using a microvortex-generating herringbone-chip", Proc Natl Acad Sci USA, vol. 107(43), pp. 18392-18397.
Syed, F, et al., (2009) "Next-generation sequencing library preparation: simultaneous fragmentation and tagging using in vitro transposition", vol. 6, pp. 1-2.
Tadmorad, Arbel D., et al. (2011) "Probing individual environmental bacteria for viruses by using microfluidic digital PCR" vol. 333(6038), pp. 58-62.
Takagi, Junya, et al., (2005) "Continuous particle separation in a microchannel having asyuuuetrically arranged multiple branches", Lab on a Chip, vol. 5(7), pp. 778-784.
Tamminen, Manu V., et al., (2015) "Single gene-based distinction of individual microbial genomes from a mixed population of microbial cells", Front Microbiol., vol. 6(195), pp. 1-10.
Tewhey, Ryan, et al., (2009) "Microdroplet-based PCR enrichment for large-scale targeted sequencing", Nature Biotechnology, vol. 27, pp. 1025-1031.
Thomann, Yi, et al., (2005) "PMMA Gradient Materials and in situ Nanocoating via Self-Assembly of Semifluorinated Hyperbranched Amphiphiles",Macromolecular Chemistry and Physics, vol. 206(1), pp. 135-141.
Thorsen, Todd, et al., (2001) "Dynamic pattern formation in a vesicle-generating microfluidic device", Physical Review Letter, vol. 86(18), pp. 4163-4166.
Tsai, Scott S H., et al., (2011) "Microfluidic immunomagnetic multi-target sorting—a model for controlling deflection of paramagnetic beads", Lab on a Chip, vol. 11(15), pp. 2577-2582.
Ullal, Adeeti V., et al., (2014) "Cancer cell profiling by barcoding allows multiplexed protein analysis in fine needle aspirates", Science Translation Medicine, vol. 6, Issue 219, pp. 1-22.
Utada, Andrew S., et al., (2007) "Dripping to jetting transitions in co flowing liquid streams", Physical Review Letters, vol. 99(9), pp. 094502-1-094502-4.
Vanapalli, Siva A., et al., (2009) "Hydrodynamic resistance of single confined moving drops in rectangnlar microchannels", Lab on a Chip, vol. 9, pp. 982-990.
Vickers, Jonathan A., et al., (2006) "Generation of Hydrophilic Poly(dimethylsiloxane) for High-Performance Microchip Electrophoresis", Anal. Chem, vol. 78(21), pp. 7446-7452.
Wang, Chao, et al., (2012) "Amphiphilic building blocks for self-assembly: from amphiphiles to supra-amphiphiles", Accounts of Chemical Research, vol. 45(4), pp. 608-618.
Wheeler, Aaron R., et al., (2005) "Digital microfluidics with in-line sample purification for proteomics analyses with MALDI-MS", Anal Chem. vol. 77(2), pp. 534-540.
Whitcombe, David, et al., (1999) "Detection of PCR products using self-probing amplicons and fluorescence", Nature biotechnology, vol. 17(8), pp. 804-807.
Whitesides, George M., (2006) "The origins and the future of microfluidics", Nature, vol. 442, pp. 68-373.
Xia, Younan, et al., (1998) "Soft lithography", Annual Review of Materials Science, vol. 37, pp. 551-575.
Yu, Zhenming, et al., (2014) "Mung bean nuclease treatment increases capture specificity of microdroplet-PCR based targeted DNA enrichment", PLoS One vol. 9(7), e103491, pp. 1-7.
Zeng, Yong, et al., (2010) "High-Performance Single Cell Genetic Analysis Using Microfluidic Emulsion Generator Arrays", Anal Chem, vol. 82(8), pp. 3183-3190.
Zheng, Bo, et al., (2004) "Formation of droplets of in microfluidic channels alternating composition and applications to indexing of concentrations in droplet-based assays", Anal Chem., vol. 76, pp. 4977-4982.
Zhong, Qun, et al., (2011) "Multiplex digital PCR: breaking the one target per color barrier of quantitative PCR", Lab on a Chip, vol. 11 (13), pp. 2167-2174.

(56) References Cited

OTHER PUBLICATIONS

Zhu, Y Y., et al., (2001) "Reverse transcriptase template switching: a SMART approach for full-length cDNA library Construction", BioTechniques, vol. 30(4), pp. 892-897.
Zhu, Zhi, et al., (2012) "Highly sensitive and quantitative detection of rare pathogens through agarose droplet microfluidic emulsion PCR at the single-cell level", Lab on a Chip, vol. 12(20), pp. 3907-3913.
Zien, Tse-Fou, (1969) "Hydrodynamics of bolus flow—an analytical approach to blood flow in capillaries", Bull Math Biophys, vol. 31(4), pp. 681-694.
Integrated DNA Technologies "Molecular Facts and Figures", 2011, 1-9.
Lage, J. M., et al., "Whole Genome Analysis of Genetic Alterations in Small DNA Samples Using Hyperbranched Strand Displacement Amplification and Array-CGH", Genome Res., 13, 2003, p. 294.
Abate, Adam R., et al., (2013) "DNA sequence analysis with droplet-based microfluids", Lab Chip, vol. 13(24), pp. 4864-4869.
Abate, Adam R., et al., (2009) "Beating Poisson encapsulation statistics using close-packed ordering", Lab Chip, vol. 9, pp. 2628-2631.
Abbaspourrad, et al., (2015) "Label-free single-cell protein quantification using a dropbased mix-and-read system", Sci. Rep., 5, p. 12756.
Agargel, (2019) "Agar-Agar", retrieved on Jun. 6, 2019 from https://web.archive.org/web/20170527222040/http://www.agargel.com.br/agar-tecen.html, 3 pages.
Autour, et al., (2017) "Ultrahigh-throughput improvement and discovery of enzymes using droplet-based microfluidic screening" Micromachines, vol. 8(128), pp. 1-21.
Baker, (2012) "Digital PCR hits its stride", Nat. Methods, vol. 9(6), pp. 541-544.
Bjork, et al., (2012) "Metabolite profiling of microfluidic cell culture conditions for droplet based screening", Biomicrojluidics, vol. 9, p. 044128.
Blainey, et al., (2014) "Dissecting genomic diversity, one cell at a time" Nat. Methods, vol. 11(1), pp. 19-21.
Chang, et al., (2012) "Single Molecule Enzyme-Linked Immunosorbent Assays: Theoretical Considerations", J Immunol Methods, vol. 378(1-2), pp. 102-115.
Chen et al., (2017) "Centrifugal micro-channel array droplet generation for highly parallel digital PCR", Lab Chip, 17, pp. 235-240.
Chen et al., (2016) "Spinning micropipette liquid emulsion generator for single cell whole genome amplification", Lab Chip, 16, pp. 4512-4516.
Civelek et al., (2014) "Systems genetics approaches to understand complex traits", Nat. Rev. Genet., 15(1), pp. 34-48.
Collins et al., (2015) "The Poisson distribution and beyond: methods for microfluidic droplet production and single cell encapsulation", Lab on a Chip, 15, pp. 3439-3459.
Costa et al., (2008) "Complex networks: The key to systems biology", Genet. Mol. Biol., 31(3), pp. 591-601.
Elnifro, et al., (2000) "Multiplex PCR: Optimization and Application in Diagnostic Virology", Clin. Microbial. Rev., 13, pp. 559-570.
Fritzsch et al., (2012), "Single-Cell Analysis in Biotechnology, Systems Biology, and Biocatalysis", Annu. Rev. Chem. Biomol. Eng. 3, pp. 129-155.
Gielen, et al., (2016) "Ultrahigh-throughput-directed enzyme evolution by absorbance activated droplet sorting (AADS)", PNAS, pp. E7383-E7389.
Griffiths, et al., (2006) "Miniaturising the laboratory in emulsion droplets Trends" Biotechnol., 24, pp. 395-402.
Guo, et al., (2012) "Droplet microfluidics for highthroughput biological assays.", Lab Chip, pp. 2146-2155.
Halldorsson et al., (2015) "Advantages and challenges of microfluidic cell culture in polydimethylsiloxane devices", Biosens. Bioelectron., 63, pp. 218-231.
Huang, et al., (2017) "Collective generation of milliemulsions by step-emulsification", RSC Advances, 7, pp. 14932-14938.
Joanicot, et al., (2005) "Droplet control for microfluidics", Science, 309(5736), pp. 887-888.
Katepalli, et al., (2014) "Bose, A. Response of Surfactant Stabilized Oil-in-Water Emulsions to the Addition of Particles in an Aqueous Suspension", Langmuir, 30(43), pp. 12736-12742.
Kim, et al., (2017) "Measurement of copy number variation in single cancer cells using rapid-emulsification digital droplet MDA", Microsystems & Nanoengineering 3:17018, pp. 1-7.
Kim, et al., (2014) "Droplet Microfluidics for Producing Functional Microparticles", Langmuir, 30, pp. 1473-1488.
Kimmerling et al., (2016) "A microfluidic platform enabling single-cell RNA-seq of multigenerational lineages", Nature Commun., 7, p. 10220.
Kolodziejczyk, et al., (2015) "The Technology and Biology of Single-Cell RNA Sequencing", Mol. Cell, 58(4), pp. 610-620.
Lance, et al., (2016) "Peering below the diffraction limit: robust and specific sorting of viruses with flow cytometry", Viral J, 13, p. 201.
Macosko, et al., (2015) "Highly parallel genome-wide expression profiling of individual cells using nanoliter droplets" Cell, 161, pp. 1202-1214.
Margulies, et al., (2005) "Genome sequencing in microfabricated high-density picolitre reactors", Nature, 437, pp. 376-380.
Mashaghi, et al., (2016) "Droplet microfluidics: A tool for biology, chemistry and nanotechnology", TrAC—Trends Anal. Chem., 82, pp. 118-125.
Morimoto, et al., (2013) "Three-dimensional cell culture based on microfluidic techniques to mimic living tissues", Biomaterials Science, vol. 1, No. 3, pp. 257-264.
Morimoto, et al., (2009) "Reconstruction of 3D Hierarchic Micro-Tissues using Monodisperse Collagen Microbeads", Micro Electro Mechanical Systems, IEEE 22nd International Conference, pp. 56-59.
Pinheiro, et al., (2012) Evaluation of a droplet digital polymerase chain reaction format for DNA copy number quantification, Anal. Chem., 84, pp. 1003-1011.
Romero, et al., (2015) "Dissecting enzyme function with microfluidic-based deep mutational scanning", PNAS, 112(23), pp. 7159-7164.
Sandberg, et al., (2009) "Flow cytometry for enrichment and titration in massively parallel DNA sequencing", Nucleic Acids Res, 37(8), p. e63.
Song, et al., (2006) "On-Chip Titration of an Anticoagulant Argatroban and Determination of the Clotting Time within Whole Blood or Plasma Using a Plug-Based Microfluidic System", Anal. Chem., 78(14), pp. 4839-4849.
Soon, et al., (2013) "High-throughput sequencing for biology and medicine", Mol. Syst. Biol., 9(64), pp. 1-14.
Spies, et al., (2017) "Genome-wide reconstruction of complex structural variants using read clouds", Nat. Methods, 14(9), pp. 915-920.
Sukovich, et al., (2017) "Sequence specific sorting of DNA molecules with FACS using 3dPCR", Sci. Rep., 7, p. 39385.
Taly, et al., (2013) "Multiplex picodroplet digital PCR to detect KRAS mutations in circulating DNA from the plasma of colorectal cancer patients", Clin. Chem., 59, pp. 1722-1731.
Tran, et al., (2013) "From tubes to drops: dropletbased biology microfluidics for ultrahigh-throughput", J Phys. D. Appl. Phys., 46, p. 114004.
Weaver, et al., (2014) "Advances in high-throughput single-cell microtechnologies", Curr. Opin. Biotechnol., 0, pp. 114-123.
Yan, et al., (2017) "Intestinal Enteroendocrine Lineage Cells Possess Homeostatic and Injury-Inducible Stem Cell Activity", Cell Stem Cell, 21, pp. 78-90.
Zhu, et al., (2017) "Hydrogel Droplet Microfluidics for High-Throughput Single Molecule/Cell Analysis", Acc. Chem. Res., 50(1), pp. 22-31.
Zilionis, et al., (2017) "Single-cell barcoding and sequencing using droplet microfluidics", Nat. Protoc., 12(1), pp. 44-73.

* cited by examiner c. Barcoding Tagmented Genomes

C

B

A

B

Lorenz Curves of Barcode Group Genome Coverage, by Species

SEQUENCE LISTING

<160> NUMBER OF SEQ ID NOS: 27

<210> SEQ ID NO 1
<211> LENGTH: 35
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (28)..(35)
<223> OTHER INFORMATION: n is a, c, g, or t

<400> SEQUENCE: 1
gtgagtgatg gttgaggtag tgtggagnnn nnnnn          35

<210> SEQ ID NO 2
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 2
gtgagtgatg gttgaggtag tgtggag          27

<210> SEQ ID NO 3
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 3
cactcactac caactccatc acacctc          27

<210> SEQ ID NO 4
<211> LENGTH: 35
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (28)..(35)
<223> OTHER INFORMATION: n is a, c, g, or t

<400> SEQUENCE: 4
gtgagtgatg gttgaggtag tgtggagnnn nnnnn          35

<210> SEQ ID NO 5
<211> LENGTH: 78
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (46)..(60)
<223> OTHER INFORMATION: n is a, c, g, or t

<400> SEQUENCE: 5
gcagctggcg taatagcgag tacaatctgc tctgatgccg catagnnnnn nnnnnnnnn          60 taagccagcc ccgacact          78

<210> SEQ ID NO 6
<211> LENGTH: 51

<212> TYPE: DNA
<213> ORGANISM: Artificial Sequence
<220> FEATURE:
<223> OTHER INFORMATION: Synthetic Sequence

<400> SEQUENCE: 6
ctgtctctta tacacatctc cgagcccacg agacgtgtcg gggctggctt a    51

<210> SEQ ID NO 7
<211> LENGTH: 41
<212> TYPE: DNA
<213> ORGANISM: Artificial Sequence
<220> FEATURE:
<223> OTHER INFORMATION: Synthetic Sequence

<400> SEQUENCE: 7
caagcagaag acggcatacg agatcagctg gcgtaatagc g    41

<210> SEQ ID NO 8
<211> LENGTH: 43
<212> TYPE: DNA
<213> ORGANISM: Artificial Sequence
<220> FEATURE:
<223> OTHER INFORMATION: Synthetic Sequence

<400> SEQUENCE: 8
aatgatacgg cgaccaccga gatctacact cgtcggcagc gtc    43

<210> SEQ ID NO 9
<211> LENGTH: 128
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (51)..(65)
<223> OTHER INFORMATION: n is a, c, g, or t

<400> SEQUENCE: 9
gtatgcgact tcagtacatc gtcccgatgc tctgcacagt cgaccgctga nnnnnnnnnn    60
nnnnncagcg atcccgagtc agatcgatgc cactgagacc tgtgagtgat ggttgaggta    120
gtgtggag    128

<210> SEQ ID NO 10
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 10
ctccacacta cctcaaccat cactcacagg tctcagtggc    40

<210> SEQ ID NO 11
<211> LENGTH: 38
<212> TYPE: DNA
<213> ORGANISM: Artificial Sequence
<220> FEATURE:
<223> OTHER INFORMATION: Synthetic Sequence

<400> SEQUENCE: 11
gtatgcgact tcagtacatc gtcccgatgc tctgcaca    38

<210> SEQ ID NO 12

```
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 12
gtatgcgact tcagtacatc gtcccgatgc tctgcacagt cgaccgctga            50

<210> SEQ ID NO 13
<211> LENGTH: 79
<212> TYPE: DNA
<213> ORGANISM: Artificial Sequence
<220> FEATURE:
<223> OTHER INFORMATION: Synthetic Sequence

<400> SEQUENCE: 13
aatgatacgg cgaccaccga gatctacacg tatgcgactt cagtacatcg tcccgatgct    60
ctgcacagtc gaccgctga                                              79

<210> SEQ ID NO 14
<211> LENGTH: 47
<212> TYPE: DNA
<213> ORGANISM: Artificial Sequence
<220> FEATURE:
<223> OTHER INFORMATION: Synthetic Sequence

<400> SEQUENCE: 14
caagcagaag acggcatacg agatcatgcc tagtctcgtg ggctcgg                47

<210> SEQ ID NO 15
<211> LENGTH: 63
<212> TYPE: DNA
<213> ORGANISM: Artificial Sequence
<220> FEATURE:
<223> OTHER INFORMATION: Synthetic Sequence

<400> SEQUENCE: 15
cagcgatccc gagtcagatc gatgccactg agacctgtga gtgatggttg aggtagtgtg    60
gag                                                                63

<210> SEQ ID NO 16
<211> LENGTH: 15
<212> TYPE: DNA
<213> ORGANISM: Artificial sequence
<220> FEATURE:
<223> OTHER INFORMATION: synthetic sequence

<400> SEQUENCE: 16
aggatgttta gtatg                                                   15

<210> SEQ ID NO 17
<211> LENGTH: 15
<212> TYPE: DNA
<213> ORGANISM: Artificial sequence
<220> FEATURE:
<223> OTHER INFORMATION: synthetic sequence

<400> SEQUENCE: 17
gcggcaccac acttg                                                   15

<210> SEQ ID NO 18
<211> LENGTH: 15
<212> TYPE: DNA
<213> ORGANISM: Artificial sequence
```

```
<220> FEATURE:
<223> OTHER INFORMATION: synthetic sequence

<400> SEQUENCE: 18
cccatatcca cagtg                                                        15

<210> SEQ ID NO 19
<211> LENGTH: 15
<212> TYPE: DNA
<213> ORGANISM: Artificial sequence
<220> FEATURE:
<223> OTHER INFORMATION: synthetic sequence

<400> SEQUENCE: 19
atgaccaagc gatgg                                                        15

<210> SEQ ID NO 20
<211> LENGTH: 15
<212> TYPE: DNA
<213> ORGANISM: Artificial sequence
<220> FEATURE:
<223> OTHER INFORMATION: synthetic sequence

<400> SEQUENCE: 20
gcaggaccgt tacca                                                        15

<210> SEQ ID NO 21
<211> LENGTH: 15
<212> TYPE: DNA
<213> ORGANISM: Artificial sequence
<220> FEATURE:
<223> OTHER INFORMATION: synthetic sequence

<400> SEQUENCE: 21
aaaacatagt tgagt                                                        15

<210> SEQ ID NO 22
<211> LENGTH: 15
<212> TYPE: DNA
<213> ORGANISM: Artificial sequence
<220> FEATURE:
<223> OTHER INFORMATION: synthetic sequence

<400> SEQUENCE: 22
atgttttaac acatc                                                        15

<210> SEQ ID NO 23
<211> LENGTH: 15
<212> TYPE: DNA
<213> ORGANISM: Artificial sequence
<220> FEATURE:
<223> OTHER INFORMATION: synthetic sequence

<400> SEQUENCE: 23
gacgatgtca taaca                                                        15

<210> SEQ ID NO 24
<211> LENGTH: 15
<212> TYPE: DNA
<213> ORGANISM: Artificial sequence
<220> FEATURE:
<223> OTHER INFORMATION: synthetic sequence

<400> SEQUENCE: 24
ccatactagt tcgca                                                        15
```

```
<210> SEQ ID NO 25
<211> LENGTH: 15
<212> TYPE: DNA
<213> ORGANISM: Artificial sequence
<220> FEATURE:
<223> OTHER INFORMATION: synthetic sequence

<400> SEQUENCE: 25
aaggctgtgc ggttg                                                    15

<210> SEQ ID NO 26
<211> LENGTH: 15
<212> TYPE: DNA
<213> ORGANISM: Artificial sequence
<220> FEATURE:
<223> OTHER INFORMATION: synthetic sequence

<400> SEQUENCE: 26
aaactgagga tcatc                                                    15

<210> SEQ ID NO 27
<211> LENGTH: 15
<212> TYPE: DNA
<213> ORGANISM: Artificial sequence
<220> FEATURE:
<223> OTHER INFORMATION: synthetic sequence

<400> SEQUENCE: 27
tttcgatcgc gtagc                                                    15
```

SINGLE CELL GENOMIC SEQUENCING USING HYDROGEL BASED DROPLETS

CROSS-REFERENCE

The present application is a continuation of U.S. patent application Ser. No. 16/468,652, filed Jun. 11, 2019, which is a continuation of PCT/US2017/068006, filed Dec. 21, 2017 which claims the benefit of U.S. Provisional Patent Application No. 62/437,605, filed Dec. 21, 2016, the disclosures of which are herein incorporated by reference.

INCORPORATION BY REFERENCE OF SEQUENCE LISTING PROVIDED AS A TEXT FILE

A sequence listing is provided herewith as a text file, UCSF-530CON_SF-2016-152-3_Seq_Listing_as_of_March_2021_ST25, created on Mar. 9, 2021 and having a size of 7000 bytes. The contents of the text file are incorporated by reference herein in their entirety.

GOVERNMENT SUPPORT

This invention was made with government support under grant nos. AR068129, R01 EB019453 and R21 HG007233 awarded by the National Institutes of Health; grant no. 1253293 awarded by the National Science Foundation; grant no. HR0011-12-C-0065 awarded by the Department of Defense, Defense Advanced Research Projects Agency; and grant no. N66001-12-C-4211 awarded by the Space and Naval Warfare Systems Center. The government has certain rights in the invention.

INTRODUCTION

A common challenge when applying single cell sequencing to heterogeneous systems is that they often contain massive numbers of cells: A centimeter-sized tumor can contain hundreds of millions of mutated cancer cells, while a milliliter of sea water can contain millions of microbes. Moreover, each cell has a tiny quantity of DNA, making it challenging to accurately amplify and sequence so many single cells. Methods based on optical tweezers, flow cytometry, microfluidics, gel encapsulation, and virtual microfluidics can isolate and process hundreds of single cells for sequencing, but this constitutes a minute fraction of most communities. The sparseness of the sampling limits the questions that can be addressed, with the majority of findings relating to the most abundant subpopulations. For example, common environmental communities contain >1500 taxa, with rare taxa present at <0.1%, most of which are missed by single cell sequencing; indeed, the difficulty of capturing these cells is the basis of "microbial dark matter" the overwhelming abundance of species thought to exist, but that have never been characterized. Therefore, a method that could markedly increase the number of cells sequenced through single cell sequencing would impact a broad range of problems across biology where heterogeneity is important.

SUMMARY

The present disclosure provides ultrahigh-throughput single cell genomic sequencing methods, referred to herein as "SiC-seq", which methods include encapsulating single cells in molten gel droplets to facilitate bulk cell lysis and purification of genomic DNA in microgels. Systems and devices for practicing the subject methods are also provided.

BRIEF DESCRIPTION OF THE DRAWINGS

The invention may be best understood from the following detailed description when read in conjunction with the accompanying drawings. Included in the drawings are the following figures:

FIG. 3A) Barcode droplets are generated by encapsulating random DNA oligos at limiting dilution with PCR reagents using a flow focus droplet maker. The droplets are thermal cycled, yielding a droplet containing clonal population of a unique barcode sequence for every ~9 empty droplets (SYBR stained for visualization). FIG. 3B) Cells, e.g., bacteria, are encapsulated at limiting dilution with molten gel, e.g., molten agarose, to generate single cell containing microgels, e.g., single cell containing agarose microgels. The single cell genomes are purified through a series of bulk washes, e.g., detergent and enzyme washes. The purified single cell genomes are then re-encapsulated and labeled, e.g., tagmented. FIG. 3C) The labeled, e.g., tagmented, genome-containing microgels are merged with droplets containing barcode and nucleic acid amplification reagents, e.g., PCR reagents. During thermal cycling the barcodes splice onto the labeled, e.g., tagmented, genome fragments, generating chimeric molecules consisting of the barcode attached to a random fragment of the cell genome ready for massively parallel sequencing.

FIG. 5A) Distribution of reads in each barcode group. FIG. 5B) Histogram of the purity of each barcode group, which is defined as the fraction of reads mapping to the most mapped species for that group. FIG. 5C) Relative abundance estimates of each species are calculated using from left to right for each species: reads classified using Bowtie2 (Bowtie2 Reads), barcodes classified using Bowtie2 (Bowtie2 Barcodes), and reads classified using Kraken (Kraken reads). FIG. 5D) Relative coverage distribution for reads aggregated from all barcode groups for each microbe. FIG. 5E) Coverage histogram binned by relative coverage. See FIGS. 6A and 6B for coverage maps of other species.

FIGS. 6A and 6B depict the distribution of SiC-seq reads obtained from sequencing the mixed community of known microbes. FIG. 6A) Aggregate Coverage over *Bacillus subtilis* and *Saccharomyces cerevisiae* reference genomes in the SiC-seq validation dataset for 10 kb bins. FIG. 6B) Mapping positions of reads for randomly chosen barcode *Staphylococcus* groups with >2000 reads.

FIG. 9A) Distribution of antibiotic resistance (AR) genes according to genus of host microbe. Using in silico cytometry, the association of AR genes with the taxonomic classification is deduced. The opacity of connecting lines reflects the number of interactions detected in the database. FIG. 9B) Relative abundance of virulence factors in each genus detected in the community. The virulence ratio is the ratio between the number of barcode groups observed with virulence factors and the number of total barcode groups for that species, normalized to a scale from 0 to 1. FIG. 9C) Relative potential for transduction between bacterial taxa in a community plotted as a heat map.

DETAILED DESCRIPTION

Figure 1:
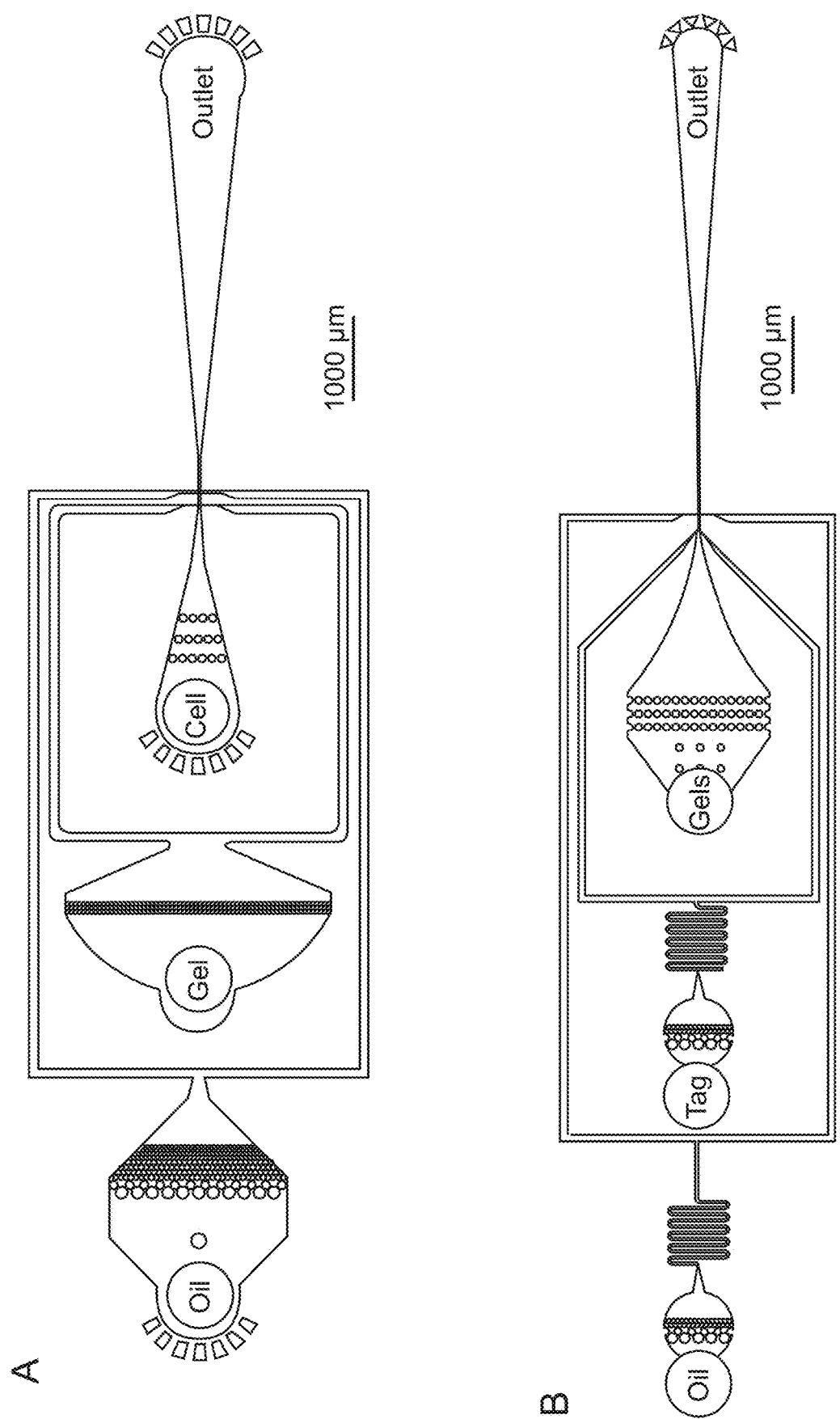
FIG. 1 provides schematics of microfluidic devices according to one embodiment of the present disclosure used to a) generate barcode droplets and encapsulate cells in microgels; b) re-encapsulate gels with tagmentation reagents; and c) merge gel droplets with barcode droplets and PCR droplets.
Figure 1:
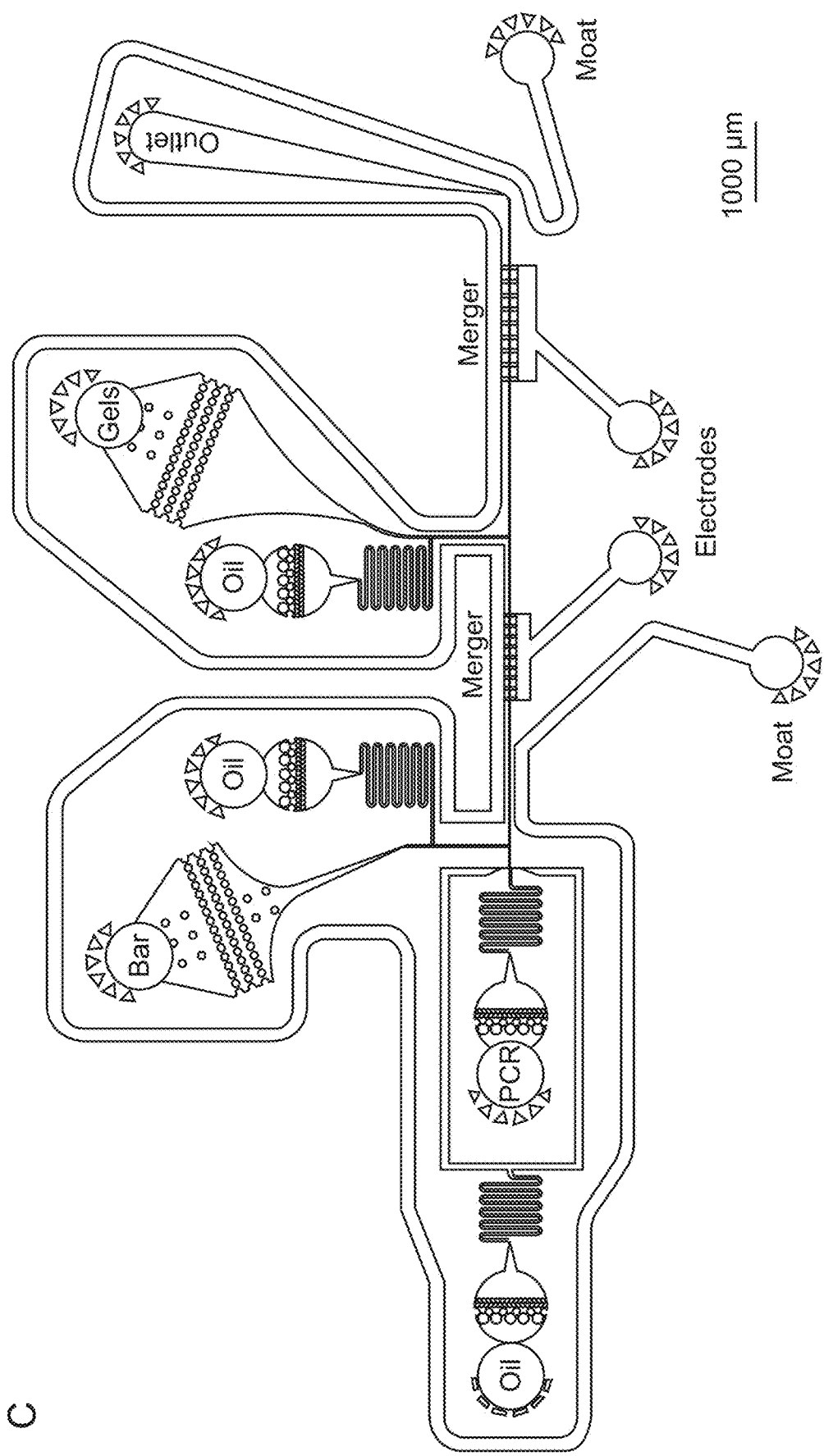

The present disclosure provides methods of sequencing single cell genomic DNA for analyzing, e.g., metagenomes, copy number variants, and the genetic profile of complex biological samples. The methods described herein facilitate high-throughput processing of populations of single cells and subsequent sequencing of genomic DNA. Systems and devices for practicing the subject methods are also provided.

Before the present invention is described in greater detail, it is to be understood that this invention is not limited to the particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a droplet" includes a plurality of such droplets unless the context clearly dictates otherwise.

It is further noted that the claims may be drafted to exclude any element, e.g., any optional element. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Further, the dates of publication provided may be different from the actual publication dates which may need to be independently confirmed. To the extent the disclosure or the definition or usage of any term herein conflicts with the disclosure or the definition or usage of any term in an application or publication incorporated by reference herein, the instant application shall control.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The terms "nucleic acid barcode sequence", "nucleic acid barcode", "barcode", and the like as used herein refer to a nucleic acid having a sequence which can be used to identify and/or distinguish one or more first molecules to which the nucleic acid barcode is conjugated from one or more second molecules. Nucleic acid barcode sequences are typically short, e.g., about 5 to 20 bases in length, and may be conjugated to one or more target molecules of interest or amplification products thereof. Nucleic acid barcode sequences may be single or double stranded.

The terms "nucleic acid", "nucleic acid molecule", "oligonucleotide" and "polynucleotide" are used interchangeably and refer to a polymeric form of nucleotides of any length, either deoxyribonucleotides or ribonucleotides, or analogs thereof. The terms encompass, e.g., DNA, RNA and modified forms thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

The term "nucleic acid sequence" or "oligonucleotide sequence" refers to a contiguous string of nucleotide bases and in particular contexts also refers to the particular placement of nucleotide bases in relation to each other as they appear in a oligonucleotide. Similarly, the term "polypeptide sequence" or "amino acid sequence" refers to a contiguous string of amino acids and in particular contexts also refers to the particular placement of amino acids in relation to each other as they appear in a polypeptide.

As used herein the term "isolated," when used in the context of an isolated cell, refers to a cell of interest that is in an environment different from that in which the cell naturally occurs. "Isolated" is meant to include cells that are within samples that are substantially enriched for the cell of interest and/or in which the cell of interest is partially or substantially purified.

The terms "droplets", "droplet" and the like are used herein to refer to emulsion-based compartments capable of encapsulating and/or containing one or more single cells as described herein and/or one or more barcodes as described herein. Droplets may include a first fluid phase, e.g., an aqueous phase (e.g., water or hydrogel), bounded by a second fluid phase (e.g., oil) which is immiscible with the first fluid phase. In some embodiments, the second fluid phase will be an immiscible phase carrier fluid. Thus droplets according to the present disclosure may be provided as aqueous-in-oil emulsions. The term "droplet" is also used herein in the context of "solidified microgel droplets" to refer to a molten gel containing droplet or droplets, wherein the molten gel has been solidified leaving a solidified microgel surrounded by an immiscible phase film, e.g., an oil film. Droplets as used or generated in connection with the subject methods, devices, and/or systems may be sphere shaped or they may have any other suitable shape, e.g., an ovular or oblong shape. Droplets as described herein may include a liquid phase and/or a solid phase material. In some embodiments, droplets according to the present disclosure include a gel material. In some embodiments, the subject droplets have a dimension, e.g., a diameter, of or about 1.0

μm to 1000 μm, inclusive, such as 1.0 μm to 750 μm, 1.0 μm to 500 μm, 1.0 μm to 100 μm, 1.0 μm to 10 μm, or 1.0 μm to 5 μm, inclusive. In some embodiments, droplets as described herein have a dimension, e.g., diameter, of or about 1.0 μm to 5 μm, 5 μm to 10 μm, 10 μm to 100 μm, 100 μm to 500 μm, 500 μm to 750 μm, or 750 μm to 1000 μm, inclusive. Furthermore, in some embodiments, droplets as described herein have a volume ranging from about 1 fL to 1 nL, inclusive, such as from 1 fL to 100 pL, 1 fL to 10 pL, 1 fL to 1 pL, 1 fL to 100 fL, or 1 fL to 10 fL, inclusive. In some embodiments, droplets as described herein have a volume of 1 fL to 10 fL, 10 fL to 100 fL, 100 fL to 1 pL, 1 pL to 10 pL, 10 pL to 100 pL or 100 pL to 1 nL, inclusive. In addition, droplets as described herein may have a size and/or shape such that they may be produced in, on, or by a microfluidic device and/or flowed from or applied by a microfluidic device.

As used herein, the term "carrier fluid" refers to a fluid configured or selected to contain one or more droplets, as described herein. A carrier fluid may include one or more substances and may have one or more properties, e.g., viscosity, which allows it to be flowed through a microfluidic device or a portion thereof. In some embodiments, carrier fluids include, for example: oil or water, and may be in a liquid or gas phase.

As used in the claims, the term "comprising", which is synonymous with "including", "containing", and "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, and/or ingredient not specifically recited. For example, when the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter.

With respect to the terms "comprising", "consisting essentially of", and "consisting of", where one of these three terms is used herein, the presently disclosed subject matter can include the use of either of the other two terms.

Methods

As summarized above, the present disclosure provides ultrahigh-throughput single cell genomic sequencing methods, referred to herein as SiC-seq, which methods include encapsulating single cells in molten gel droplets to facilitate bulk cell lysis and purification of genomic DNA in microgels. These methods facilitate the sequencing of single cell genomic DNA for analyzing, e.g., metagenomes, copy number variants, and the genetic profile of complex biological samples.

Methods for Sequencing Single Cell Genomic DNA

The present disclosure provides methods for sequencing single cell genomic DNA. Methods of the present disclosure provide ultrahigh-throughput sequencing of single cell genomes. In some embodiments, droplet microfluidics is used to isolate, fragment, and barcode the single cell genomes of a population of cells, allowing single cell genomic DNA to be recovered by grouping reads by barcode.

Isolation of Single Cells:

Using the methods described herein, single cells can be isolated in droplets. In some embodiments, single cells are encapsulated in droplets which may facilitate the process of purifying genomic DNA, without mixing the genomic contents of individual single cells. In some embodiments, encapsulating single cells in droplets is achieved using a microfluidic device that comprises a droplet generator. For example, a population of single cells may be flowed through a channel of a microfluidic device, the microfluidic device including a droplet generator in fluid communication with the channel, under conditions sufficient to effect inertial ordering of the cells in the channel, thereby providing periodic injection of the cells into the droplet generator to encapsulate single cells in individual droplets. In some embodiments, the method of encapsulating single cells in droplets comprises the addition of an immiscible phase fluid, e.g., oil, to generate an emulsion of droplets each containing a single cell. Additional description of cell encapsulation using microfluidic droplet generators is found, e.g., in U.S. Patent Application Publication No. 20150232942, the disclosure of which is incorporated by reference herein in its entirety.

In some embodiments, a droplet in which a single cell is encapsulated comprises a polymeric material. For example, suitable polymeric materials may include interpenetrating polymer networks (IPNs); a synthetic hydrogel; a semi-interpenetrating polymer network (sIPN); a thermoresponsive polymer; and the like. For example, in some embodiments, a suitable polymer comprises a co-polymer of polyacrylamide and poly(ethylene glycol) (PEG). In some embodiments, ta suitable polymer comprises a co-polymer of polyacrylamide and PEG, and further comprises acrylic acid.

In some embodiments, a droplet in which a single cell is encapsulated may be a microgel droplet. In such embodiments, a microgel droplet may be a hydrogel droplet comprising a hydrogel polymer. Suitable hydrogel polymers may include, but are not limited to the following: actic acid, glycolic acid, acrylic acid, 1-hydroxyethyl methacrylate (HEMA), ethyl methacrylate (EMA), propylene glycol methacrylate (PEMA), acrylamide (AAM), N-vinylpyrrolidone, methyl methacrylate (MMA), glycidyl methacrylate (GDMA), glycol methacrylate (GMA), ethylene glycol, fumaric acid, and the like. Some hydrogel polymers require the use of a cross linking agent. Common cross linking agents include tetraethylene glycol dimethacrylate (TEGDMA) and N,N'-methylenebisacrylamide. The hydrogel droplets can be homopolymeric, or can comprise co-polymers of two or more of the aforementioned polymers. Exemplary hydrogel droplets include, but are not limited to, a copolymer of poly(ethylene oxide) (PEO) and poly(propylene oxide) (PPO); Pluronic™ F-127 (a difunctional block copolymer of PEO and PPO of the nominal formula $EO_{100}$-$PO_{65}$-$EO_{100}$, where EO is ethylene oxide and PO is propylene oxide); poloxamer 407 (a tri-block copolymer consisting of a central block of poly(propylene glycol) flanked by two hydrophilic blocks of poly(ethylene glycol)); a poly(ethylene oxide)-poly(propylene oxide)-poly(ethylene oxide) co-polymer with a nominal molecular weight of 12,500 Daltons and a PEO:PPO ratio of 2:1); a poly(N-isopropylacrylamide)-base hydrogel (a PNIPAAm-based hydrogel); a PNIPAAm-acrylic acid co-polymer (PNIPAAm-co-AAc); poly (2-hydroxyethyl methacrylate); poly(vinyl pyrrolidone); and the like.

Of particular use in methods described herein are microgel droplets that are able to transform from one state to another, e.g., from a liquid state to a solid state. In some embodiments, a microgel droplet is a hydrogel droplet comprising a hydrogel polymer, wherein the hydrogel polymer is a thermoresponsive polymer. A thermoresponsive polymer generally exhibits a change in its physical properties with temperature. For example, a thermoresponsive polymer may exhibit a volume phase transition at a certain temperature, which causes a sudden change in the solvation state. Thermoresponsive polymers suitable for use in methods of the present disclosure may include those that become soluble upon heating. For example, agarose, e.g., a low gelling temperature agarose, can be suitable for use in the methods described herein. In some embodiments, a suitable thermoresponsive polymer, e.g., a suitable agarose, has a gel point of from about 20° C. to about 40° C., e.g., from about 25° C. to about 35° C., e.g., about 30° C. A thermoresponsive polymer may have a gel point that is distinct from its melting point. As used herein, the term "gel point" of a thermoresponsive polymer refers to the temperature at which a liquid thermoresponsive polymer solidifies, e.g., transitions into a solid state. As used herein, the term "melting point" or "melting temperature" of a thermoresponsive polymer refers to the temperature at which a solid thermoresponsive polymer melts, e.g., transitions into a liquid state. In some embodiments, a suitable thermoresponsive polymer, e.g., a suitable agarose, has a gel point of from about 5° C. to about 45° C., e.g., from about 5° C. to about 10° C., from about 10° C. to about 15° C., from about 15° C. to about 20° C., from about 25° C. to about 30° C., from about 30° C. to about 35° C., from about 35° C. to about 40° C., from about 40° C. to about 45° C., e.g., about 20° C. In some embodiments, a suitable thermoresponsive polymer, e.g., a suitable agarose, has a gel point of about 20° C.

In some embodiments, a suitable thermoresponsive polymer, e.g., a suitable agarose, has a melting point of from about 60° C. to about 95° C., e.g., from about 60° C. to about 65° C., from about 65° C. to about 70° C., from about 70° C. to about 75° C., from about 75° C. to about 80° C., from about 80° C. to about 85° C., from about 85° C. to about 90° C., from about 90° C. to about 95° C., e.g., about 60° C. In some embodiments, a suitable thermoresponsive polymer, e.g., a suitable agarose, has a melting point of about 60° C.

In some embodiments, single cells can be encapsulated in molten gel droplets, e.g., molten agarose gel droplets, which can be solidified into solidified microgel droplets. In some embodiments, molten agarose gel droplets are solidified by cooling. In some embodiments, a microgel droplet can comprise a polymer that is transformed into a solid state upon cross linking. For example, hydrogel droplets can comprise acrylamide and solidifies upon chemical and/or photo cross linking. For example, microgel droplets can comprise poly(ethylene glycol) (PEG) and solidifies upon chemical and/or photo cross linking. In some embodiments, hydrogel droplets can comprise alginate, which is solidified upon the addition of calcium.

In some embodiments, a microgel droplet for use in the methods described herein includes or forms a solidified microgel having pores sized to retain nucleic acids within the solidified microgel. In some embodiments, a solidified microgel includes pores sized to retain nucleic acids within the solidified microgel, but allows other materials to move in and out of the solidified microgel. For example, large molecular macromolecules (e.g., genomic DNA) are retained in the solidified microgel, while other materials such as lipids and proteins are able to move out of the solidified microgel, e.g., as a result of one or more washing steps. The pore size of a solidified microgel is a function of the microgel type and concentration used. In some embodiments, the solidified microgel is a solidified agarose microgel having pore sizes that are a function of the agarose type and concentration used. In some embodiments, the pore size of a solidified microgel made from a microgel formulation at about 1.5% to about 2% concentration, e.g., at about 1.3% to about 1.5%, at about 1.4% to about 1.6%, at about 1.5% to about 1.7%, at about 1.6% to about 1.8%, at about 1.7% to about 1.9%, at about 1.8% to about 2.0%, at about 1.9% to about 2.1%, can have pore sizes in the range of from about 50 nm to about 150 nm, e.g., from about 30 nm to about 50 nm, from about 50 nm to about 70 nm, from about 70 nm to about 90 nm, from about 90 nm to about 110 nm, from about 110 nm to about 130 nm, from about 130 nm to about 150 nm, from about 150 nm to about 170 nm. A person of ordinary skill in the art will be able to determine a microgel pore size. For example, a microgel pore size may be determined by methods described in Narayanan et al., *Journal of Physics: Conference Series.* 2006, 28:83-86 the disclosure of which is incorporated by reference herein, Accordingly, in some embodiments, a method of sequencing single cell genomic DNA as provided by the present disclosure includes: encapsulating a population of single cells in molten gel droplets to provide a population of molten gel droplets, wherein each molten gel droplet of the population contains zero or one cell.

Methods for sequencing single cell genomic DNA from a population of single cells as provided herein, may find use in sequencing single cell genomic DNA from a complex mixture of cells. In some embodiments, a population of single cells may be homogeneous or heterogeneous. In some embodiments, a population of single cells may include eukaryotic cells (e.g., mammalian cells, fungal cells, etc.) or prokaryotic cells (e.g., bacterial cells), or a combination thereof. In some embodiments, a population of single cells may be obtained from a variety of sources, e.g., blood samples collected by venipuncture, blood samples collected by finger stick, cerebral spinal fluid samples collected by lumbar puncture, environmental samples, etc.

Purification of Single Cell Genomic DNA:

According to embodiments of the methods described herein, the genomic DNA of individual single cells is purified in bulk, while maintaining isolation of genomic DNA from different cells in different solidified microgels. In some embodiments, bulk purification of single cell genomic DNA is facilitated by the encapsulation of single cells in microgel droplets that can be solidified. For example, a method of purifying single cell genomic DNA from a population of single cells includes encapsulating the population of single cells in molten gel droplets to provide a population of molten gel droplets, wherein each molten gel droplet of the population contains zero or one cell. The population of molten gel droplets is then solidified to provide a population of solidified microgel droplets. The method includes breaking the emulsions of the solidified microgel droplets to provide a population of solidified microgels, and exposing the population of solidified microgels in bulk to lysis conditions.

In some embodiments, the population of solidified microgels is exposed in bulk to lysis conditions sufficient to lyse cells contained within the population of solidified microgels. In some embodiments, lysis conditions include contacting the population of solidified microgels with a lytic enzyme. Those of ordinary skill in the art will recognize that different lytic enzymes could be used depending on the type of cells that are in the solidified microgels. For example, bacterial cells can be lysed using one or more lytic enzymes including, e.g., achromopeptidase, labiase, lysostaphin, lysozyme, mutanolysin, and the like. Yeast cells can be lysed using one or more lytic enzymes including, e.g., zymolyase, kitalase, GLUCANEX, lyticase, and the like. Plant cells can be lysed using one or more lytic enzymes including, e.g., cellulose, pectinase, pectolyase, and the like. Mammalian cells can be lysed using one or more lytic enzymes including, e.g., tetanolysin, α-hemolysin, steptolysin O, and the like. A person of ordinary skill in the art will be able to select from multiple lytic enzymes the one, or combination that is most suitable for lysing cells of interest. In some embodiments, the disclosed methods specifically include contacting the population of solidified microgels in bulk with two or more different lytic enzymes, e.g., wherein the two or more different lytic enzymes are capable of lysing different cell types. Such contacting may occur simultaneously or in separate temporal steps, e.g., separated by one or more wash steps.

In some embodiments, cell lysis includes contacting the population of solidified microgels in bulk with one or more lytic enzymes, e.g., a mixture of lytic enzymes, and incubating the solidified microgels for a period of time sufficient to lyse the cells, e.g., from about 5 min to about 24 hours, inclusive, e.g., about 10 min to about 24 hours, about 20 min to about 24 hours, about 30 min to about 24 hours, about 40 min to about 24 hours, about 50 min to about 24 hours, about 1 hour to about 24 hours, about 3 hours to about 24 hours, about 6 hours to about 24 hours, about 9 hours to about 24 hours, about 12 hours to about 24 hours, about 15 hours to about 24 hours, about 18 hours to about 24 hours, or about 21 hours to about 24 hours. In some embodiments, cell lysis includes contacting the population of solidified microgels in bulk with one or more lytic enzymes, e.g., a mixture of lytic enzymes, and incubating the solidified microgels for about 10 min to about 20 min, about 20 min to about 30 min, about 30 min to about 1 hour, about 1 hour to about 3 hours, about 3 hours to about 6 hours, about 6 hours to about 9 hours, about 9 hours to about 12 hours, about 12 hours to about 15 hours, about 15 hours to about 18 hours about 18 hours to about 21 hours, or about 21 hours to about 24 hours. In some embodiments, the population of solidified microgels is incubated with the mixture of lytic enzymes overnight to lyse the cells contained within the solidified microgels.

In some embodiments, the method of purifying single cell genomic DNA from a population of single cells includes contacting the population of solidified microgels with one or more detergents to solubilize cellular material contained within the population of solidified microgels. For example, detergents can solubilize membrane lipids that are released upon cell lysis. Suitable detergents for use in methods of the present disclosure include those that are well known in the art. Common detergents include: sodium dodecyl sulfate (SDS), SDS lauryl, SDS C12, TRITON X-100, TRITON X-114, NP-40, TWEEN-20, TWEEN-80, octyl glucoside, octylthio glucoside, 3-((3-cholamidopropyl) dimethylammonio)-1-propanesulfonate (CHAPS), lithium dodecyl sulfate, and the like. In some embodiments, the disclosed methods specifically include contacting the population of solidified microgels in bulk with two or more different detergents. Such contacting may occur simultaneously or in separate temporal steps, e.g., separated by one or more wash steps.

In some embodiments, the method of purifying single cell genomic DNA from a population of single cells includes contacting the population of solidified microgels with a protease to digest cellular proteins contained within the population of solidified microgels. Suitable proteases for use in methods of the present disclosure include those that are well known in the art, e.g., a serine protease, a subtilisin-type protease, e.g., proteinase K, brofasin, and the like. In some embodiments, the population of solidified microgels are incubated with proteinase K under conditions sufficient to digest cellular proteins, e.g., at 50° C. for 30 minutes or any other suitable temperature and time sufficient to digest cellular proteins contained within the population of solidified microgels.

As described herein, upon cell lysis within the population of solidified microgels, large molecular weight macromolecules (e.g., genomic DNA) are trapped within the solidified microgels. Hence, the genomic DNA from one cell does not mix with the genomic DNA of another cell, efficiently compartmentalizing the genomic DNA of each individual single cell into its respective solidified microgel. Due to the porosity of the solidified microgels, smaller sized molecules such as lytic enzymes, proteases, and detergents are able to freely enter the solidified microgel to, e.g., digest proteins, digest fragments of cell walls and solubilize lipids. Following successful cell lysis, the genomic DNA can then be purified.

In some embodiments, the population of solidified microgels is washed to remove lytic enzymes and/or detergents and other chemical species which may inhibit downstream molecular biology reactions, such as PCR reactions. The population of solidified microgels is washed by contacting the population of solidified microgels with a washing buffer. In some embodiments, washing the solidified microgels includes contacting the population of solidified microgels with a series of washing buffers. In some embodiments, the washing buffer includes TWEEN-20 and ethanol, although any suitable washing buffer known in the art may be utilized.

Accordingly, a method of sequencing single cell genomic DNA as provided by the present disclosure includes: encapsulating a population of single cells in molten gel droplets to provide a population of molten gel droplets, wherein each molten gel droplet of the population contains zero or one cell; solidifying the population of molten gel droplets to provide a population of solidified microgel droplets; breaking the emulsions of the solidified microgel droplets to provide a population of solidified microgels; exposing the population of solidified microgels in bulk to lysis conditions sufficient to lyse cells contained within the population of solidified microgels; and purifying genomic DNA from cells contained within the population of solidified microgels in bulk to provide a population of solidified microgels including purified genomic DNA.

An important advantage of the methods provided in the present disclosure is that exposing the population of solidified microgels in bulk to lysis conditions sufficient to lyse cells contained within the population of solidified microgels allows for the application of harsh (stringent) lysis conditions that may not be compatible with lysis methods that are performed in-droplet. For example, use of strong detergents (e.g., sodium dodecyl sulfate) and chemicals afforded by the methods provided herein, may destabilize water-in-oil emulsion droplets. Hence, the ability to use strong detergents and chemicals during lysis in the present methods may allow for the study of more diverse cell types. In addition, exposing the population of solidified microgels in bulk to lysis conditions allows for the efficient application of different lysis conditions, e.g., in separate steps (e.g., separated by one or more wash steps), which are designed or sufficient to lyse different cell types which may be present in the original cell population.

Fragmenting and Tagging Genomic DNA

The disclosed methods may include a step of fragmenting the genomic DNA, e.g., to a length that permits their sequencing with existing sequencing platforms, which often have limited read length. Fragmentation can be achieved in a variety of ways and can be applied to either amplified or non-amplified nucleic acid targets. For example, enzymes capable of fragmenting DNA such as Fragmentase® or other nucleases can be introduced into a microgel droplet, a solidified microgel droplet, and/or a solidified microgel as described herein and the microgel droplet, solidified microgel droplet, and/or the solidified microgel subjected to conditions sufficient for fragmentation. Suitable enzymes capable of fragmenting DNA may include, e.g., DNAse I, micrococcal nuclease, DNAse III, and any other nuclease that results in fragmented DNA, including nucleases with sequence specific catalysis. Alternatively, chemical methods can be used, such as the inclusion of acids, reactive oxygen species, etc. Organisms that degrade DNA can also be used by including them in the microgel droplet, solidified microgel droplet, and/or solidified microgel with the nucleic acids. Physical methods, such as shear generated by flow of the nucleic acids, in the microgel droplet, solidified microgel droplet, and/or solidified microgel, can also be used. Other methods can also be used that perform multiple operations on the nucleic acids including fragmentation. For example, transposons can be used to insert or attach sequences into the nucleic acids, often fragmenting them in the process.

Accordingly, in some embodiments, the fragmented genomic DNA may be size selected for DNA fragments in the 200-600 bp range. For example, the fragmented genomic DNA may be size selected in the 50-750 bp range, 75-725 bp range, 100-700 bp range, 125-675 bp range, 150-650 bp range, 175-625 bp range, or any range bound between two of the following sizes: 25 bp, 50 bp, 75 bp, 100 bp, 125 bp, 150 bp, 175 bp, 200 bp, 225 bp, 250 bp, 275 bp, 300 bp, 325 bp, 350 bp, 375 bp, 400 bp, 425 bp, 450 bp, 475 bp, 500 bp, 525 bp, 550 bp, 575 bp, 600 bp, 625 bp, 650 bp, 675 bp, 700 bp, 725 bp, 750 bp, 775 bp, 800 bp or more. Size selection of the fragmented genomic DNA can be performed by any method known in the art, for example, using agarose gel electrophoresis, solid phase reversible immobilization beads (e.g., AMPure XP beads), microfluidic instruments (e.g., Caliper Labchip XT), commercially available library construction kits (e.g., Sage Science Pippin Prep), etc. Size selection of fragmented genomic DNA may occur after fragmented genomic DNA is obtained, after the fragmented genomic DNA is tagged, or after the tagged, fragmented genomic DNA is barcoded.

Accordingly, in some embodiments, the present disclosure provides a method for sequencing single cell genomic DNA including purifying genomic DNA from cells contained within a population of solidified microgels in bulk to provide a population of solidified microgels including purified genomic DNA, and fragmenting the purified genomic DNA to provide a population of solidified microgels including fragmented genomic DNA.

In some embodiments, the population of solidified microgels including purified genomic DNA is re-encapsulated before the step of fragmenting the purified genomic DNA. Accordingly, in some embodiments the present disclosure provides a method for sequencing single cell genomic DNA including purifying genomic DNA from cells contained within a population of solidified microgels in bulk to provide a population of solidified microgels including purified genomic DNA, encapsulating the population of solidified microgels including purified genomic DNA into droplets to provide a population of purified genomic DNA-containing droplets, and fragmenting the purified genomic DNA to provide a population of fragmented genomic DNA-containing droplets.

In some embodiments, encapsulating the population of solidified microgels including purified genomic DNA into droplets to provide a population of purified genomic DNA-containing droplets includes encapsulating the solidified microgels with reagents for use in fragmentation and tagging of the purified genomic DNA. In some embodiments, fragmentation and tagging of genomic DNA occurs simultaneously, e.g., in a tagmentation step, and encapsulating the solidified microgels with reagents for use in fragmentation and tagging of the purified genomic DNA includes encapsulating the solidified microgels with tagmentation reagents, e.g., a complex including a transposase and a transposon. For example, in some embodiments, each of the members of the population of purified genomic DNA-containing droplets includes a complex including a transposase and a transposon.

In some embodiments, a method for sequencing single cell genomic DNA includes purifying genomic DNA from cells contained within a population of solidified microgels in bulk to provide a population of solidified microgels including purified genomic DNA. In some embodiments, the purified genomic DNA is subject to conditions that fragment the purified genomic DNA to provide a population of solidified microgels including fragmented genomic DNA. In some embodiments, the fragmented genomic DNA is optionally tagged with a common adapter sequence. In some embodiments, fragmentation and tagging of genomic DNA occurs simultaneously.

In some embodiments, fragmentation of genomic DNA can be achieved using Fragmentase® (NEB), Transposon Insertion (Nextera), non-specific DNA endonuclease such as DNAseI, or incorporation of modified bases during amplification and cleavage using DNA repair enzymes, such as dUTP incorporation during amplification and specific cleavage using EndoV and uracil glycosylase. Hydrodynamic shearing can also be used to fragment DNA.

In some embodiments, the method includes fragmenting the purified genomic DNA via transposon insertion, e.g., using Tn5 transposon, Mu transposon, or any other suitable transposon known in the art. In such embodiments, the method includes contacting the purified genomic DNA with a complex including a transposase and a transposon. In some embodiments, the complex includes a transposon that includes an adapter sequence. Contacting the purified genomic DNA with the complex results in fragmented genomic DNA including the adapter sequence. In certain embodiments, because of the dimeric nature of transposases, the fragmented genomic DNA remains intact as a macromolecular complex and continues to be retained within the population of solidified microgels. Accordingly, a population of solidified microgels including fragmented genomic DNA optionally including a common adapter sequence is obtained.

Accordingly, an example method of sequencing single cell genomic DNA as provided by the present disclosure includes: encapsulating a population of single cells in molten gel droplets to provide a population of molten gel droplets, wherein each molten gel droplet of the population contains zero or one cell; solidifying the population of molten gel droplets to provide a population of solidified microgel droplets; breaking the emulsions of the solidified microgel droplets to provide a population of solidified microgels; exposing the population of solidified microgels in bulk to lysis conditions sufficient to lyse cells contained within the population of solidified microgels; purifying genomic DNA from cells contained within the population of solidified microgels in bulk to provide a population of solidified microgels including purified genomic DNA; encapsulating the population of solidified microgels including purified genomic DNA into droplets to provide a population of purified genomic DNA-containing droplets; and fragmenting the purified genomic DNA within the population of purified genomic DNA-containing droplets to provide a population of fragmented genomic DNA-containing droplets.

Barcoding Fragmented Genomic DNA

The disclosed methods may include a step of barcoding a population of solidified microgels including fragmented genomic DNA optionally including a common adapter sequence. Barcoding is performed such that the fragmented genomic DNA of each individual single cell is associated with an identifying barcode sequence, e.g., a single unique barcode sequence. In some embodiments, barcoding of the fragmented genomic DNA can be performed in a single step, for example, by incorporating the barcode sequences using a transposase, or in two steps, in which barcode sequences are added to the fragmented genomic DNA with, for example, ligase or overlap extension PCR.

In some embodiments, a population of solidified microgels including fragmented genomic DNA can be merged together with a library of barcode sequences, wherein each identifying barcode sequence (or population of an identifying barcode sequence), e.g., each unique barcode sequence (or population of a unique barcode sequence) of the library of barcode sequences is separately encapsulated in a droplet. Accordingly, in some embodiments, a method of sequencing single cell genomic DNA includes encapsulating the population of solidified microgels including fragmented genomic DNA into droplets to provide a population of fragmented genomic DNA-containing droplets. The population of fragmented genomic DNA-containing droplets may then be merged with a library of barcode sequence containing droplets such that each fragmented genomic DNA-containing droplet is merged with an identifying barcode sequence (or population of an identifying barcode sequence), e.g., a unique barcode sequence (or population of a unique barcode sequence) containing droplet. The method may further include subjecting the population of droplets containing both the fragmented genomic DNA and barcode sequence to conditions sufficient for enzymatic incorporation of the barcode sequence into the fragmented genomic DNA.

One approach for incorporating a barcode sequence into fragmented genomic DNA is to use primers that are complementary to the adapter sequences and the barcode sequences, such that the product amplicons of both fragmented genomic DNA and barcodes can anneal to one another and, via an extension reaction such as DNA polymerization, be extended onto one another, generating a double stranded product including the fragmented genomic DNA attached to the barcode sequence.

Alternatively or additionally, the primers that amplify that target can themselves be barcoded so that, upon annealing and extending onto the target, the amplicon produced has the barcode sequence incorporated into it. This can be applied with a number of amplification strategies, including specific amplification with PCR or non-specific amplification with, for example, multiple displacement amplification (MDA).

An alternative or additional enzymatic reaction that can be used to attach barcodes to fragmented genomic DNA is ligation, including blunt or sticky end ligation. In this approach, the DNA barcodes are incubated with the fragmented genomic DNA and ligase enzyme, resulting in the ligation of the barcode to the targets. The ends of the fragmented genomic DNA can be modified as needed for ligation by a number of techniques, including by using adaptors introduced with ligase or fragments to enable greater control over the number of barcodes added to the end of the molecule.

Yet another approach for adding the barcodes to the fragmented genomic DNA is to introduce them directly with a transposase or with a combination of enzymes, such as a non-specific endonuclease or combination of non-specific endonucleases (e.g., Fragmentase®) and ligase. For example, in this approach, barcodes can be synthesized that are compatible with a transposase. The transposase can then fragment the purified genomic DNA and add the barcodes to the ends of the fragment molecules, performing all steps of the reaction in one reaction. A combination of Fragmentase® and ligase can also be used, wherein the Fragmentase® is used to fragment the nucleic acids to a size suitable for sequencing, and the ligase is used to attach the barcodes to the fragment ends.

Accordingly, an example method of sequencing single cell genomic DNA as provided by the present disclosure includes: encapsulating a population of single cells in molten gel droplets to provide a population of molten gel droplets, wherein each molten gel droplet of the population contains zero or one cell; solidifying the population of molten gel droplets to provide a population of solidified microgel droplets; breaking the emulsions of the solidified microgel droplets to provide a population of solidified microgels; exposing the population of solidified microgels in bulk to lysis conditions sufficient to lyse cells contained within the population of solidified microgels; purifying genomic DNA from cells contained within the population of solidified microgels in bulk to provide a population of solidified microgels including purified genomic DNA; encapsulating the population of solidified microgels including purified genomic DNA into droplets to provide a population of purified genomic DNA-containing droplets; fragmenting the purified genomic DNA within the population of purified genomic DNA-containing droplets to provide a population of fragmented genomic DNA-containing droplets DNA-containing; and barcoding the fragmented genomic DNA or an amplification product thereof in the population of fragmented genomic DNA-containing droplets to provide a population of barcoded, fragmented genomic DNA-containing droplets.

In some embodiments, upon obtaining a population of barcoded, fragmented genomic DNA-containing droplets, the emulsion including the population of droplets is broken and the barcoded, fragmented DNA is purified to provide purified, barcoded, fragmented genomic DNA. An optional size selection step may occur to select for purified, barcoded, genomic DNA fragments of a certain size that permits their sequencing with existing sequencing platforms. Additional disclosure with respect to barcoding nucleic acids in droplets is provided in International Patent Application Publication No. WO2016/126871, the disclosure of which is incorporated by reference herein.

Molecular Amplification and Barcoding Via MALBAC

As an alternative to tagmentation/fragmentation, purified single-cell genomes in hydrogels can be subjected to a MALBAC (Multiple Annealing and Looping Based Amplification Cycles) amplification reaction in droplets by co-flowing the microgels with amplification reagents in a microfluidic dropmaker.

The MALBAC reaction is described generally in Zong et al. *Genome-wide detection of single-nucleotide and copy-number variations of a single human cell*, Science, 2012, the disclosure of which is incorporated by reference herein. Briefly, in a MALBAC reaction, degenerate primers anneal to genomic DNA and extend. In cycles 2 and later, hairpin loops form after extension and denaturation. These hairpins do not participate in the later cycles of the reaction as they are in a looped conformation. Following this "quasi-linear" amplification (6-10+ cycles), PCR with a single primer is used to amplify the looped products exponentially (10+ cycles).

The product of the initial quasi-linear reaction is looped amplicons. These loops can be barcoded, either by (1) fusion with a barcoded DNA fragment or (2) directly by insertion of a barcode sequence in the MALBAC primer. Here, two novel barcoding methods are described separately for clarity.

Method 1: Fusion of Molecular Barcode in Droplets by SOE-PCR

The MALBAC reaction uses a single primer (from Zong et al. 2012):

```
                                              (SEQ ID NO: 1)
5'-GTGAGTGATGGTTGAGGTAGTGTGGAGNNNNNNNN-3'
        27 bp handle                  8N
```

The representative primer has a 27 bp handle and 8 degenerate bases, but other variants are possible.

The droplets containing purified DNA in microgels and MALBAC amplification mix are then thermal cycled, e.g., according to the following protocol:

```
95 - 5 min
20 - 50 sec ⎫
30 - 50 sec ⎪
40 - 45 sec ⎪
50 - 45 sec ⎬  8 CYCLES
65 - 4 min  ⎪
95 - 20 sec ⎪
58 - 20 sec ⎭
4 - hold
```

The amplicons in the droplets have the following structure. Note that the loop is single-stranded, while the 27 bp handle region is double-stranded:

```
5'-GTGAGTGATGGTTGAGGTAGTGTGGAG (SEQ ID NO: 2)-Loop

3'-CTCCACACTACCTCAACCATCACTCAC (SEQ ID NO: 3)-Loop
```

Separately, barcodes are made via digital PCR in microdroplets (e.g., as described herein). The double-stranded barcodes can have the following general structure:

```
5'-PCR_HANDLE -15N -GAT -3'

3'-PCR_HANDLE*-15N*-GAT*-5'
```

The PCR reaction may be asymmetric to favor production of the upper single strand by using an excess of PCR HANDLE primer (e.g., in a 1 to 5, 10, 20, etc. ratio compared to the limiting primer). The PCR HANDLE primer may also be functionalized with biotin (or other biomolecule) to facilitate downstream capture of barcoded DNA fragments using streptavidin-coated beads.

Figure 17:
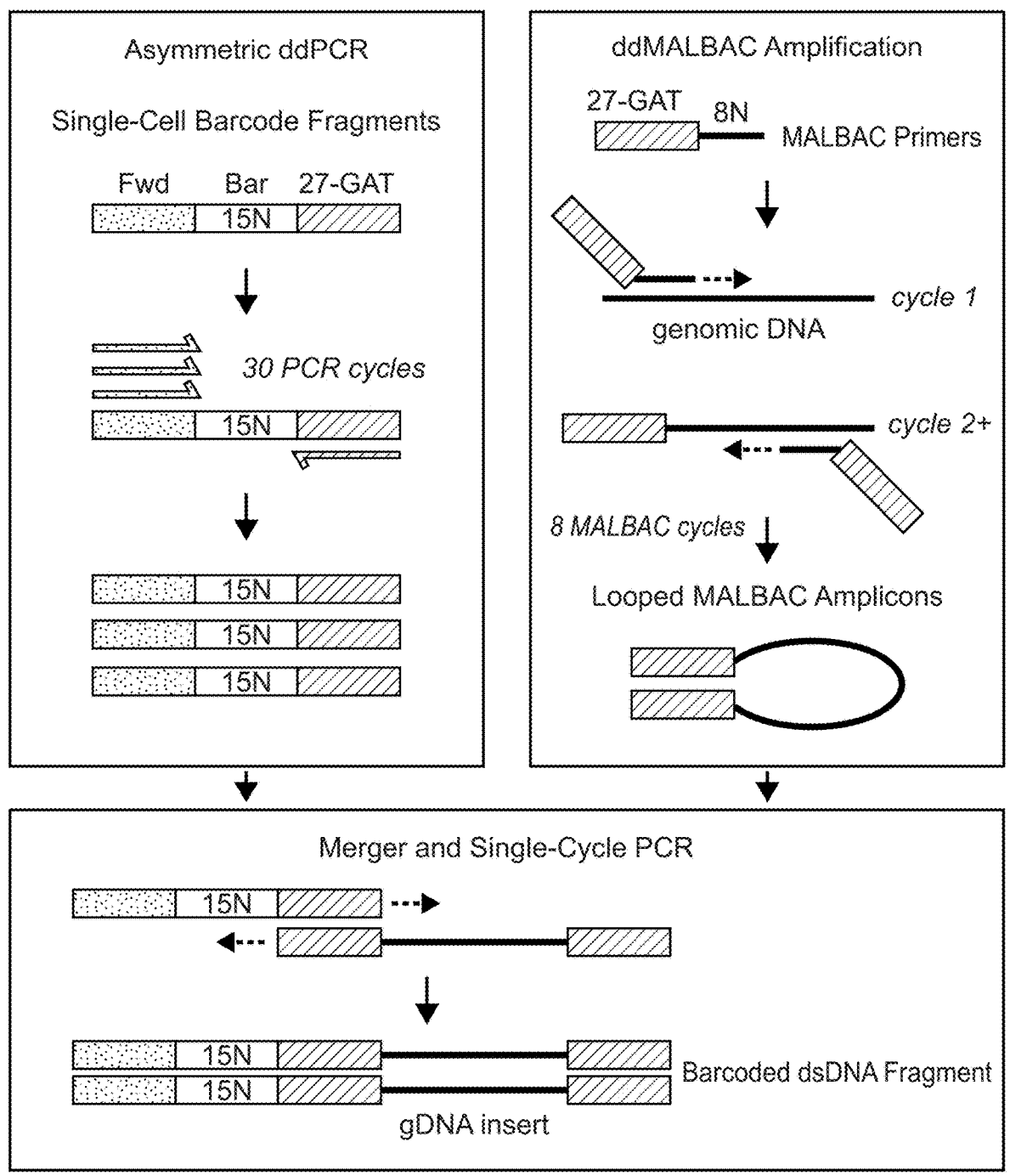
FIG. 17 provides a schematic depicting a workflow for barcoding genomic DNA using asymmetric digital droplet PCR barcodes fused to MALBAC amplicons using a single-cycle extension.
Figure 18:
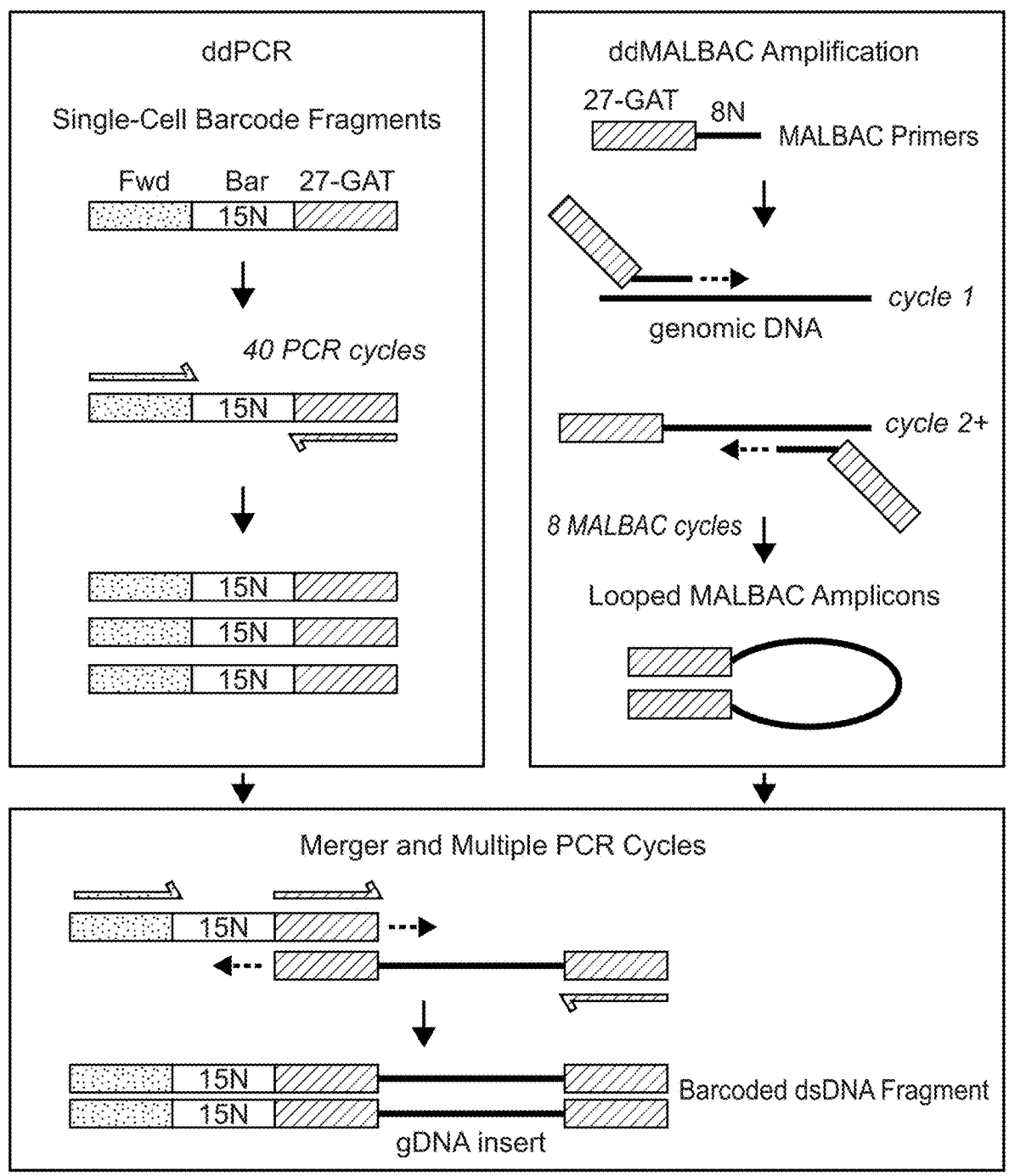
FIG. 18 provides a schematic depicting a workflow for barcoding genomic DNA using symmetric digital droplet PCR barcodes fused to MALBAC amplicons using an overlap extension followed by multiple rounds of PCR.

The digital barcode droplets are microfluidically merged, e.g., in a 1:1 ratio, with the droplets containing the single-cell MALBAC amplicons. A single cycle of PCR is used to anneal and extend the barcode fragments onto the MALBAC amplicons using their complementary overlapping regions (FIG. 17). Alternatively, multiple PCR cycles can be performed and the barcoded genomic DNA amplified in droplets using primers situated at the 5' ends of the barcoded strands (FIG. 18). In this variant, leftover MALBAC primers can be digested with a single-stranded exonuclease (e.g. Exonuclease I or similar). Primers for PCR amplification can be modified (e.g. via 3' phosphorothioate bonds or similar) to protect against degradation by the exonuclease.

Example PCR protocol for single-cycle extension:

```
95 - 1 min
63 - 50 sec
72 - 5 min
12 - hold
```

Example PCR protocol for extension and exponential amplification:

```
95 - 1 min
95 - 20 sec ⎫
55 - 30 sec ⎬  30 cycles
72 - 3 min  ⎭
72 - 5 min
12 - hold
```

Droplets are broken and the barcoded fragments are enriched via PCR (in the case of single-cycle extension in droplets). Size-selection using, e.g., SPRI beads, gel electrophoresis, etc., is used to remove single-stranded DNA barcodes and primer dimers from the amplified product.

Downstream library preparation for next-generation sequencing can then proceed according to the specifications by the sequencing platform. For Illumina sequencing-by-synthesis (SBS) chemistry, the barcoded dsDNA is fragmented (enzymatically, mechanically, etc.), adapters are added (by ligation, Tn5 [Nextera] transposition, etc.), and the library is amplified by PCR and sequenced.

Method 2: Direct Barcoding of MALBAC Primers

The barcoded MALBAC reaction uses a library of primers (modified from Zong et al. 2012):

```
                                              (SEQ ID NO: 4)
5'-GTGAGTGATGGTTGAGGTAGTGTGGAG[BARCODE]NNNNNNNN-3'
        27 bp handle                            8N
```

Figure 19:
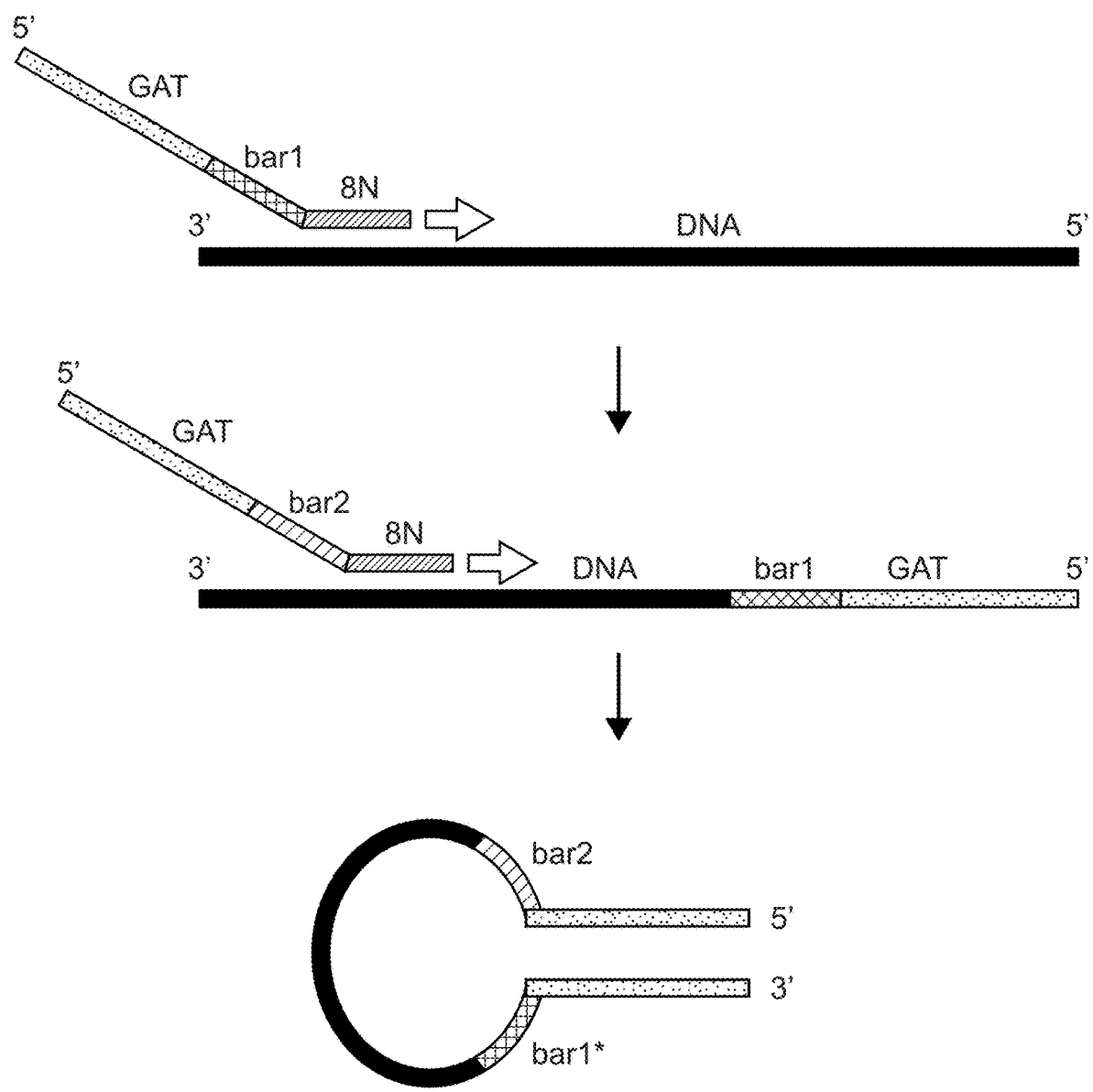
FIG. 19 provides a schematic depicting a molecular barcoding scheme employing barcoded MALBAC primers producing a combinatorically-barcoded looped amplicon.

The predefined barcode oligonucleotides (4-12+bp barcode region) are emulsified in droplets to generate a library of microdroplets each containing micromolar-scale concentrations of a single primer variant. When looped as MALBAC amplicons, the primers form a combinatorically barcoded construct (FIG. 19).

Figure 20:
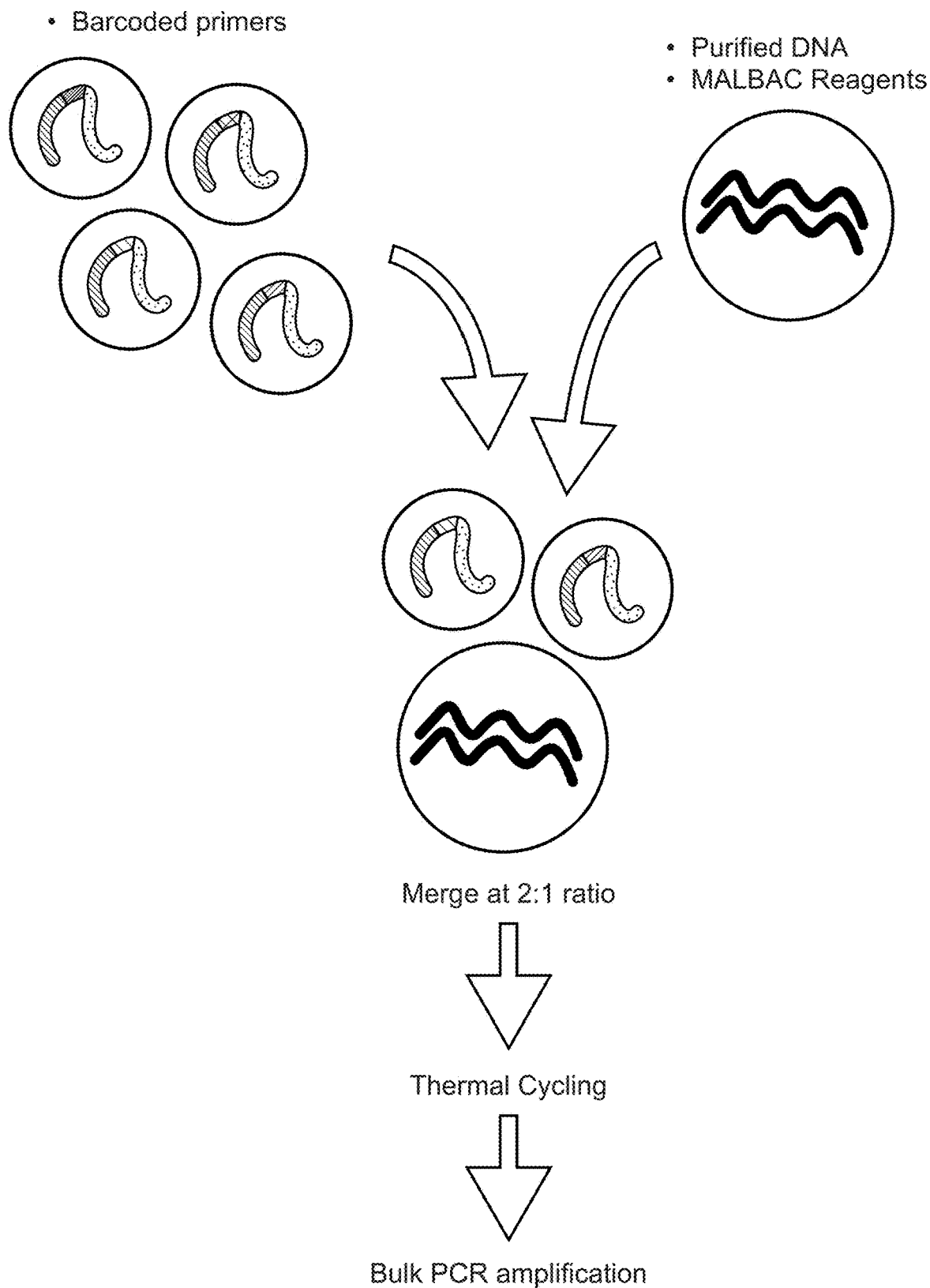
FIG. 20 provides a schematic depicting a microfluidic workflow for generating combinatorically barcoded genomic DNA amplicons.

The purified DNA in a microgel is then merged microfluidically with MALBAC amplification reagent and two primer-containing droplets (FIG. 20). The MALBAC reaction is performed with a thermal cycling protocol identical to Method 1. The resulting looped amplicons have the following structure:

[BARCODE1]-Loop
5'-GTGAGTGATGGTTGAGGTAGTGTGGAG-(SEQ ID NO: 2)

3'-CTCCACACTACCTCAACCATCACTCAC-(SEQ ID NO: 3)
[BARCODE2]-Loop

Barcode sequences 1 and 2 form a unique combinatorial identifier for the MALBAC loop.

After thermal cycling in droplets, the emulsions are broken and PCR is carried out to amplify the barcodes amplicons and create a double-stranded barcoded DNA library. The primers used for exponential amplification may also contain barcodes for sample multiplexing.

Preparation for NGS depends on the platform. However, because the barcodes are combinatorial and located at both the 5' and 3' ends of the construct, the dsDNA fragments cannot be fragmented during the library preparation steps.

Generating a Database of Single Cell Genome Sequencing Reads

The methods described herein may include a step of sequencing the purified, barcoded, fragmented genomic DNA. DNA sequence can be achieved with commercially available next generation sequencing (NGS) platforms, including platforms that perform sequencing by synthesis, sequencing by ligation, pyrosequencing, using reversible terminator chemistry, using phospholinked fluorescent nucleotides, or real-time sequencing. For example, the purified, barcoded, fragmented genomic DNA may be sequenced on an Illumina MiSeq platform using a custom index primer.

Accordingly, an example method of sequencing single cell genomic DNA as provided by the present disclosure includes: encapsulating a population of single cells in molten gel droplets to provide a population of molten gel droplets, wherein each molten gel droplet of the population contains zero or one cell; solidifying the population of molten gel droplets to provide a population of solidified microgel droplets; breaking the emulsions of the solidified microgel droplets to provide a population of solidified microgels; exposing the population of solidified microgels in bulk to lysis conditions sufficient to lyse cells contained within the population of solidified microgels; purifying genomic DNA from cells contained within the population of solidified microgels in bulk to provide a population of solidified microgels including purified genomic DNA; encapsulating the population of solidified microgels including purified genomic DNA into droplets to provide a population of purified genomic DNA-containing droplets; and fragmenting the purified genomic DNA within the population of purified genomic DNA-containing droplets to provide a population of fragmented genomic DNA-containing droplets; barcoding the fragmented genomic DNA or an amplification product thereof in the population of fragmented genomic DNA-containing droplets to provide a population of barcoded, fragmented genomic DNA-containing droplets; purifying barcoded, fragmented genomic DNA from the barcoded, fragmented genomic DNA-containing droplets to provide purified, barcoded, fragmented genomic DNA; and sequencing the purified, barcoded fragmented genomic DNA.

Raw sequencing reads obtained from the commercial NGS platform can be filtered by quality and grouped by barcode sequence using any suitable scripts known in the art, e.g., Python script barcodeCleanup.py. In some embodiments, a given sequencing read may be discarded if more than about 20% of its bases have a quality score (Q-score) less than Q20, indicating a base call accuracy of about 99%. In some embodiments, a given sequencing read may be discarded if more than about 5%, about 10%, about 15%, about 20%, about 25%, about 30% have a Q-score less than Q10, Q20, Q30, Q40, Q50, Q60, or more, indicating a base call accuracy of about 90%, about 99%, about 99.9%, about 99.99%, about 99.999%, about 99.9999%, or more, respectively.

In some embodiments, all sequencing reads associated with a barcode containing less than 50 reads may be discarded to ensure that all barcode groups, representing single cells, contain a sufficient number of high-quality reads. In some embodiments, all sequencing reads associated with a barcode containing less than 30, less than 40, less than 50, less than 60, less than 70, less than 80, less than 90, less than 100 or more may be discarded to ensure the quality of the barcode groups representing single cells.

Once the raw sequencing reads are filtered by quality and grouped by barcode sequence, the sequences may be exported to a table, e.g., a table in a relational database, e.g., a SQLite database, including fields pertinent to identifying sequencing reads that are obtained from a single cell. In some embodiments, the sequences may be exported to a table in a relational database, e.g., a SQLite database including fields containing the barcode sequence, barcode group size, a unique read ID number, and read sequence. In some embodiments, e.g., in the case of analyzing a synthetic cell population (see, Experimental section), sequencing reads may be aligned using any suitable available software program, e.g., bowtie2 v2.2.9, and the SQLite table may be updated with relevant alignment information for each sequencing read. In some embodiments, e.g., when analyzing environmental samples (see, Experimental section), the sequencing reads may be classified by taxonomy using any suitable available software program, e.g., Kraken v0.10.5, and the SQLite table may be updated with relevant taxonomic information for each sequencing read. In some embodiments, barcode group purity may be calculated from reference alignment data or phylogenetic labels using any suitable available script, e.g. Python script purity.py.

Utility

The present disclosure provides methods for sequencing single cell genomic DNA from a population of single cells. Methods provided herein may find use in copy number variant analysis for cancer. For example, in cancer, cells undergo rapid evolution that leads to massive mutation of their genomes. One form of mutation is copy number variation, in which different parts of the genome are duplicated or erased. In some embodiments, methods provided herein allows for the counting of known sequences across the genome. An advantage of using a method provided herein is that copy number variant analysis can be performed with low coverage of the genome, often less than 1%, allowing it to be measured without having to perform large amounts of sequencing.

In some embodiments, methods provided herein may find use in blood sequencing, wherein blood sequencing includes sequencing all cells of interest in a blood sample (e.g., immune cells). For example, a blood sample may be collected and the relevant cell types extracted. Immune cells sample the circulatory system, and as such, their biological state may be representative of disease, e.g., infection, sepsis, cancer, autoimmune disorders, etc. In some embodiments, sequencing the nucleic acids of immune cells from a blood sample may allow detection of a variety of diseased states. In some embodiments, rare cells such as circulating tumor cells and circulating fetal cells may be detected using the methods provided herein. In some embodiments, while the majority of sequenced cells from a blood sample containing circulating tumor and/or fetal cells will not correspond to the cell population of interest, when any such circulating tumor and/or fetal cell is identified, complete information about its genome may be recovered.

In some embodiments, methods provided herein may find use in the field of metagenomics. For example, methods provided herein may find use in studying diverse microbial systems, wherein their analysis may be valuable in identifying rare system members and allowing them to be recovered for detailed study, e.g., to recover their nucleic acid sequences.

In some embodiments, methods provided herein may find use in studying latent human immunodeficiency virus (HIV) infection. Using methods as described herein, cells from an infected individual may be sorted based on the presence of HIV genes. Sorted cells may be sequenced to recover information about how their genome may be modulated by the virus. Those of skill in the art will be able to envision the power of using the methods described herein and will be able to adapt the methods for use in any application.

While the methods provided herein have been described primarily with respect to cellular genomic DNA, it should be noted that the SiC-seq method also provides a means to isolate and barcode large DNA molecules, irrespective of the entity from which they originate. While the described methods have focused on cells, similar approaches can be applied to viruses whose genomes can be trapped and processed within the gel matrix.

Thus, for example, in some embodiments the present disclosure provides a method of sequencing genomic DNA, e.g., viral genomic DNA, the method including encapsulating a population of biological entities, e.g., viruses, in molten gel droplets to provide a population of molten gel droplets, wherein each molten gel droplet of the population contains zero or one biological entity; solidifying the population of molten gel droplets to provide a population of solidified microgel droplets; breaking the emulsions of the solidified microgel droplets to provide a population of solidified microgels; exposing the population of solidified microgels in bulk to lysis conditions sufficient to lyse biological entities contained within the population of solidified microgels; purifying genomic DNA from biological entities contained within the population of solidified microgels in bulk to provide a population of solidified microgels comprising purified genomic DNA; encapsulating the population of solidified microgels comprising purified genomic DNA into droplets to provide a population of purified genomic DNA-containing droplets; fragmenting the purified genomic DNA within the population of purified genomic DNA-containing droplets to provide a population of fragmented genomic DNA-containing droplets; barcoding the fragmented genomic DNA or an amplification product thereof in the population of fragmented genomic DNA-containing droplets to provide a population of barcoded, fragmented genomic DNA-containing droplets; purifying barcoded, fragmented genomic DNA from the barcoded, fragmented genomic DNA-containing droplets to provide purified, barcoded, fragmented genomic DNA; and sequencing the purified, barcoded, fragmented genomic DNA. Similarly, it should be understood that each of the non-limiting aspects of the disclosure numbered 1-36 as provided below may be modified to refer to a suitable biological entity, e.g., a virus, rather than a cell.

Each of the methods described herein may be modified as appropriate for use with non-cell based biological entities or large DNA molecules.

Devices and Systems

As indicated above, embodiments of the disclosed subject matter employ systems and/or devices including microfluidic devices. Devices of the subject disclosure include all those described above in association with the subject methods. Microfluidic devices of this disclosure may be characterized in various ways.

In some aspects, for example, microfluidic systems and/or devices are provided which include one or more droplet makers, configured to generate droplets, as described herein, and/or one or more flow channels. In some aspects, the one or more flow channels are operably connected, e.g., fluidically connected, to the one or more droplet makers and/or are configured to receive one or more droplets therefrom. By "operably connected" and "operably coupled", as used herein, is meant connected in a specific way (e.g., in a manner allowing fluid, e.g., water, to move and/or electric power to be transmitted) that allows a disclosed system or device and its various components to operate effectively in the manner described herein.

As noted above, microfluidic devices may include one or more flow channels, e.g., flow channels which droplets may pass into, out of, and/or through. In certain embodiments, flow channels are one or more "micro" channel. Such channels may have at least one cross-sectional dimension on the order of a millimeter or smaller (e.g., less than or equal to about 1 millimeter). For certain applications, this dimension may be adjusted; in some embodiments the at least one cross-sectional dimension is about 500 micrometers or less. In some embodiments, the cross-sectional dimension is about 100 micrometers or less, or about 10 micrometers or less, and sometimes about 1 micrometer or less. A cross-sectional dimension is one that is generally perpendicular to the direction of centerline flow, although it should be understood that when encountering flow through elbows or other features that tend to change flow direction, the cross-sectional dimension in play need not be strictly perpendicular to flow. It should also be understood that in some embodiments, a micro-channel may have two or more cross-sectional dimensions such as the height and width of a rectangular cross-section or the major and minor axes of an elliptical cross-section. Either of these dimensions may be compared against sizes presented here. Note that microchannels employed in this disclosure may have two dimensions that are grossly disproportionate—e.g., a rectangular cross-section having a height of about 100-200 micrometers and a width on the order or a centimeter or more. Of course, certain devices may employ channels in which the two or more axes are very similar or even identical in size (e.g., channels having a square or circular cross-section).

Microfluidic devices, in some embodiments of this disclosure, are fabricated using microfabrication technology. Such technology may be employed to fabricate integrated circuits (ICs), microelectromechanical devices (MEMS), display devices, and the like. Among the types of microfabrication processes that can be employed to produce small dimension patterns in microfluidic device fabrication are photolithography (including X-ray lithography, e-beam lithography, etc.), self-aligned deposition and etching technologies, anisotropic deposition and etching processes, self-assembling mask formation (e.g., forming layers of hydrophobic-hydrophilic copolymers), etc.

In view of the above, it should be understood that some of the principles and design features described herein can be scaled to larger devices and systems including devices and systems employing channels reaching the millimeter or even centimeter scale channel cross-sections. Thus, when describing some devices and systems as "microfluidic," it is intended that the description apply equally, in certain embodiments, to some larger scale devices.

When referring to a microfluidic "device" it is generally intended to represent a single entity in which one or more channels, reservoirs, stations, etc. share a continuous substrate, which may or may not be monolithic. Aspects of microfluidic devices include the presence of one or more fluid flow paths, e.g., channels, having dimensions as discussed herein. A microfluidics "system" may include one or more microfluidic devices and associated fluidic connections, electrical connections, control/logic features, etc.

Systems may also include one or more of: (a) a temperature control module for controlling the temperature of one or more portions of the subject devices and/or droplets therein and which is operably connected to the microfluidic device(s), (b) a detection means, i.e., a detector, e.g., an optical imager, operably connected to the microfluidic device(s), (c) an incubator, e.g., a cell incubator, operably connected to the microfluidic device(s), and (d) a sequencer operably connected to the microfluidic device(s). The subject systems may also include one or more conveyor configured to move, e.g., convey, a substrate from a first droplet, receiving position to one or more of (a)-(d).

The subject devices and systems, include one or more sorter for sorting droplets, into one or more flow channels. Such a sorter may sort and distribute droplets, based on one or more characteristics of the droplets including composition, size, shape, buoyancy, or other characteristics.

Aspects of the devices also include one or more detection means i.e., a detector, e.g., an optical imager, configured for detecting the presence of one or more droplets, or one or more characteristics thereof, including their composition. In some embodiments, detection means are configured to recognize one or more components of one or more droplets, in one or more flow channel.

In various embodiments, microfluidic devices of this disclosure provide a continuous flow of a fluid medium. Fluid flowing through a channel in a microfluidic device exhibits many unique properties. Typically, the dimensionless Reynolds number is extremely low, resulting in flow that always remains laminar. Further, in this regime, two fluids joining will not easily mix, and diffusion alone may drive the mixing of two compounds.

In addition, the subject devices, in some embodiments, include one or more temperature and/or pressure control module. Such a module may be capable of modulating temperature and/or pressure of a carrier fluid in one or more flow channels of a device. More specifically, a temperature control module may be one or more thermal cycler.

An exemplary embodiment is described with reference to FIG. 1, Panels A, B and C, which depict schematics of microfluidic devices that may be used to a) generate barcode droplets and encapsulate cells in microgels (e.g., agarose microgels), b) re-encapsulate microgels with fragmenting and/or tagging reagents, e.g., tagmentation reagents, and c) merge microgel droplets with barcode droplets and PCR droplets. As shown in FIG. 1, Panel A, single cells are packaged into molten gel droplets and are encapsulated and spaced by a carrier fluid, e.g., oil to provide encapsulated single cells. Molten gel droplet formation may be slow, due to the viscosity of the mix and interfacial tension properties. To speed the formation of molten gel droplets, bubble triggering may be used (Abate, A. R., and Weitz, D. A., *Lab Chip*, 11(10): 1713-1716, 2011), the disclosure of which is incorporated by reference herein. In some embodiments, molten gel solution and cells are co-flowed into a droplet generator under jetting flow conditions. Oil is also introduced under jetting flow conditions such that a jet is formed of aqueous phase in oil. Bubble triggering introduces air bubbles near the jet, either by injecting as air bubbles, or by injecting an air-stream alongside the jet. In some cases, the air bubbles perturb the jet, causing it to break into droplets. If air bubbles are periodically spaced, droplets will form between the air bubbles of a uniform size, increasing the rate of monodisperse droplet generation.

Accordingly, in some embodiments, the present disclosure provides a system including a microfluidic device, a molten gel reservoir and a heating element, the microfluidic device including a co-flow droplet maker including: a first input channel configured to provide a plurality of cells to a flow channel; a second input channel configured to provide a molten gel flow to the flow channel from the gel reservoir, wherein the heating element is positioned in proximity to the gel reservoir and configured to apply heat to the gel reservoir sufficient to maintain a molten gel in the molten gel reservoir in a molten state; and a third input channel and a fourth input channel positioned on opposite sides of the flow channel and downstream of the first and second input channels, wherein the third and fourth input channels are configured to provide immiscible phase fluid flows to the flow channel.

Now referring to FIG. 1, Panel B, a device that may be of use to carry out the methods of the present disclosure includes a microfluidic device for re-encapsulating microgels with fragmenting and/or tagging reagents, e.g., tagmentation reagents. As shown in FIG. 1, Panel B, microgels are combined with fragmenting and/or tagging reagents, e.g., tagmentation reagents, and are encapsulated and spaced by a carrier fluid, e.g., oil to provide encapsulated single cells. Now referring to FIG. 1, Panel C, a device that may be of use to carry out the methods of the present disclosure that may further include reservoirs for incorporating reagents (e.g., PCR reagents, cell lysis reagents, etc.) and for incorporating barcode nucleic acid sequences is provided, in which liquid electrodes, moats, droplet mergers and the reservoirs for the spacing carrier fluid, e.g., oil, barcode droplets, and PCR droplets are identified.

Accordingly, in some embodiments, the present disclosure provides a device including components for (a) introducing two or more populations of droplets into a flow channel, (i) wherein the flow channel includes a droplet merger section associated with one or more electrodes or one or more portions of one or more electrodes configured to apply an electric field in the droplet merger section of the flow channel, (ii) wherein the two or more populations of droplets are introduced into the flow channel at a single junction from two or more separate inlet channels, respectively, and (iii) wherein the two or more populations of droplets are introduced into the flow channel such that the droplet inputs from each inlet channel at least partially synchronize due to hydrodynamic effects, resulting in the ejection of spaced groups of droplets, in which at least some of the spaced groups of droplets include a droplet from each of the two or more populations of droplets; (b) flowing the spaced groups of droplets into the droplet merger section; and (c) merging droplets within a spaced group by applying an electric field in the droplet merger section of the flow channel using the one or more electrodes or the one or more portions of the one or more electrodes.

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects (Set A and Set B) of the disclosure are provided below. As will be apparent to those of ordinary skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Set A

1. A method of sequencing single cell genomic DNA, the method comprising:
   encapsulating a population of single cells in molten gel droplets to provide a population of molten gel droplets, wherein each molten gel droplet of the population contains zero or one cell;
   solidifying the population of molten gel droplets to provide a population of solidified microgel droplets;
   breaking the emulsions of the solidified microgel droplets to provide a population of solidified microgels;
   exposing the population of solidified microgels in bulk to lysis conditions sufficient to lyse cells contained within the population of solidified microgels;
   purifying genomic DNA from cells contained within the population of solidified microgels in bulk to provide a population of solidified microgels comprising purified genomic DNA;
   encapsulating the population of solidified microgels comprising purified genomic DNA into droplets to provide a population of purified genomic DNA-containing droplets;
   fragmenting the purified genomic DNA within the population of purified genomic DNA-containing droplets to provide a population of fragmented genomic DNA-containing droplets;
   barcoding the fragmented genomic DNA or an amplification product thereof in the population of fragmented genomic DNA-containing droplets to provide a population of barcoded, fragmented genomic DNA-containing droplets;
   purifying barcoded, fragmented genomic DNA from the barcoded, fragmented genomic DNA-containing droplets to provide purified, barcoded, fragmented genomic DNA; and
   sequencing the purified, barcoded, fragmented genomic DNA.
2. The method of 1, wherein the barcoding comprises merging each of the fragmented genomic DNA-containing droplets with a barcode containing droplet.
3. The method of 2, wherein each of the barcode containing droplets comprises a unique nucleic acid barcode sequence.
4. The method of any one of 1 to 3, wherein the method comprises incorporating an adaptor nucleic acid sequence into the fragmented genomic DNA.
5. The method of any one of 1 to 4, wherein the population of single cells comprises eukaryotic cells.
6. The method of 5, wherein the population of single cells comprises mammalian cells.
7. The method of any one of 1 to 4, wherein the population of single cells comprises bacterial cells.
8. The method of any one of 1 to 5, wherein the population of single cells comprises fungal cells.
9. The method of any one of 1 to 8, wherein the molten gel droplet comprises a hydrogel polymer.
10. The method of 9, wherein the hydrogel polymer comprises a thermoresponsive polymer.
11. The method of 10, wherein the thermoresponsive polymer is agarose.
12. The method of any one of 1 to 11, wherein the solidifying comprises cooling the population of molten gel droplets.
13. The method of any one of 1 to 9, wherein the molten gel droplet comprises polyethylene glycol (PEG).
14. The method of 13, wherein the solidifying comprises chemically crosslinking the PEG.
15. The method of 13, wherein the solidifying comprises photo-crosslinking the PEG.
16. The method of any one of 1 to 9, wherein the molten gel droplet comprises acrylamide.
17. The method of 16, wherein the solidifying comprises chemically crosslinking the acrylamide.
18. The method of 16, wherein the solidifying comprises photo-crosslinking the acrylamide.
19. The method of any one of 1 to 9, wherein the molten gel droplet comprises alginate.
20. The method of 19, wherein the solidifying comprises adding calcium to the molten gel droplet.
21. The method of any one of 1 to 20, wherein the solidified microgels comprise pores sized to retain genomic DNA within the solidified microgels.
22. The method of any one of 1 to 21, wherein the step of encapsulating the population of single cells in molten gel droplets comprises the addition of an oil.
23. The method of any one of 1 to 22, wherein the exposing comprises contacting the population of solidified microgels in bulk with a lytic enzyme to lyse cells contained within the population of solidified microgels.
24. The method of 23, wherein the lytic enzyme is selected from zymolyase, lysostaphin, mutanolysin, lysozyme, or a combination thereof
25. The method of any one of 1 to 24, wherein the step of purifying genomic DNA from cells contained within the population of solidified microgels comprises contacting the population of solidified microgels with a detergent to solubilize cellular material contained within the population of solidified microgels.
26. The method of 25, wherein the detergent is selected from lithium dodecyl sulfate, sodium dodecyl sulfate, or a combination thereof.
27. The method of any one of 1 to 26, wherein the step of purifying genomic DNA from cells contained within the population of solidified microgels comprises contacting the population of solidified microgels with a protease to digest cellular proteins contained within the population of solidified microgels.
28. The method of 27, wherein the protease is proteinase K.
29. The method of any one of 1 to 28, wherein the step of purifying genomic DNA from cells contained within the population of solidified microgels comprises a step of washing the population of solidified microgels, wherein the step of washing the population of solidified microgels comprises contacting the population of solidified microgels with a washing buffer.
30. The method of any one of 1 to 29, wherein each of the population of purified genomic DNA-containing droplets comprise a complex comprising a transposase and a transposon.
31. The method of any one of 1 to 30, wherein the step of fragmenting comprises contacting the purified genomic DNA with a complex comprising a transposase and a transposon.
32. The method of 31, wherein the complex comprises a transposon that comprises an adapter sequence.

33. The method of 32, wherein contacting the purified nucleic acids with the complex provides fragmented genomic DNA comprising the adapter sequence.
34. The method of any one of 1 to 33, wherein the step of encapsulating a population of single cells in molten gel droplets and the step of barcoding the fragmented genomic DNA or an amplification product thereof are performed using a microfluidic device.
35. The method of any one of 1 to 34, wherein one or more of the steps of
    solidifying the population of molten gel droplets to provide a population of solidified microgel droplets;
    breaking the emulsions of the solidified microgel droplets to provide a population of solidified microgels;
    exposing the population of solidified microgels in bulk to lysis conditions sufficient to lyse cells contained within the population of solidified microgels;
    purifying genomic DNA from cells contained within the population of solidified microgels in bulk to provide a population of solidified microgels comprising purified genomic DNA; and
    fragmenting the purified genomic DNA within the population of solidified microgels comprising purified genomic DNA in bulk to provide a population of solidified microgels comprising fragmented genomic DNA, are not performed using a microfluidic device.
36. The method of any one of 1 to 35, wherein the population of single cells is a heterogeneous population of single celled microorganisms.
37. A system comprising a microfluidic device, a molten gel reservoir and a heating element, the microfluidic device comprising a co-flow droplet maker comprising
    a first input channel configured to provide a plurality of cells to a flow channel,
    a second input channel configured to provide a molten gel flow to the flow channel from the gel reservoir, wherein the heating element is positioned in proximity to the gel reservoir and configured to apply heat to the gel reservoir sufficient to maintain a molten gel in the molten gel reservoir in a molten state, and
    a third input channel and a fourth input channel positioned on opposite sides of the flow channel and downstream of the first and second input channels, wherein the third and fourth input channels are configured to provide immiscible phase fluid flows to the flow channel.

Set B
1. A method of sequencing single cell genomic DNA, the method comprising:
    encapsulating a population of single cells in molten gel droplets to provide a population of molten gel droplets, wherein each molten gel droplet of the population contains zero or one cell;
    solidifying the population of molten gel droplets to provide a population of solidified microgel droplets;
    breaking the emulsions of the solidified microgel droplets to provide a population of solidified microgels;
    exposing the population of solidified microgels in bulk to lysis conditions sufficient to lyse cells contained within the population of solidified microgels;
    purifying genomic DNA from cells contained within the population of solidified microgels in bulk to provide a population of solidified microgels comprising purified genomic DNA;
    encapsulating the population of solidified microgels comprising purified genomic DNA into droplets to provide a population of purified genomic DNA-containing droplets;
    barcoding the genomic DNA or one or more amplification products thereof to provide a population of barcoded, genomic DNA-containing droplets;
    purifying barcoded, genomic DNA from the barcoded, genomic DNA-containing droplets to provide purified, barcoded, genomic DNA; and
    sequencing the purified, barcoded, genomic DNA.
2. The method of 1, wherein the barcoding comprises merging each of the purified genomic DNA-containing droplets with a barcode containing droplet.
3. The method of 2, wherein each of the barcode containing droplets comprises a unique nucleic acid barcode sequence.
4. The method of any one of 1 to 3, comprising performing a MALBAC amplification reaction in the purified genomic DNA-containing droplets, e.g., as described herein with regard to molecular amplification and barcoding via MALBAC.
5. The method of any one of 1 to 4, wherein the population of single cells comprises eukaryotic cells.
6. The method of 5, wherein the population of single cells comprises mammalian cells.
7. The method of any one of 1 to 4, wherein the population of single cells comprises bacterial cells.
8. The method of any one of 1 to 5, wherein the population of single cells comprises fungal cells.
9. The method of any one of 1 to 8, wherein the molten gel droplet comprises a hydrogel polymer.
10. The method of 9, wherein the hydrogel polymer comprises a thermoresponsive polymer.
11. The method of 10, wherein the thermoresponsive polymer is agarose.
12. The method of any one of 1 to 11, wherein the solidifying comprises cooling the population of molten gel droplets.
13. The method of any one of 1 to 9, wherein the molten gel droplet comprises polyethylene glycol (PEG).
14. The method of 13, wherein the solidifying comprises chemically crosslinking the PEG.
15. The method of 13, wherein the solidifying comprises photo-crosslinking the PEG.
16. The method of any one of 1 to 9, wherein the molten gel droplet comprises acrylamide.
17. The method of 16, wherein the solidifying comprises chemically crosslinking the acrylamide.
18. The method of 16, wherein the solidifying comprises photo-crosslinking the acrylamide.
19. The method of any one of 1 to 9, wherein the molten gel droplet comprises alginate.
20. The method of 19, wherein the solidifying comprises adding calcium to the molten gel droplet.
21. The method of any one of 1 to 20, wherein the solidified microgels comprise pores sized to retain genomic DNA within the solidified microgels.
22. The method of any one of 1 to 21, wherein the step of encapsulating the population of single cells in molten gel droplets comprises the addition of an oil.
23. The method of any one of 1 to 22, wherein the exposing comprises contacting the population of solidified microgels in bulk with a lytic enzyme to lyse cells contained within the population of solidified microgels.

24. The method of 23, wherein the lytic enzyme is selected from zymolyase, lysostaphin, mutanolysin, lysozyme, or a combination thereof.

25. The method of any one of 1 to 24, wherein the step of purifying genomic DNA from cells contained within the population of solidified microgels comprises contacting the population of solidified microgels with a detergent to solubilize cellular material contained within the population of solidified microgels.

26. The method of 25, wherein the detergent is selected from lithium dodecyl sulfate, sodium dodecyl sulfate, or a combination thereof 27. The method of any one of 1 to 26, wherein the step of purifying genomic DNA from cells contained within the population of solidified microgels comprises contacting the population of solidified microgels with a protease to digest cellular proteins contained within the population of solidified microgels.

28. The method of 27, wherein the protease is proteinase K.

29. The method of any one of 1 to 28, wherein the step of purifying genomic DNA from cells contained within the population of solidified microgels comprises a step of washing the population of solidified microgels, wherein the step of washing the population of solidified microgels comprises contacting the population of solidified microgels with a washing buffer.

30. The method of any one of 1 to 29, wherein the step of encapsulating a population of single cells in molten gel droplets and the step of barcoding the fragmented genomic DNA or an amplification product thereof are performed using a microfluidic device.

31. The method of any one of 1 to 30, wherein one or more of the steps of solidifying the population of molten gel droplets to provide a population of solidified microgel droplets;
    breaking the emulsions of the solidified microgel droplets to provide a population of solidified microgels;
    exposing the population of solidified microgels in bulk to lysis conditions sufficient to lyse cells contained within the population of solidified microgels; and
    purifying genomic DNA from cells contained within the population of solidified microgels in bulk to provide a population of solidified microgels comprising purified genomic DNA, are not performed using a microfluidic device.

32. The method of any one of 1 to 31, wherein the population of single cells is a heterogeneous population of single celled microorganisms.

It will be apparent to one of ordinary skill in the art that various changes and modifications can be made without departing from the spirit or scope of the invention.

EXAMPLES

The following examples are put forth so as to provide those of ordinary skill in the art with a complete disclosure and description of how to make and use the present invention, and are not intended to limit the scope of the invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

Example 1: Ultrahigh-Throughput Single Cell Genome Sequencing with Droplet Microfluidic Barcoding The present disclosure provides ultrahigh-throughput single cell genomic sequencing (SiC-seq), a droplet microfluidic method capable of sequencing >50,000 single cell genomes per run. The method is validated by sequencing an artificial population of microbes containing known species at controlled proportions, obtaining ~0.1% average coverage per cell, uniform genomic sampling, and accurate estimates of species proportion. Moreover, SiC-seq generates a metagenomic database in which reads are grouped by single cells. This database, in turn, enables a new kind of "in silico cytometry" similar to conventional flow cytometry, except that all sorting occurs computationally based on genomic sequence markers and these biomarkers need not be specified to collect data a priori. To demonstrate this, SiC-seq and in silico cytometry is applied to a sample of marine microbes, and was used to measure how antibiotic resistance genes, virulence factors, and phage-associated sequences are distributed throughout the population. The ability to repeatedly sort through a population of genomes without having to perform additional wet lab experiments allows rapid iteration through hypotheses and enhances what can be discovered by what is learned. It is valuable for generating correlation maps between characteristic sequences, to infer how different phenotypes are correlated within single cells, and how genetic elements spread through a community.

Materials and Methods:

Microfluidic Devices:

To fabricate the microfluidic devices, poly(dimethylsiloxane) (Dow Corning, Sylgard 184) was poured over a negative photoresist (MicroChem, catalog no. SU-8 3025) patterned on a silicon wafer (University Wafer) using UV photolithography. The PDMS devices were cured in an oven for 1 hour, extracted with a metal scalpel, and punched with a 0.75 mm biopsy core (World Precision Instruments, catalog no. 504529) to create inlets and outlets. Devices were bonded to a glass slide using an oxygen plasma cleaner (Harrick Plasma) and the channels treated with Aquapel (PPG Industries) and baked at 80° C. for 10 min to render them hydrophobic.

Barcode Emulsions:

Barcode emulsions were prepared through digital PCR process wherein barcode oligonucleotides were amplified as single molecules in droplets containing PCR reagents. Barcode oligonucleotides (GCAGCTGGCGTAATAGCGAG-TACAATCTGCTCTGATGCCGCATAGNNNNNNN NNNNNNTAAGCCAGCCCCGACACT) (SEQ ID NO:5)

(IDT) at 0.01 pM concentration were added to a PCR reaction mix containing 1×NEB Phusion Hot Start Flex Master Mix (NEB, catalog no. M0536L), 2% (w/v) Tween 20 (Sigma-Aldrich, catalog no. P9416), 5% (w/v) PEG-6000 (Santa Cruz Biotechnology, catalog no. sc-302016), and 400 nM primers FL128 (CTGTCTCTTATACA-CATCTCCGAGCCCACGAGACGTGTCGGGGCTGGC-TTA) (SEQ ID NO:6) and FL129 (CAAGCAGAAGACGG-CATACGAGATCAGCTGGCGTAATAGCG (SEQ ID NO:7), contains P7 adapter sequence) (IDT). The PCR mixture and HFE-7500 fluorinated oil (3M) with 2% (w/w) PEG-PFPE amphiphilic block copolymer surfactant (008-Fluoro-surfactant, Ran Technologies) were loaded into separate 1 mL syringes (BD) and injected at 300 and 500 L/hr, respectively, into a flow-focusing droplet maker using syringe pumps (New Era, catalog no. NE-501) controlled with a custom Python script ("https:" followed by "//github." followed by "com/AbateLab/Pump-Control-Program"). The emulsion was collected in PCR tubes, and the oil underneath the emulsion removed via pipette and replaced with FC-40 fluorinated oil (Sigma-Aldrich, catalog no. 51142-49-5) with 5% (w/w) PEG-PFPE amphiphilic block copolymer surfactant for improved thermal stability. The emulsion was thermal cycled (Bio-Rad, T100) with the following program: 98° C. for 3 min, followed by 40 cycles with 2° C. per second ramp rates of 98° C. for 10 s, 62° C. for 20 s, and 72° C. for 20 s, followed by a hold at 12° C. Fluorescent DNA staining using 10× SYBR Green I (Thermo Fisher Scientific) in HFE-7500 oil was used to quantify barcode encapsulation rate under a fluorescent microscope (Life Technologies, catalog no. AMAFD1000).

Cell Culture and Counting:

To generate an artificial community with which to validate the SiC-seq workflow, liquid cultures of *Staphylococcus epidermidis*, *Saccharomyces cerevisiae* (strain S288c), and *Bacillus subtilis* (strain 168) were grown overnight in a shaking incubator. The following culture conditions were used: *Staphylococcus epidermidis* and *Bacillus subtilis* are grown in 3 mL LB broth at 37° C.; *Saccharomyces cerevisiae* was grown in 3 mL YPD broth at 30° C. Cell concentration was determined by manually counting serial dilutions of the liquid culture on plastic slides (Thermo Fisher Scientific, catalog no. C10228) using a microscope. The cultures were kept at 4° C. before being used in the microfluidic experiment (see section titled Cell Encapsulation in Agarose droplets).

Water Sample Collection and Filtering:

To obtain a natural sample of a microbial community, marine water was collected from Ocean Beach in West San Francisco, Calif., USA (37°44'55.6"N 122°30'33.6"W). Approximately 2 L of water was obtained by submerging two 1000 mL glass bottles below the water surface ~20 m from the shoreline. Samples were placed on ice during transport to the lab. 100 mL of the sample was passed through a 40 µm cell strainer (Corning, product no. 352340) to remove large debris, including sand. The sample is loaded into a 0.45 µm vacuum filter (Millipore, catalog no. SCHVU01RE); this filtering step separates microbes, which are captured on the membrane, and viruses, which are discarded in the filtrate. The membrane was extracted from the apparatus using a scalpel and inserted into a 15 mL centrifuge tube, to which 5 mL of PBS was added. The tube was vortexed at high speed for ~2 min to free the bacterial cells from the membrane. Finally, the cell solution was loaded into a 10 mL syringe and passed through a 5 µm syringe filter (Millipore, catalog no. SLSV025LS) to remove remaining large particulate. The marine cells were counted using the same protocol as the liquid cultures.

Cell Encapsulation in Agarose Microgels:

To prepare the artificial community for processing through the SiC-seq workflow, the frozen stock of cells (Zymo Research, catalog no. D6300) were thawed gently in a room-temperature water bath. Cell concentration was determined by manual cell counting under a microscope, and diluted to an appropriate concentration for single cell encapsulation. The calculated volume of cell solution was transferred to a 1.5 mL centrifuge tube (Fisher Scientific) and washed twice in 1 mL PBS. The cells were re-suspended in a 1 mL solution of PBS containing 17% OptiPrep Density Gradient Medium (Sigma-Aldrich), 0.1 mg/mL BSA (Sigma-Aldrich, catalog no. A9418), and 1% (v/v) Pluronic F-68 (Life Technologies). The cell solution was loaded into a 1 mL syringe and placed on a syringe pump (New Era, catalog no. NE-501). 1 mL of a 3% solution of low gelling temperature agarose (Sigma-Aldrich, catalog no. A9414) and TE buffer (Teknova, catalog no. T0225) was prepared in a 1.5 mL centrifuge tube and heated on a block at 90° C. for approximately 10 minutes to completely dissolve the agarose powder. The hot agarose was transferred to a 1 mL syringe and placed on a syringe pump. To keep the agarose molten during the microfluidic experiment, a personal space heater was positioned ~5 cm from the agarose syringe and set to run continuously at high heat. HFE-7500 fluorinated oil with 2% (w/w) de-protonated Krytox surfactant (DuPont, catalog no. 157FSH) was loaded into a 3 mL syringe. The cell solution, molten agarose, and oil were injected into the co-flow droplet maker at flow rates of 200, 200, and 400 µL/hr, respectively, to form the 1.5% agarose microgels. Approximately 500 µL of droplets were collected in a 15 mL centrifuge tube on ice and incubated for 30 min at 4° C. to ensure complete solidification of the microgels.

Resuspending Microgels in Aqueous Buffer:

The droplets were centrifuged at 300 g for 1 min to maximize separation of the emulsions from the oil. The oil layer was extracted from the tube using a 5 mL syringe and discarded. Emulsions were broken using 2 mL of a 10% (v/v) solution of perfluorooctanol (Sigma-Aldrich, catalog no. 370533) in HFE-7500; the emulsions were then mixed by pipetting and centrifuged at 300 g for 1 min. The oil was removed from the tube using a syringe and the droplet breaking step is repeated. Following droplet breaking, 2 mL of hexane containing 1% (v/v) Span 80 (Sigma-Aldrich) was added to the microgels to dissolve any remaining oil, and this solution was mixed and centrifuged at 300 g for 1 min. The hexane supernatant was removed from the tube and the hexane addition step was repeated. Finally, the microgels were washed three times in 10 mL of aqueous solution TE buffer containing 0.1% (v/v) Triton X-100 nonionic surfactant (Sigma-Aldrich). The microgels were centrifuged at 1000 g for 2 min and the supernatant aspirated between washes. The washed microgels were stored in 5 mL TE buffer at 4° C. prior to cell lysis.

Cell Lysis in Microgels:

To lyse the cells in the microgels, the particles were submerged in a solution of 2 mL TE buffer solution containing 10 mM DTT (manu), 2.5 mM EDTA (Teknova), and 10 mM NaCl (Sigma-Aldrich). The following quantities of lytic enzymes were also included: 4 U zymolyase (Zymo Research), 10 U lysostaphin (Sigma-Aldrich, catalog no. L7386), 100 U mutanolysin (Sigma-Aldrich, catalog no. M9901), and 40 mg lysozyme (MP Biomedicals, catalog no. 195303). Cell lysis proceeded overnight in a shaking incubator at 37° C. The turbid lysate mixture was centrifuged at 1000 g for 1 min, the supernatant removed, and 3 mL of a solution containing 0.5% (w/v) lithium dodecyl sulfate (Sigma-Aldrich) and 10 mM EDTA in TE buffer was added, along with 4 U of Proteinase K (NEB) to solubilize cell debris and digest cellular proteins. The solution was incubated at 50° C. on a heating block for 30 min. Following lysis, the microgels were thoroughly washed to ensure complete removal of detergents and other chemical species which may inhibit downstream molecular biology reactions. The following washes occurred in 10 mL volumes with centrifugation magnitudes of 1000 g between additions of wash solutions: one wash with 2% (v/v) Tween 20 in water; one wash in 100% ethanol (Koptec) to denature any remaining Proteinase K; and five washes with 0.02% (v/v) Tween 20 in water.

Tagmentation of Genomic DNA in Microgels:

Using reagents from a Nextera DNA Library Prep Kit (Illumina, catalog no. FC-121-1030), the washed and lysed gels containing high-molecular-weight genomic DNA were simultaneously fragmented and tagged with a common adapter sequence. Microgels were re-encapsulated into droplets to minimize cross-contamination during the tagmentation step. A solution of 192 µL DI water, 200 µL tagmentation buffer, and 8 µL Nextera enzyme was prepared and loaded into a 1 mL syringe. Microgels and the tagmentation solution were injected into the re-encapsulation device (FIG. 1, panel B). The re-encapsulated microgels were incubated in a 1.5 mL tube on a heating block at 50° C. for one hour.

Microfluidic Barcoding of Encapsulated Cells:

Tagmented microgels, barcode droplets, and 500 µL of PCR solution containing 1× Invitrogen Platinum Multiplex PCR Master Mix (Thermo Fisher Scientific, catalog no. 4464268), 400 nM primers FL127 (AATGATACGGCGAC-CACCGAGATCTACACTCGTCGGCAGCGTC (SEQ ID NO:8), contains P5 adapter sequence) and FL129 (CAAGCAGAAGACGGCATACGAGATCAGCTGGC-GTAATAGCG) (SEQ ID NO:7), 50× dilution of NT buffer from the Nextera XT Kit (0.2% SDS) (Illumina, catalog no. FC-131-1024), 1% (w/v) Tween 20, 1% (w/v) PEG-6000, 2.5 U/µL Bst 2.0 WarmStart DNA Polymerase (NEB, catalog no. M0538S) were each loaded into a 1 mL syringe and injected into the merger device as shown in FIG. 1. HFE-7500 fluorinated oil with 2% (w/w) 008-Fluorosurfactant was used as the continuous phase of the emulsion. Merger of the barcode and gel droplet emulsions was achieved using an electrode connected to a cold cathode fluorescent inverter and DC power supply (Mastech). A voltage of 2.0 V at the power supply produced a ~2 kV AC potential at the electrode which causes touching droplets to merge. The emulsion was collected in a 0.5 mL thin-walled PCR tube (Applied Biosciences), and the HFE-7500 replaced with FC-40 with 5% (w/w) 008-Fluorosurfactant prior to thermal cycling with the following protocol: 65° C. for 5 mins, 95° C. for 2 mins, then 30 cycles at 2° C./s ramp rates of 95° C. for 15 s, 60° C. for 1 min, 72° C. for 1 min, and then 72° C. for 5 mins with optional 12° C. overnight hold. After thermal cycling, large (coalesced) droplets were removed using a micropipette, and the emulsion was broken by addition of 20 µL of perfluorooctanol and brief centrifugation in a microcentrifuge. The upper aqueous phase was collected and the DNA library was purified using a Zymo DNA Clean & Concentrator-5 kit (Zymo Research). The library was size-selected for DNA fragments in the 200-600 bp range using Agencourt AMPure XP beads (Beckman Coulter), quantified with a Bioanalyzer 2100 instrument and High Sensitivity DNA chip (Agilent), and sequenced on an Illumina MiSeq using a custom index primer (FL166).

Generating the SiC-Reads Database:

Raw reads from the MiSeq-generated FASTQ files were filtered by quality and grouped by barcode sequence using the Python script barcodeCleanup.py. A given read was discarded if more than 20% of its bases had a Q-score less than Q20, and all reads associated with a barcode containing less than 50 reads were discarded. This step ensured that all barcode groups, representing single cells, contain a sufficient number of high-quality reads. The resulting reads were exported to a table in a SQLite database with fields containing the barcode sequence, barcode group size, a unique read ID number, and read sequence. When the reference genomes were known, as in the case of the synthetic cell population experiment, the reads were aligned using bowtie2 v2.2.9 with default settings and the SQLite table was updated with relevant alignment information for each read. For environmental samples, the reads were classified by taxonomy using Kraken v0.10.5 with "--quick --min-hits 2" options set, and the output was exported to the SQLite database. krakenAnalysis.py assigns taxonomic identities from the Kraken database to barcode groups by a majority rule, in which barcode group was classified according to the most common taxonomic label among its classifiable reads. Barcode group purity was calculated from reference alignment data or phylogenetic labels using the scriptpurity.py.

In Silico Cytometry:

Reads from the SiC-Reads database were aligned, using bowtie2 v2.2.9 with -very-sensitive and -end-to-end settings to reference sequences of interest (AR database obtained from Gupta, S. K., et al., *Antimicrob. Agents Chemother.*, 58:212-220 (2014), VF database obtained from core VF genes at the virulence factor database (VFDB; Chen, L. et al., *Nucleic Acids Res.*, 33:D325-328 (2005), Phage sequence database obtained from Phage genome database accessed on May 2016 at "http:" followed by "//www.ebi.ac." followed by "uk/genomes/phage.html". Mapping reads were then filtered for MapQ >2 in order to remove ambiguously mapping reads. Barcode groups containing reads that map to the databases were annotated as containing the target sequence and were exported for further analysis if they were taxonomically classified with purity >0.8. To generate the heatmap for transduction potential, all reads that associated with a phage and a Kraken-classified barcode group were extracted and grouped according to phage type. Duplicate and near-duplicated reads were removed. The heatmap intensties were calculated as follows: for a given pair of bacterial hosts, the total number of host-phage-host connections in the database was counted. To normalize the data by host abundance, this number was divided by the total number of barcode groups associated with the two hosts.

Figure 10:
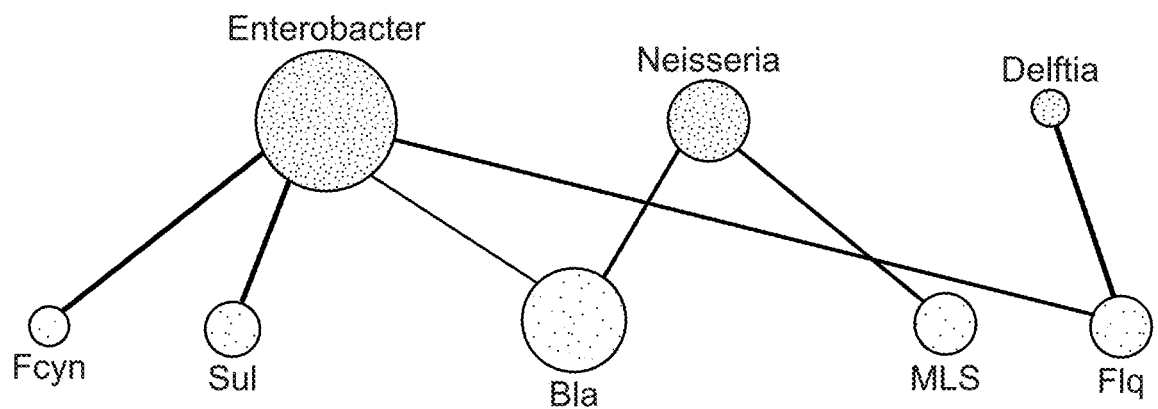
FIG. 10 depicts the reference data obtained by simulating reads from genomic sequences of isolated strains for comparison against data in the marine microbial community as described in the Examples herein. a) Antibiotics resistance network for whole genome sequenced strains in public databases. b) Virulence factor ratios calculated for publically available strains.
Figure 10:
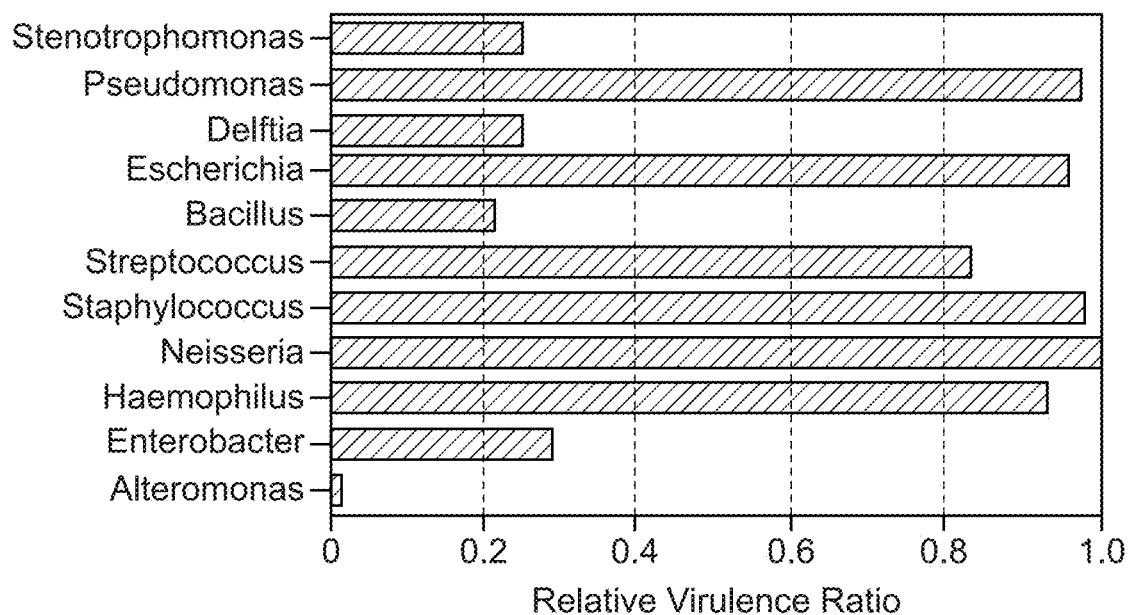

Generating the Antibiotic Resistance Network for the Sequenced Whole Genomes as Depicted in FIG. 10A:

An antibiotic resistance graph in FIG. 10A was generated using references for the 6 genomes most commonly associated with antibiotic resistance in the SiC-Reads database of the San Francisco Coast water microbial community. The following genomes (with accession numbers) were downloaded from the NCBI RefSeq repository: >CP003841.1 *Alteromonas macleodii* ATCC 27126; >CP010434.1 *Bacillus subtilis* subsp. *spizizenii* strain NRS 231; >CP000884.1|*Delfia acidovorans* SPH-1; >CP001918.1|*Enterobacter cloacae* subsp. *cloacae* ATCC 13047; >AE002098.2|*Neisseria meningitidis* MC58; and >AE017283.1|*Propionibacterium acnes* KPA171202. These genomes were combined into a single FASTA file and passed to a short read simulator, wgsim v0.3.2, which generated 10M single-end reads of 70 bp each with a base error rate of 0. These reads were aligned to the antibiotic resistant gene reference using bowtie2 in 'local' mode with default sensitivity settings. All unaligned sequences were removed using samtools (samtools view -b -F). The aligned sequences in .SAM format were imported into Cytoscape v3.4.0 and the network shown in FIG. 10A was generated using the reference genus and antibiotic resistance genes as the network targets and sources, respectively. The darkness of the graph's edges scale linearly with the total number of connections in the data, where darker lines have a greater number of associations.

Figure 9A:
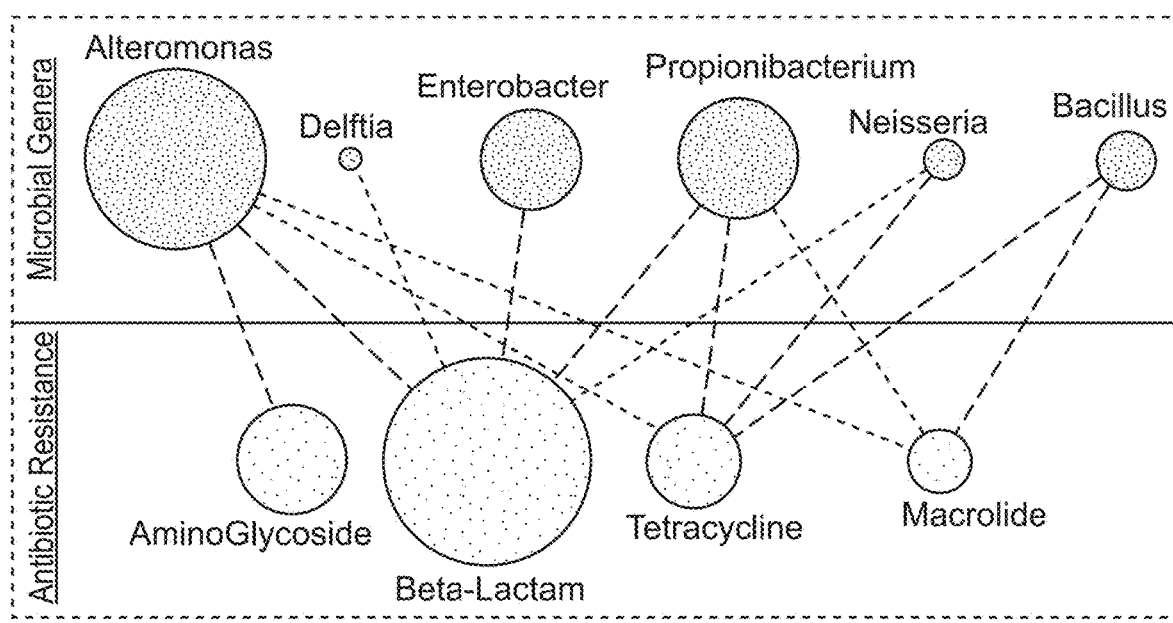
FIGS. 9A-9C illustrate the application of SiC-seq to a marine community recovered from the San Francisco coastline.
Figure 9B:
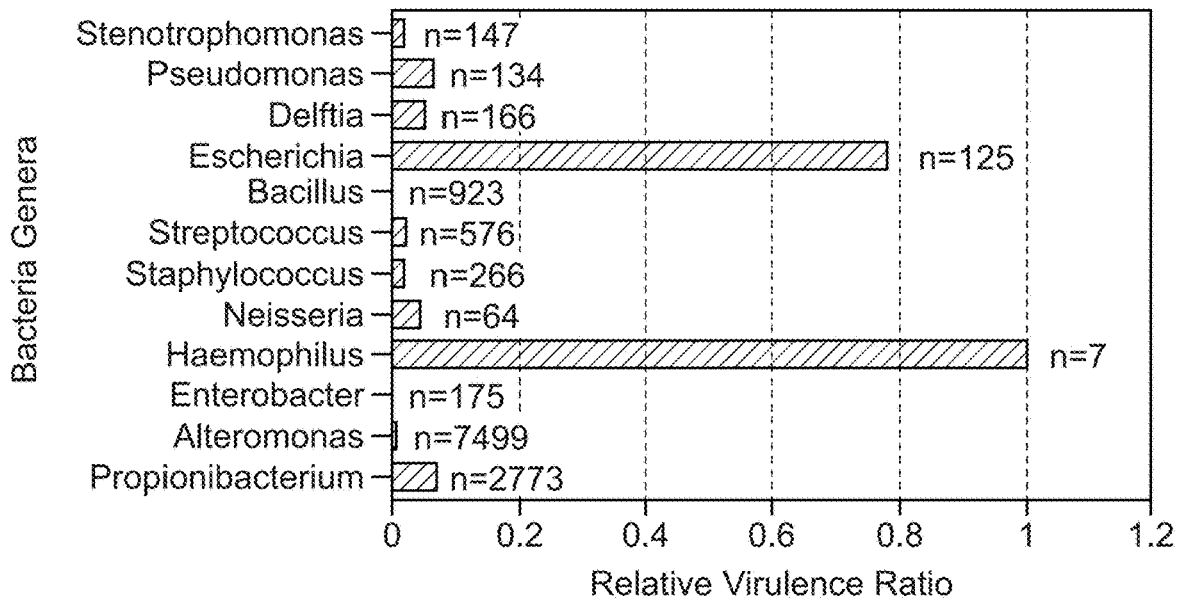

Generating the VF Ratios for the Sequenced Whole Genomes in FIG. 10B:

The VF ratios calculations in FIG. 9B was reproduced using reference genomes for the genera shown in the figure. The complete genomes of all species associated with these 12 genera were downloaded from the RefSeq database using the Perl script ncbiDownloader.pl. Genomes were pooled into FASTA files labeled by genus. From these reference files, a Python script (bargroupGenerator.py) generated simulated barcode groups of 200 reads per group, with each single-end read 150 bp long. The number of simulated bargroups generated for a given genus was equal to the number of barcode groups identified for this genus in the San Francisco Coast water sample. The simulated barcode group reads were then aligned to the original virulence factor database using bowtie2 v2.2.9 in 'local' alignment mode with default sensitivity settings. Unaligned sequences were removed using samtools v1.3.1 (samtools view -b -F) and the remaining aligned reads were used to produce the data shown in FIG. 10B.

Figure 2:
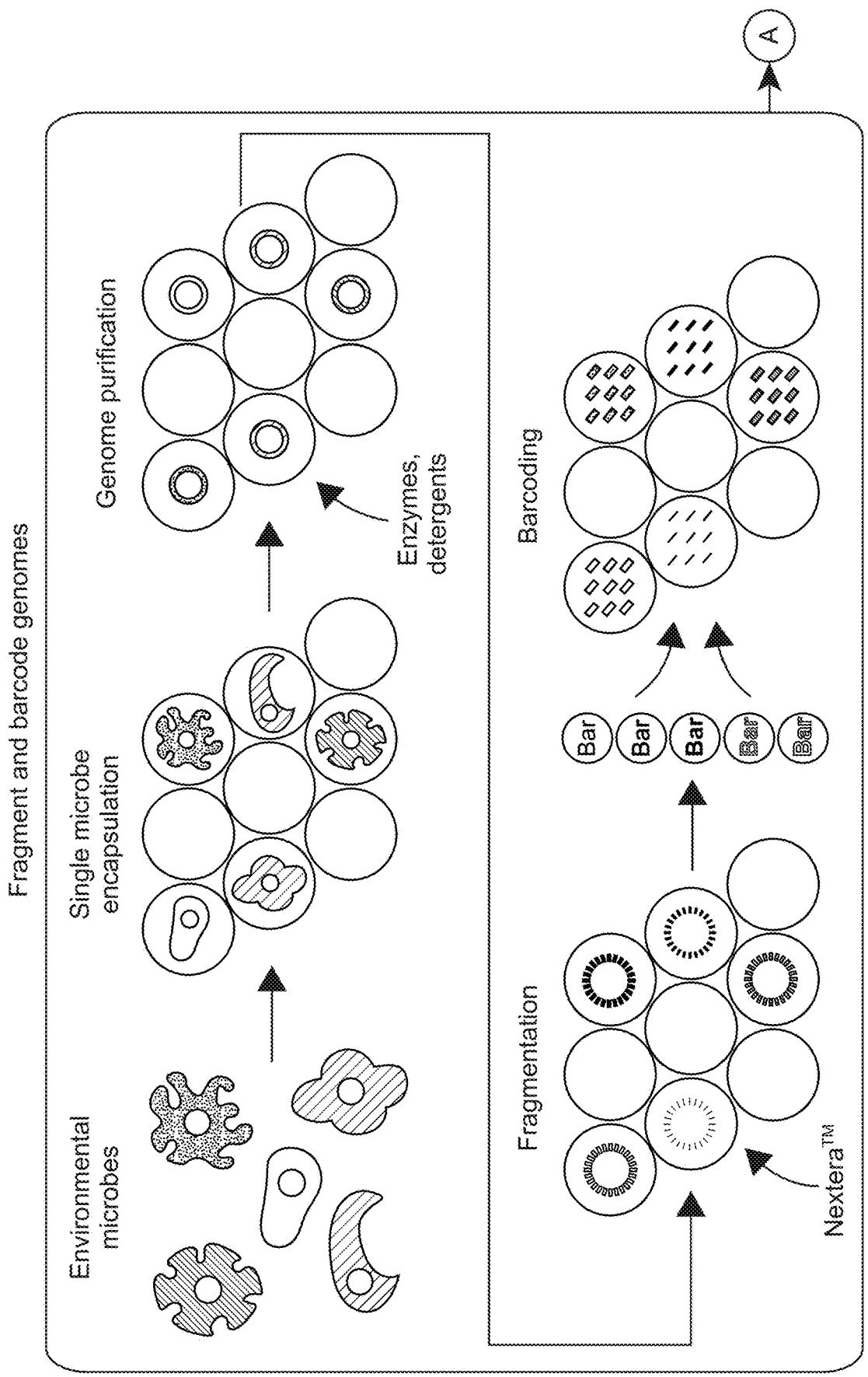
FIG. 2 provides a schematic of an example SiC-seq workflow according to one embodiment of the present disclosure. Single cells are encapsulated in microgels and the genomes purified and fragmented, e.g., in a series of detergent and enzyme washes. The genomic fragments are then labeled with nucleic acid, e.g., DNA, barcode sequences unique to each droplet. The resulting barcoded genomic fragments are pooled and sequenced, generating reads that can be grouped by single cells based on shared barcode. The groups of reads comprise a database of low coverage genomes of single cells, which can be analyzed, e.g., using in silico cytometry.
Figure 2:
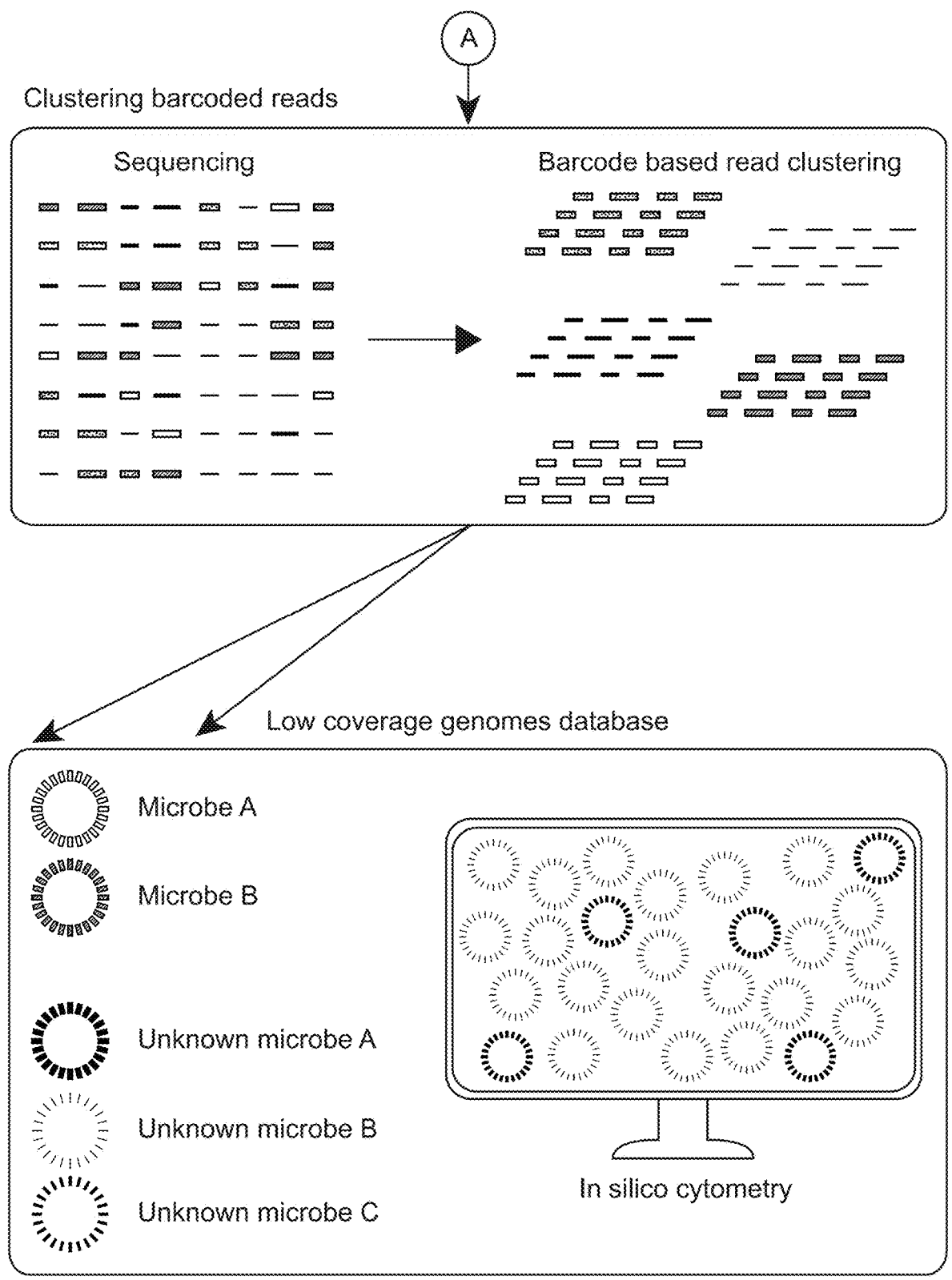

Results:

SiC-Seq Workflow:

Droplet microfluidics, with its ability to encapsulate and perform biological reactions on thousands of single cells per second, affords unparalleled potential for single molecule and single cell applications, including to uniformly amplify, accurately quantitate, and deeply sequence single molecules, and to culture, screen, and sequence the transcriptomes of single cells. However, single cell genome sequencing presents the unique challenge that each cell's genome is protected by membranes and proteins that may need to be removed before enzymatic processing is possible. The reagents often utilized in genome purification, including detergents, proteases, and high pH buffers, however, may be detrimental to enzymes used in preparation for sequencing, requiring that these steps be performed separately. In SiC-seq, this was addressed by encasing cells in hydrogel microspheres (microgels) that are permeable to molecules with hydraulic diameters smaller than the pore size, including enzymes, detergents, and small molecules, but sterically trap large molecules such as genomes. This allows for the use of a series of "washes" on millions of encased cells, to perform the steps of cell lysis and genome processing, while maintaining compartmentalization of each genome. Using a combination of microgel and microfluidic processing steps, the cells are lysed, genomes are fragmented, and unique barcodes are attached to all fragments, in a workflow that processes >50,000 cells in a few hours. The barcoded fragments for all cells can then be pooled and sequenced, and the reads grouped by barcode, providing a library of single cell genomes that can be subjected to additional downstream processing, including demographic characterization and in silico cytometry. A diagram of the workflow for SiC-seq is provided in FIG. 2.

An aspect of SiC-seq that facilitates ultrahigh-throughput processing and sequencing of single cells is the labeling of DNA fragments originating from the same genome with a sequence identifier (barcode) unique to that cell. The resultant products are chimeric, including a barcode sequence covalently linked to a random fragment of the cell genome. The barcodes allow all reads belonging to a given cell to be identified through shared sequence. To uniquely barcode the genomic fragments of many single cells, a library of unique barcode sequences is utilized. Recently published methods to barcode single cell transcriptomes introduce barcodes attached to solid beads or hydrogel spheres (Klein, A. M., et al., *Cell*, 161:1187-1201 (2015); Macosko, E. Z., et al., *Cell*, 161:1202-1214 (2015), the disclosures of each of which are incorporated by reference herein). Such methods may be utilized in connection with the methods described herein. However, in the embodiment of SiC-seq exemplified herein, liquid droplets containing the barcode sequences are merged with the genomes to be barcoded (See, e.g., Lan, F., et al., *Nat. Commun.*, 7:11784 (2016), the disclosure of which is incorporated by reference herein).

Figure 3A:
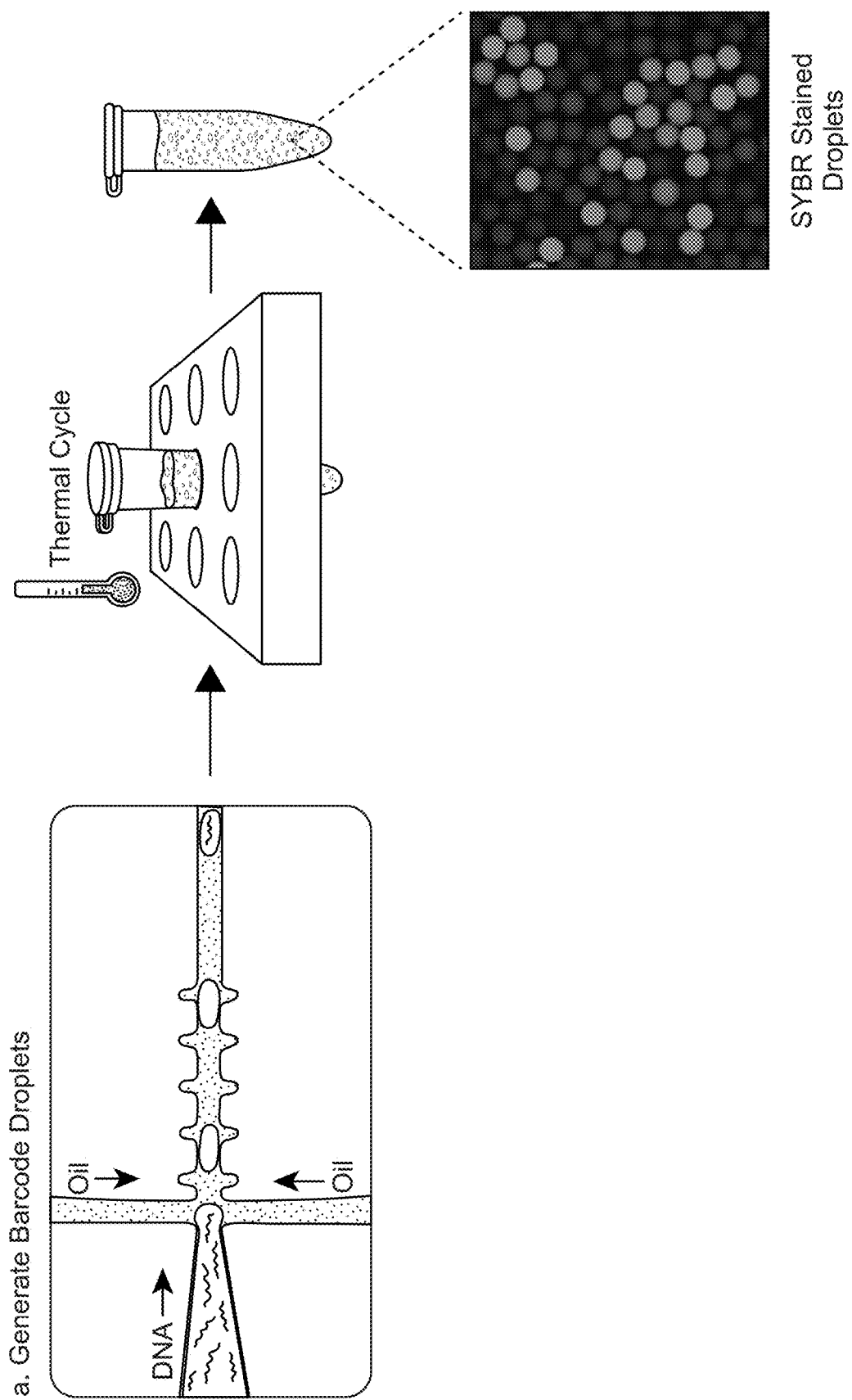
FIGS. 3A-3C provide schematics of microfluidic and biochemical workflow to generate a SiC-seq library according to one embodiment of the present disclosure.

To prepare a barcode droplet library, oligonucleotides including 15 random bases flanked by constant sequences were encapsulated at a rate of 0.1 using microfluidic flow focusing (FIG. 1, Panel A and FIG. 3A) (Garstecki, P., et al., *Appl. Phys. Lett.*, 85:2649-2651 (2004), the disclosure of which is incorporated by reference herein). A single barcode molecule, however, is generally insufficient to label a cell's genome, and accordingly the barcode molecule is generally amplified prior to the barcoding process. To accomplish this, droplets are generated using PCR reagents and primers complementary to the constant regions of the barcodes and which contain the Illumina P7 flow cell adapter. The droplets are then thermal cycled to amplify the barcode sequences via digital droplet PCR. This approach generated ~10 million barcode droplets in a few hours in an efficient manner.

Figure 3B:
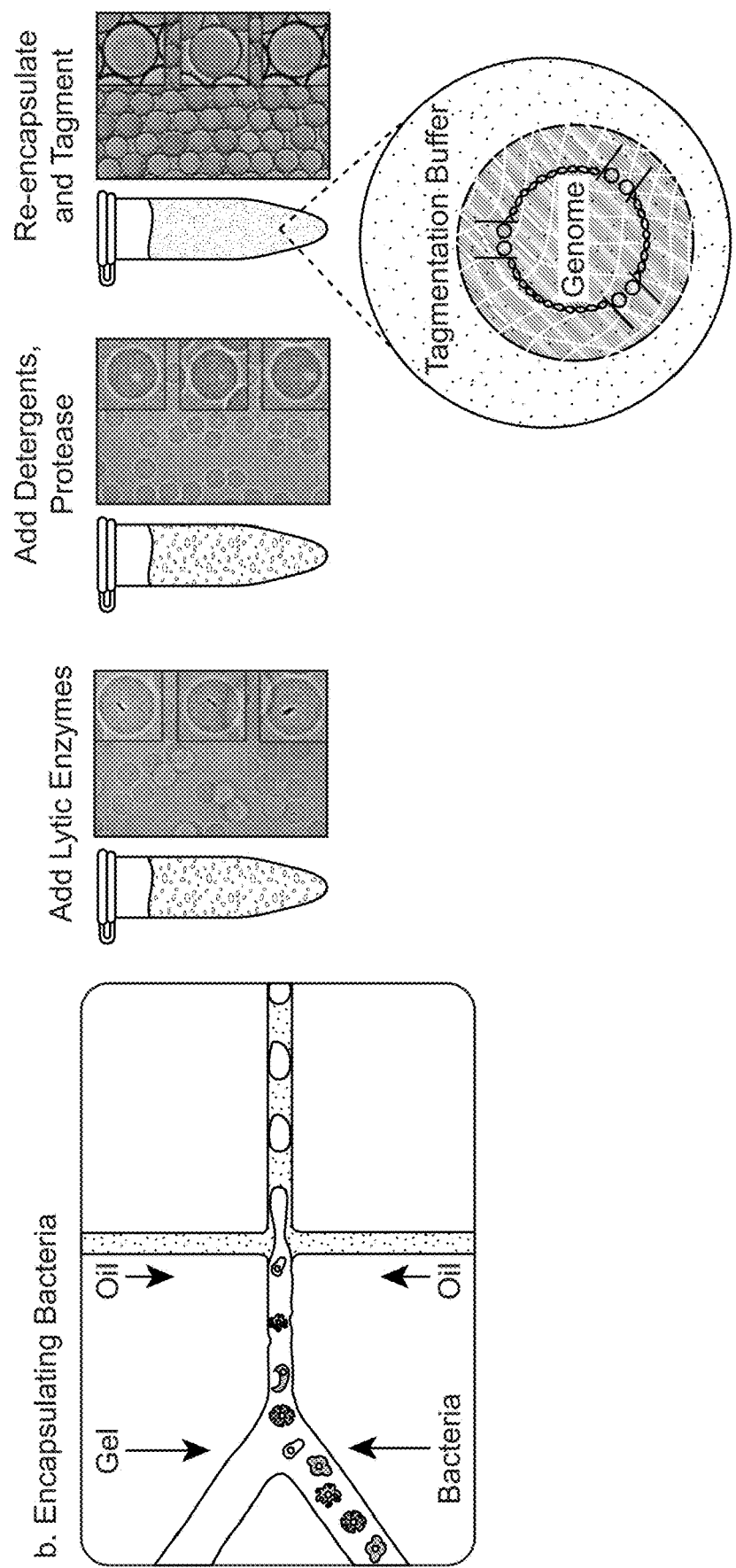

Before the single cell genomes can be barcoded, they are generally physically isolated and purified from the cell body and fragmented. To accomplish this, single cells were encased in agarose microgels using a two-stream co-flow droplet maker, which merged a cell suspension stream with a molten agarose stream, forming a droplet consisting of an equal volume of both streams (FIG. 3B and FIG. 1, Panel A). The droplet maker ran at ~10 kHz, which allowed for the generation of 10 million 22 μm droplets in ~20 minutes, a total volume of aqueous emulsion fraction ~60 μL. Hence, droplet generation was fast and the total volume consumed small, allowing for the loading of cells at a rate of 1:10 to minimize multi-cell encapsulation; this reduced the likelihood that coalescence during thermal cycling mixed droplets containing different genomes, which would yield undesirable non-single cell barcode groups.

Figure 4:
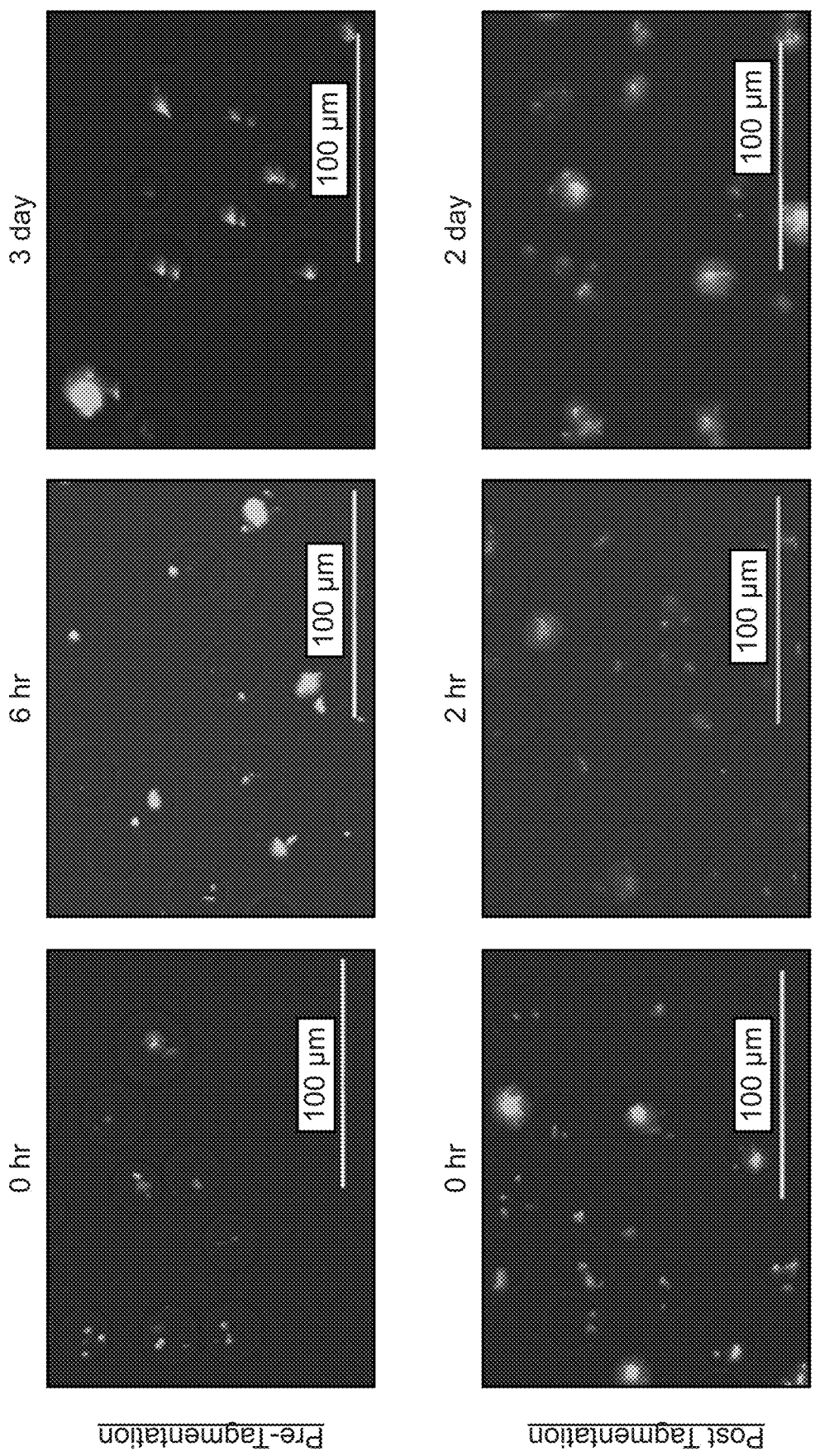
FIG. 4 depicts microscope images and plots characterizing the diffusion of genomic fragments inside agarose microgels. a) SYBR staining was used to monitor diffusion of genomes in microgels before and after tagmentation. b) After two days at room temperature, the microgels were pelleted by centrifugation and DNA was extracted from the microgels and the supernatant and quantified using the Qubit dsDNA high sensitivity assay and bioanalyzer high sensitivity DNA chip. The shift in fragment size was relatively minor as a result of the relatively low stoichiometric ratio of transposase to genome used. c) Encapsulated genomes were reacted with a higher stoichiometric ratio of transposase to genome and were visualized on a bioanalyzer high sensitivity chip to show fragmentation efficiency of the gel-encapsulated genomes.
Figure 4:
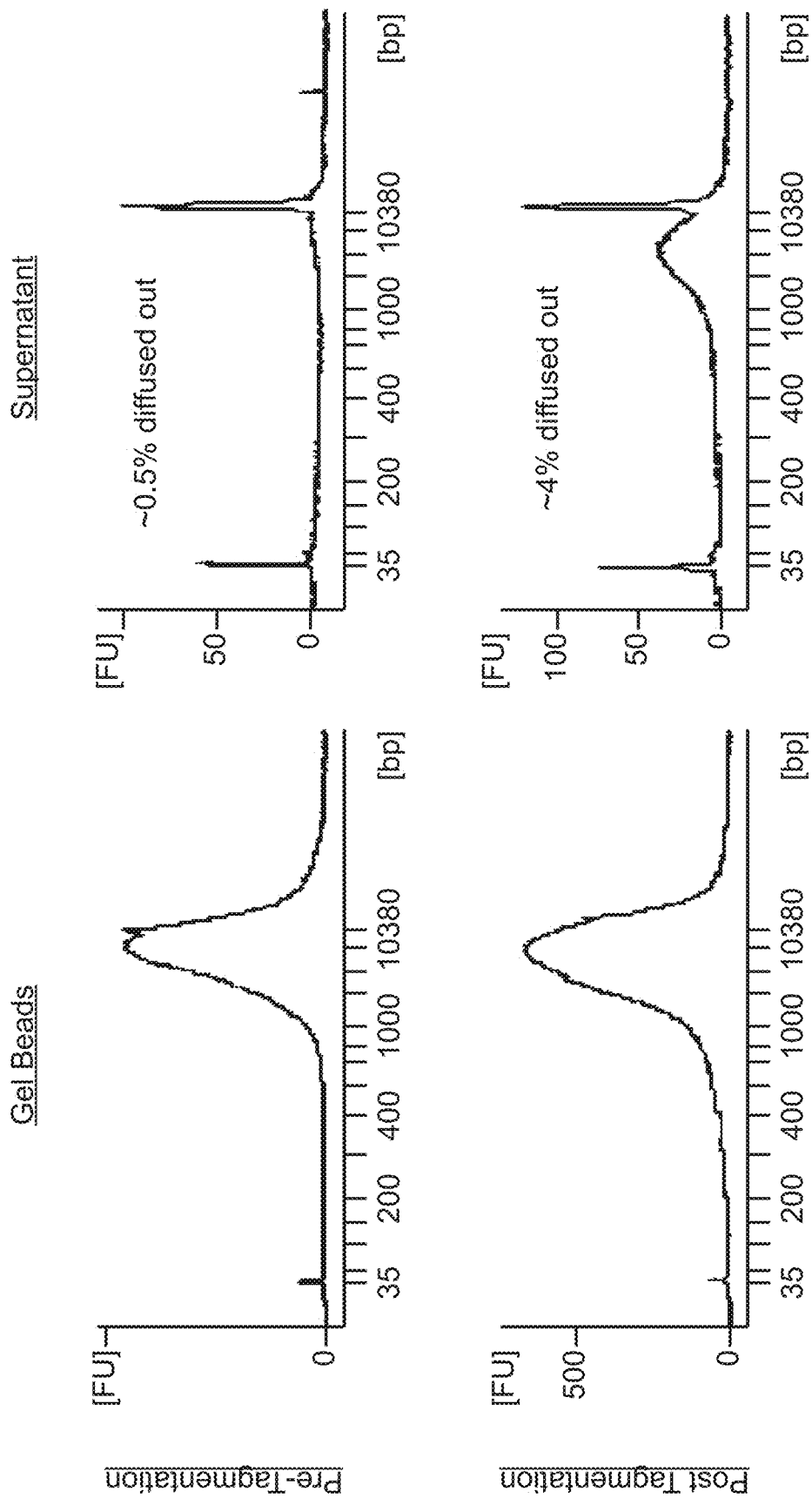
Figure 4:
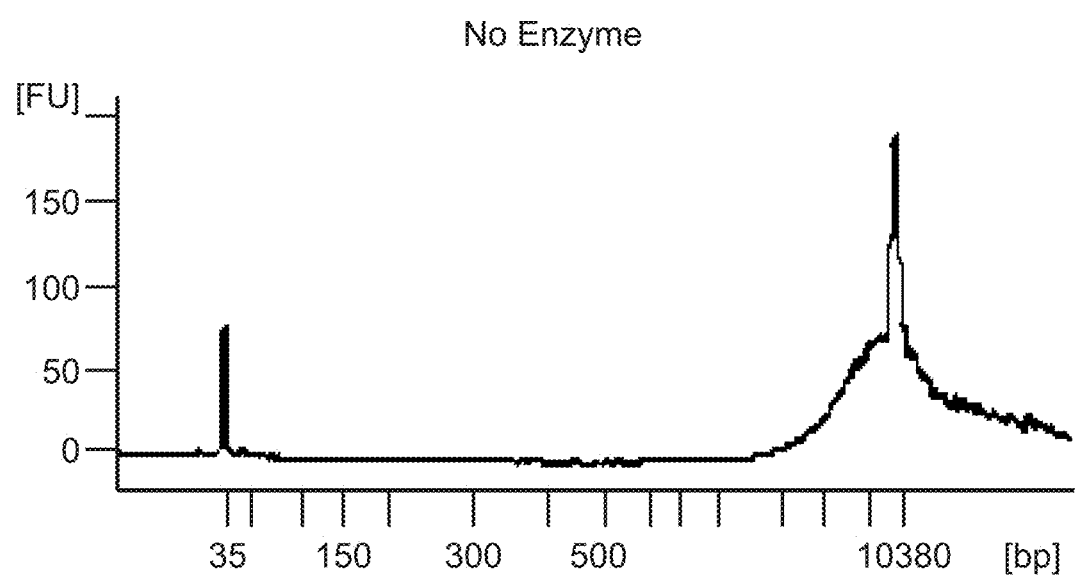
Figure 4:
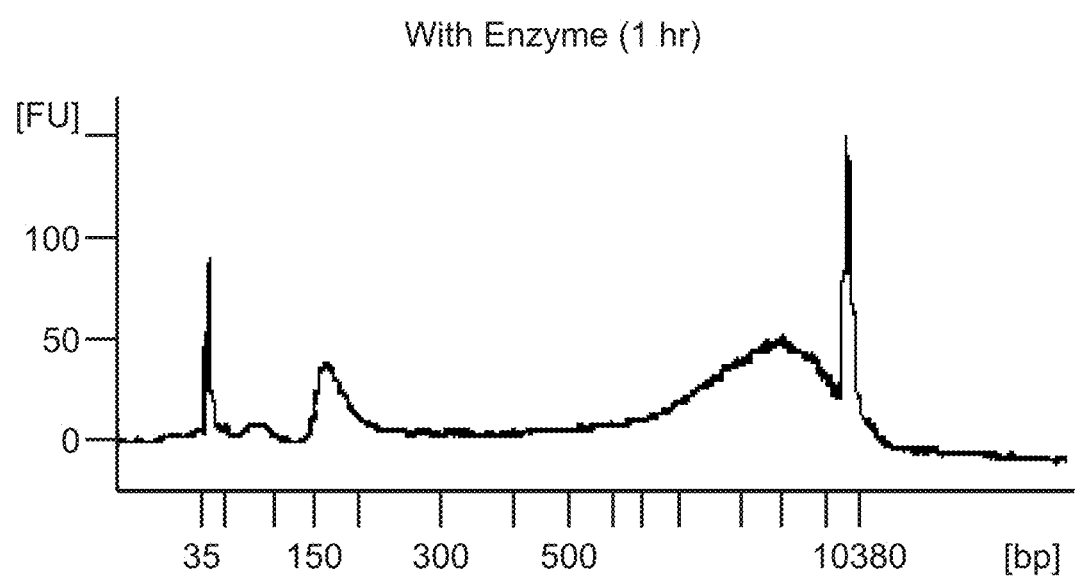

The molten agarose droplets were collected into PCR tubes on ice, solidifying them. The solidified microgels were then transferred from oil to water, while maintaining encapsulation of the cells, which were then subjected to lysis and genome purification. To lyse the cells, the solidified microgels were incubated overnight in a mixture of lytic enzymes, digesting the protective microbial cell walls (see, Materials and Methods). They were then incubated in a mixture of detergents and proteases for 30 minutes, solubilizing lipids and digesting proteins, preserving only high molecular weight genomic DNA, which was verified by staining with SYBR green dye. To fragment the genomes and attach the universal sequences to act as PCR handles, the solidified microgels were re-encapsulated in the Nextera® reaction (FIG. 1, Panel B). Importantly, because the transposases are dimeric, the fragmented genome remains intact as a macromolecular complex, remaining sterically encased within the hydrogel network (FIG. 4).

Figure 3C:
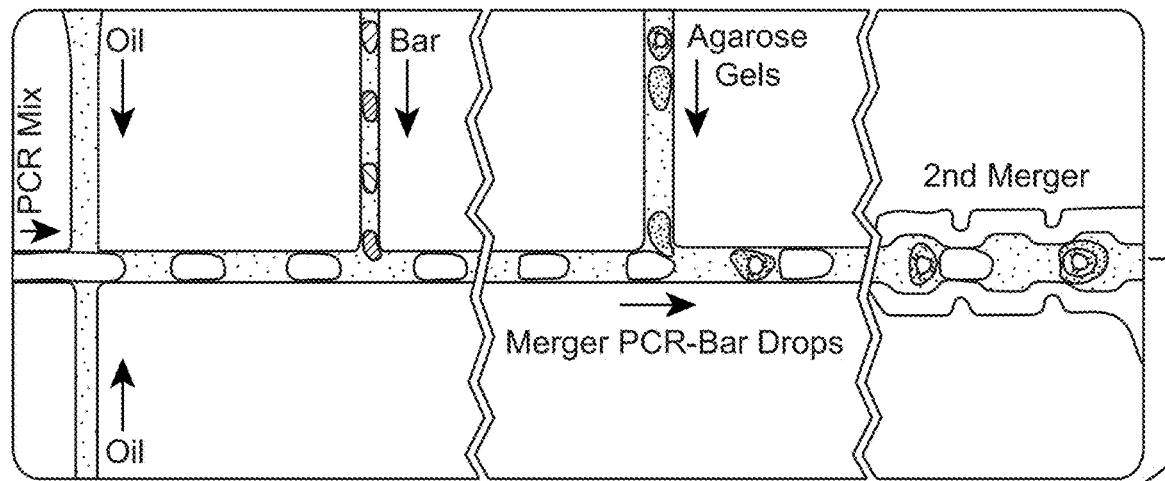
Figure 3C:
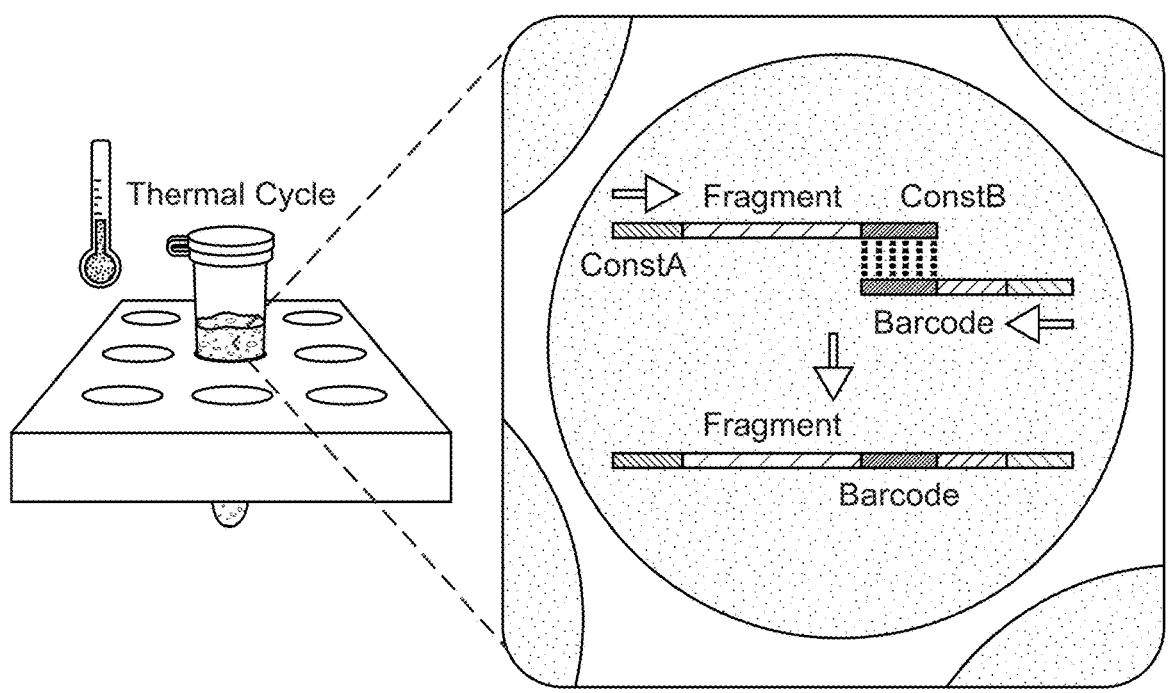

After the genomes are purified and fragmented, they are barcoded for sequencing. A microfluidic device that encapsulates each solidified microgel in PCR reagents is used, the device then merges the solidified microgel with a barcode droplet (FIG. 3C and FIG. 1, panel C). Monodisperse microgels have the unique and valuable property that, because they are compliant, they can flow at high volume fraction (>0.65) through microfluidic channels without clogging, causing them to order and flow periodically into a droplet generator. By matching the droplet period with the microgel injection period, it is possible to achieve efficient loading of microgels in droplets, a technique that has been exploited for human genome haplotyping and single cell transcriptome sequencing with minimal cell loss and is a part of commercialized droplet microfluidic instrumentation. The droplets containing fragmented-genome and barcode are collected into a PCR tube and thermal cycled, splicing the barcode sequences onto the genomic fragments via complementarity through the PCR handles added by the transposase. At this point, the spliced fragments contain both the P5 and P7 Illumina sequencing adaptor required for sequencing on the Illumina platforms. During thermal cycling, some droplets coalesce, generating barcode clusters corresponding to multiple cells. These coalesced droplets were removed using a micropipette at the end of thermal cycling, and then the purified droplets were chemically ruptured, and their contents pooled and prepared for sequencing (see, Materials and Methods). After sequencing, the reads were filtered by quality and grouped by barcode, providing single cell genomic sequence data.

Figure 5B:
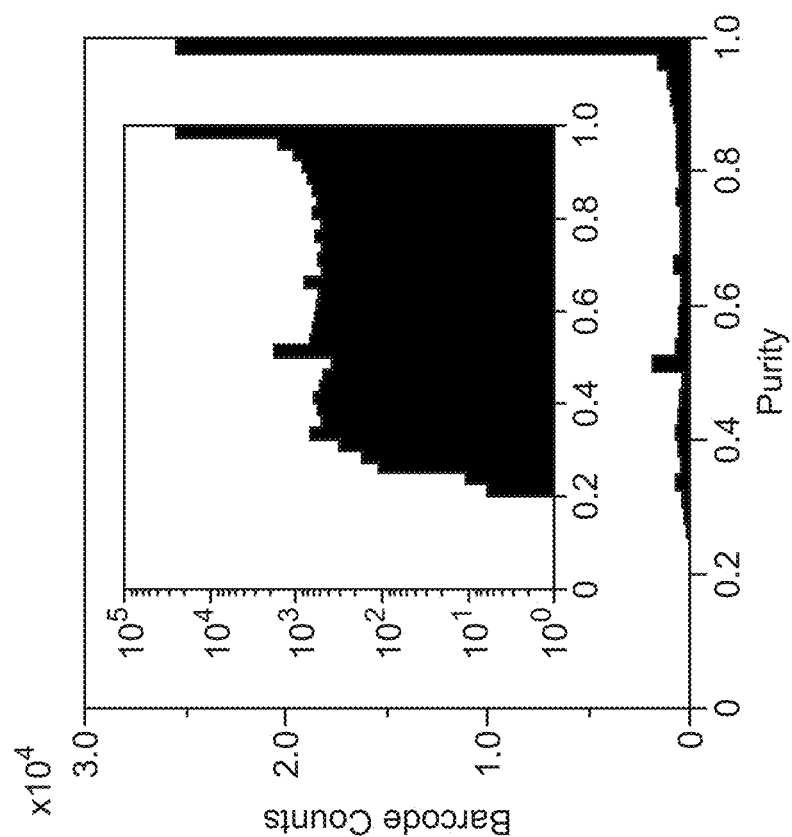
FIGS. 5A-5E depict plots demonstrating the performance of SiC-seq on an artificially constructed microbial community.
Figure 5A:
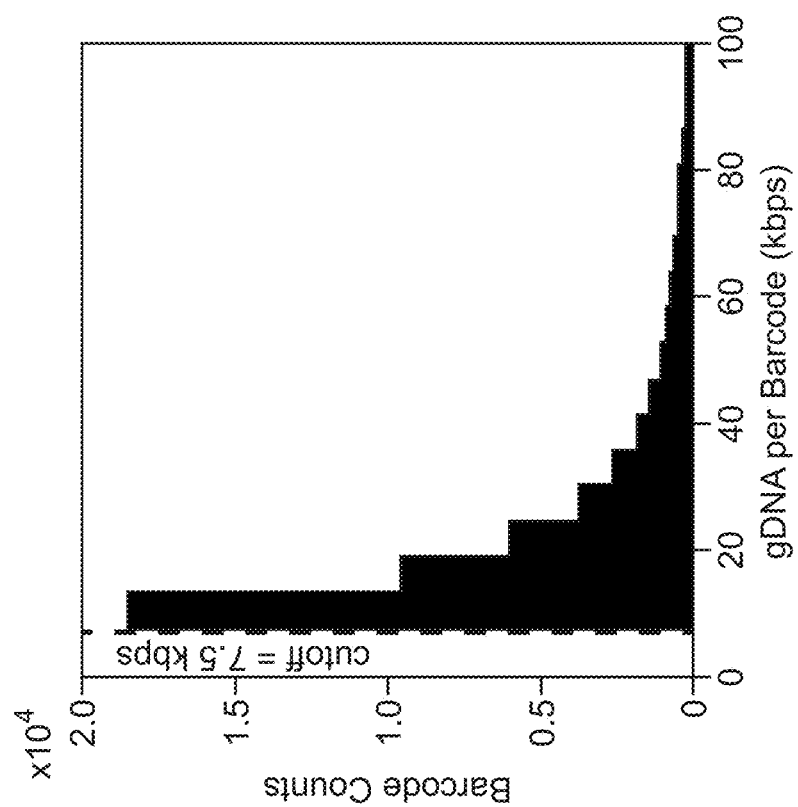
Figure 11:
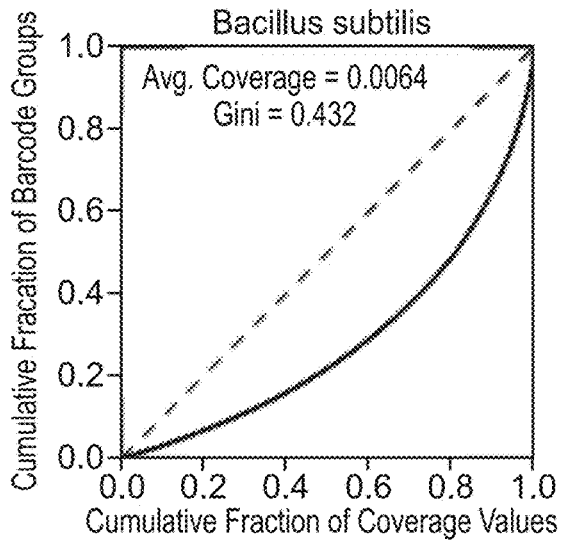
FIG. 11 depicts plots showing the average and distribution of genome coverage of each barcode group plotted as a Lorenz curve for each species.
Figure 11:
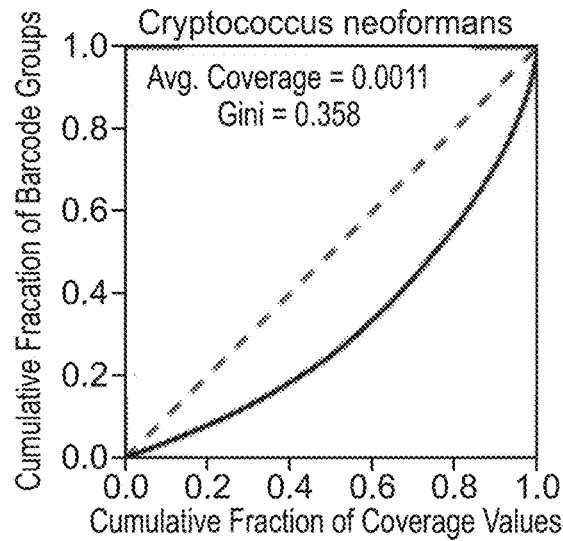
Figure 11:
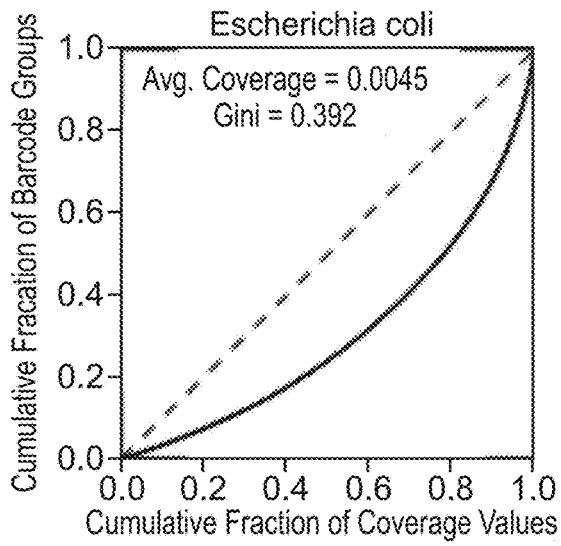
Figure 11:
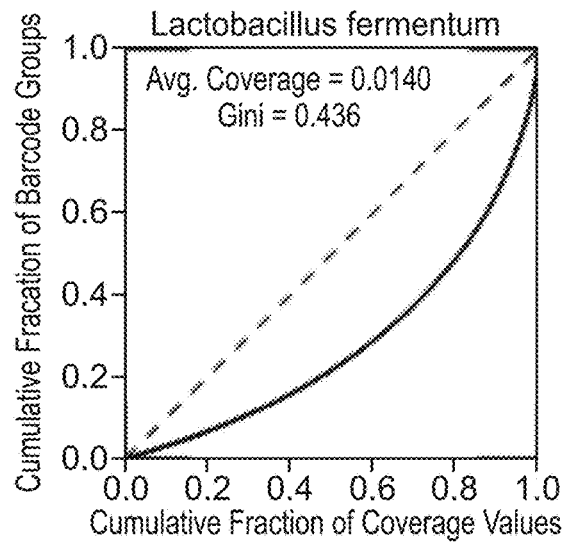
Figure 11:
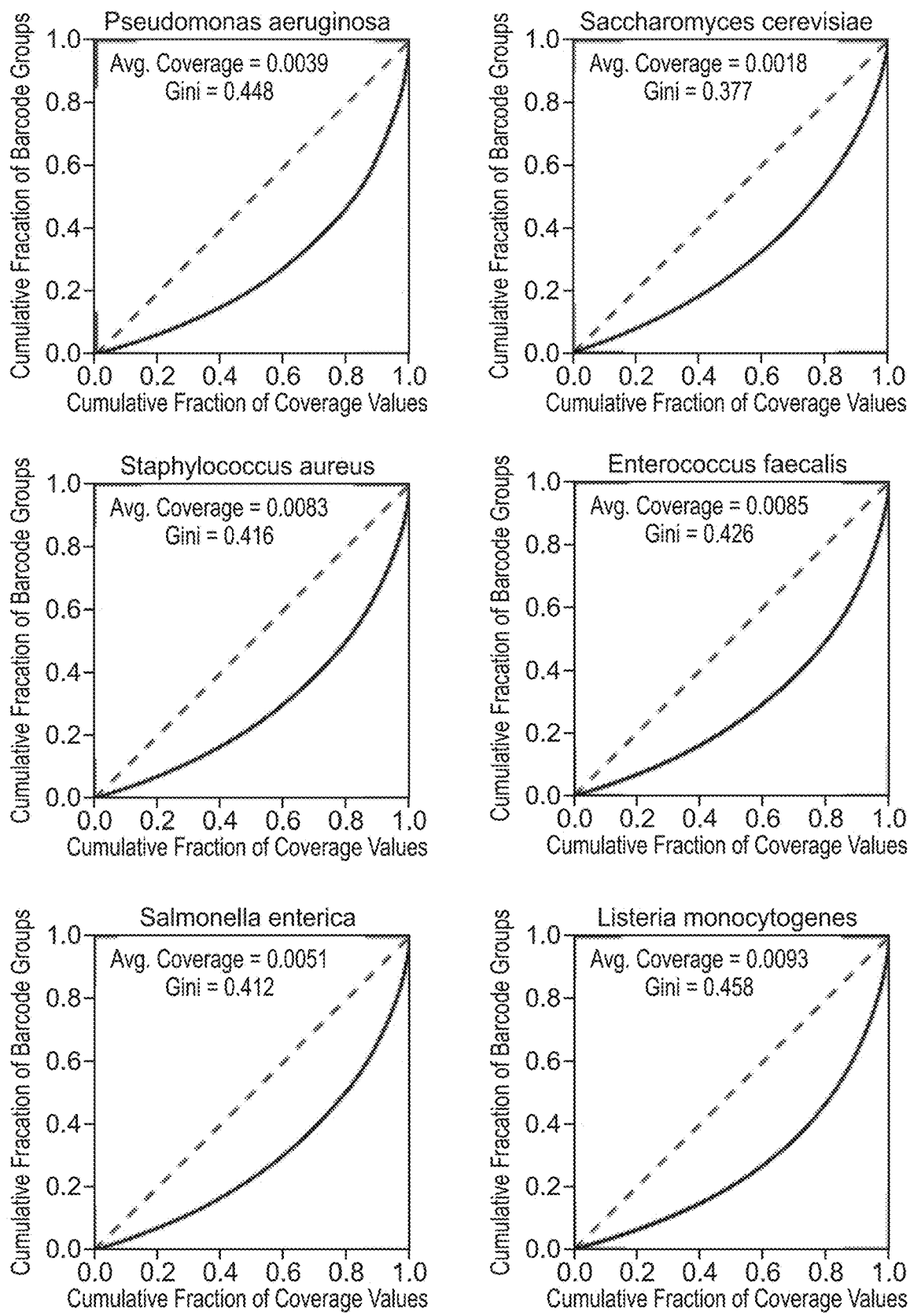

Validation of SiC-Seq on an Artificial Microbial Community:

The objective of SiC-seq is to provide single cell genomic sequences bundled in barcode groups; this data can then be used for microbial demographic characterization, to correlate interesting sequences within the same genome, and as potential scaffolds for genome assembly. To validate that SiC-seq generated single cell barcode groups, it was applied to an artificial community containing five Gram-positive bacteria, three Gram-negative bacteria, and two yeasts mixed in equal proportion by genomic DNA content (Table 1, below) To confirm that the lysis procedures were reasonably general, this mixture represented gram-positive bacteria and fungi, which are typically difficult to lyse. A single-cell library was prepared from this community using SiC-seq and it was sequenced on an Illumina MiSeq, yielding ~6 million paired-end reads of 150 bp after quality filtering. Reads were grouped by barcode and groups with <50 reads were discarded, representing likely PCR-mutated barcode sequences, and yielded the final 48,989 barcode groups (FIG. 5A). Each barcode group theoretically represents a low-coverage genome of a cell, with an average depth of coverage of 1% and a distribution that is similar for all microbes (FIG. 11).

TABLE 1

Listing of the ten cell types in artificial community

| Organism | GC % | Gram |
|---|---|---|
| Bacillus subtilis | 43.8 | Positive |
| Cryptococcus neoformans | 48.2 | N/A (Yeast) |

TABLE 1-continued

Listing of the ten cell types in artificial community

| Organism | GC % | Gram |
|---|---|---|
| Enterococcus faecalis | 37.5 | Positive |
| Escherichia coli | 56.8 | Negative |
| Lactobacillus fermentum | 52.8 | Positive |
| Listeria monocytogenes | 38.0 | Positive |
| Pseudomonas aeruginosa | 66.2 | Negative |
| Saccharomyces cerevisiae | 38.4 | N/A (Yeast) |
| Salmonella enterica | 52.2 | Negative |
| Staphylococcus aureus | 32.7 | Positive |

Figure 12:
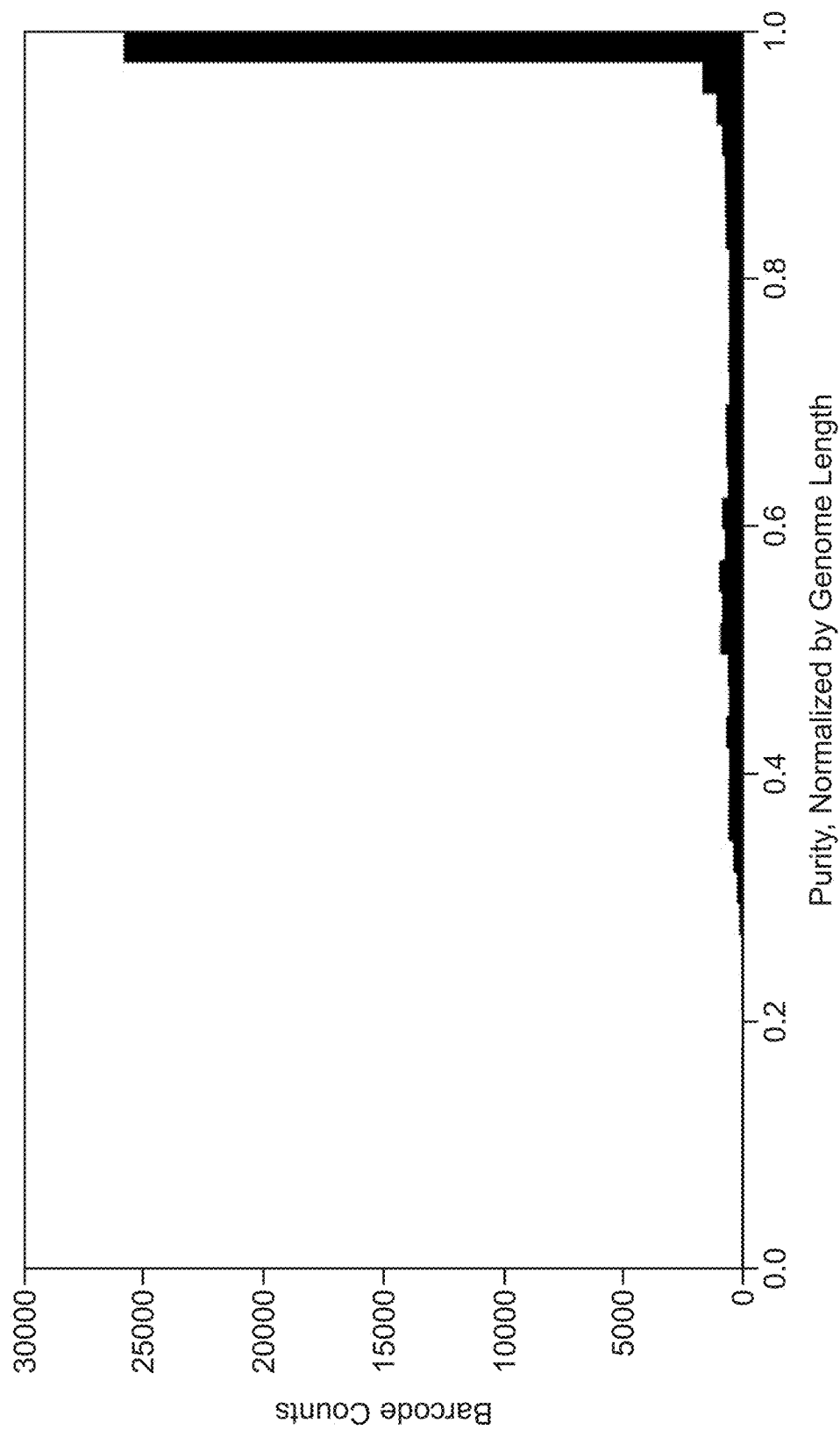
FIG. 12 depicts a plot showing the genome size-normalized purity scores of barcode groups in the 10-cell control experiment. Genome size-normalized purity scores are calculated using the same method using the fraction of the genome sequenced for each respective species rather than the raw number of reads.
Figure 13:
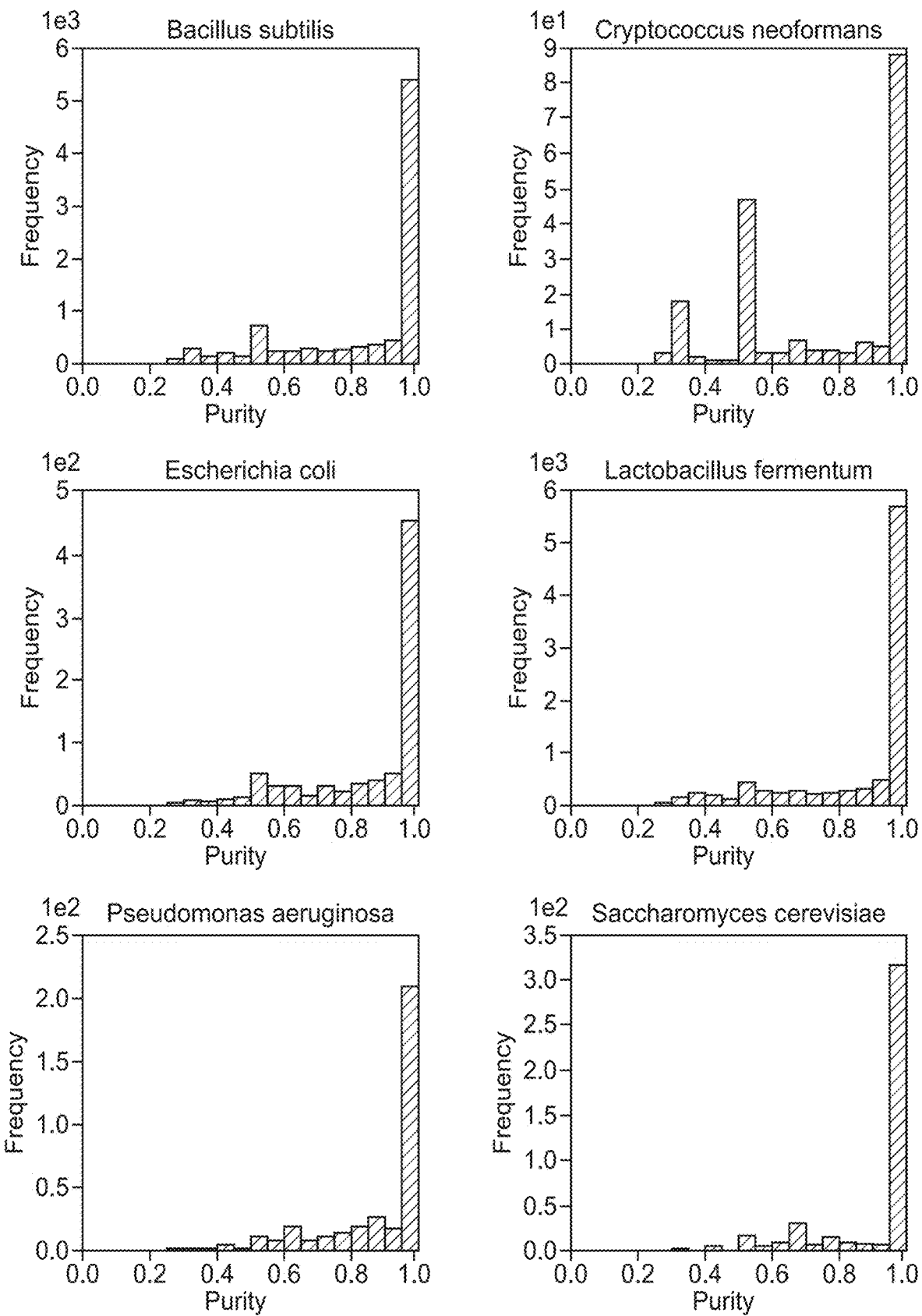
FIG. 13 depicts plots showing the purity scores of barcode groups separately plotted for each species.
Figure 13:
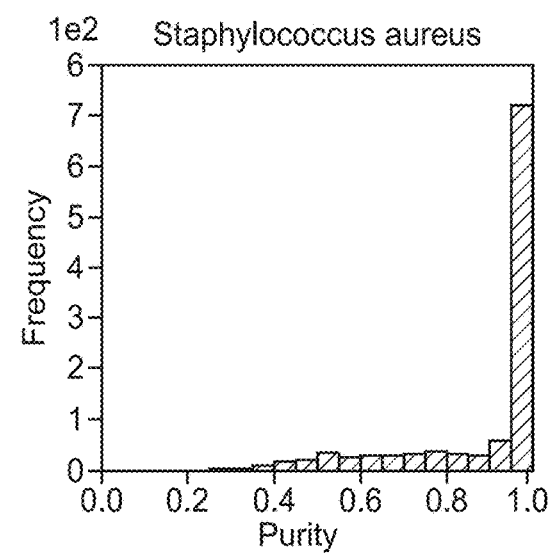
Figure 13:
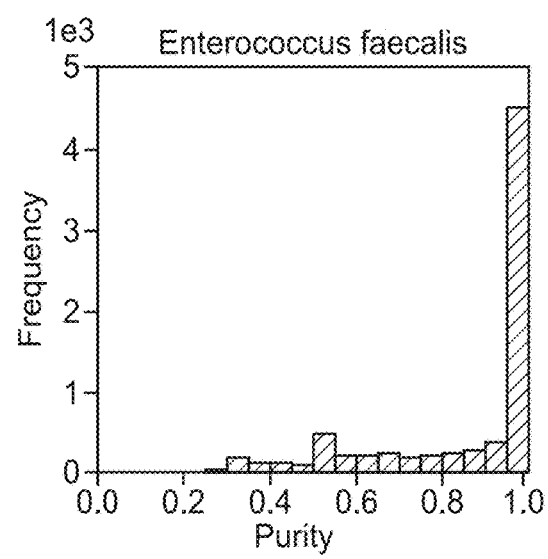
Figure 13:
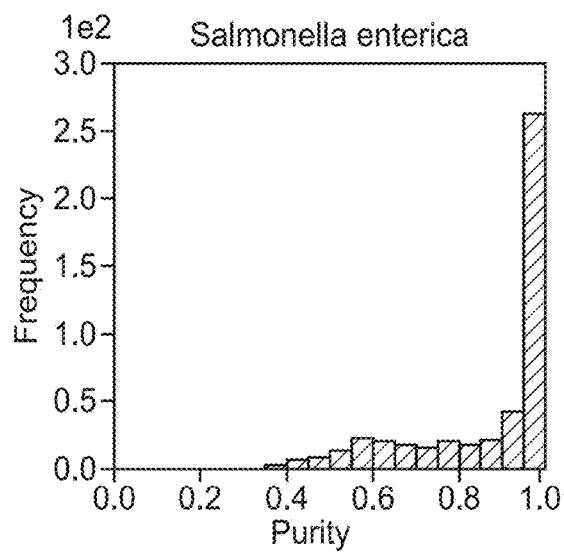
Figure 13:
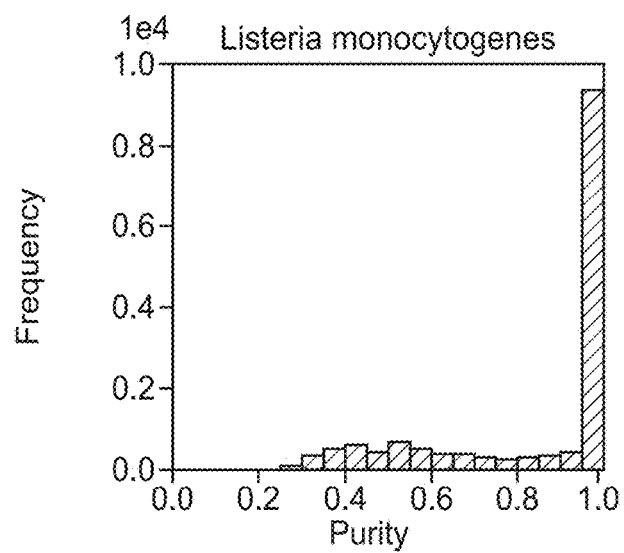
Figure 14:
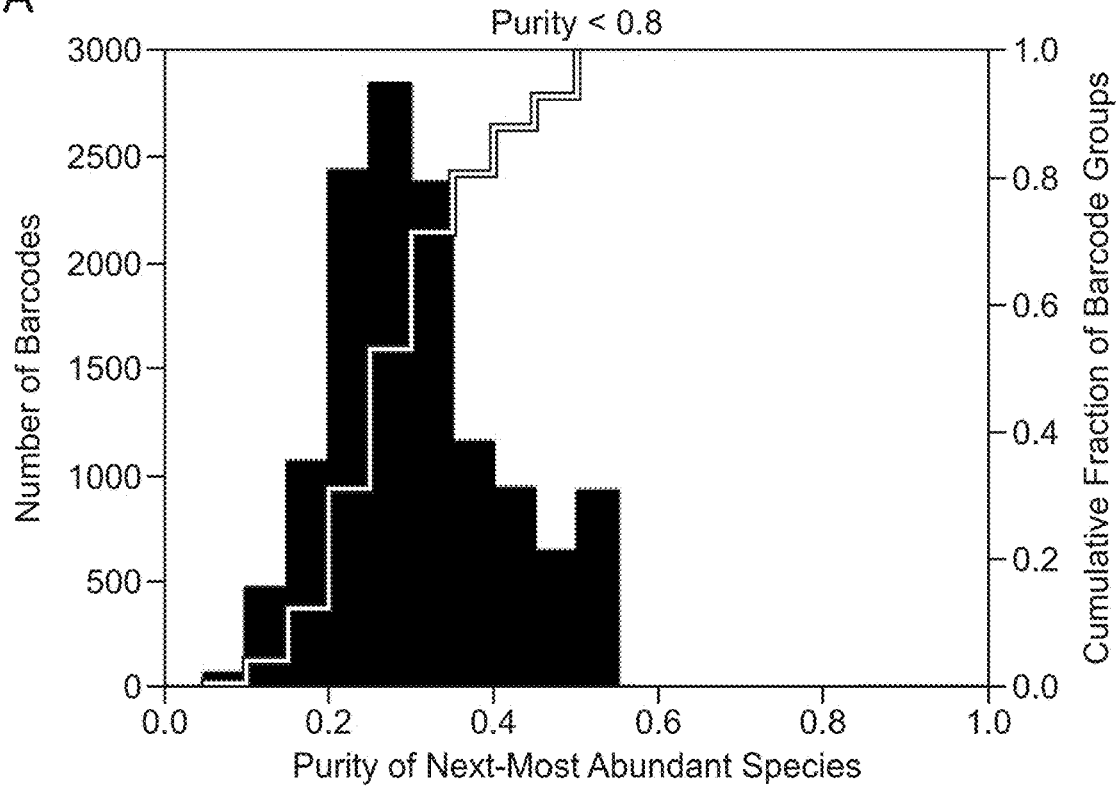
FIG. 14 depicts plots showing the purity scores of the next-most abundant species in a) barcode groups of purity <80%, b) barcode groups of purity >80%. In barcode groups with <80% purity, the purity scores of the next-most abundant species tend to be high from ~20% to 50%, reflecting that those two species represent the majority of the reads in the barcode group, suggesting that these barcode groups represent double encapsulations. Barcode groups with 100% purity are not represented in the plots.
Figure 14:
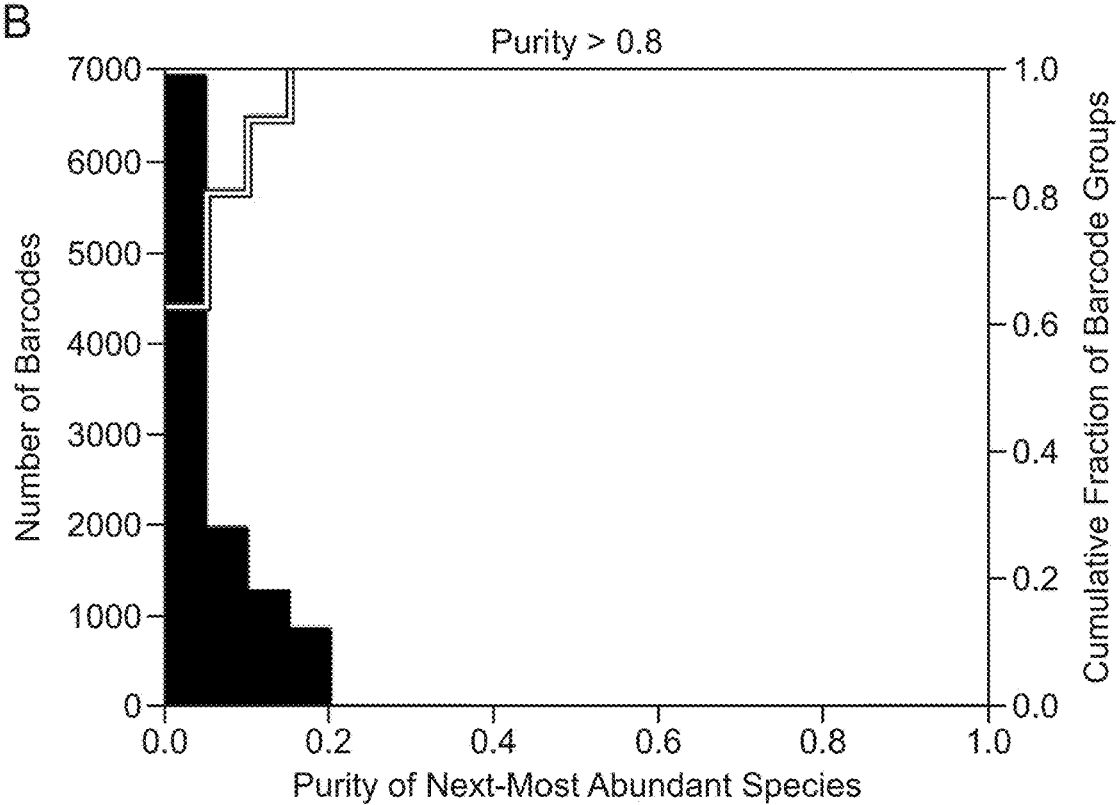

To determine whether the barcode groups indeed correspond to single cells, all reads were mapped to the reference genomes of the three known species. If two microbes reside within the same barcode group, reads will map to both genomes. A group purity score was defined as the fraction mapping to the most mapped reference. The distribution of group purity scores was strongly skewed to high values with the majority of purity score over 95% suggesting that most barcode groups represent single cells; this result is consistent even taking into account the different genome sizes of the ten species (FIG. 5B and FIG. 12) as well as when purity is examined for each individual species (FIG. 13). The rare barcode groups with low (<80%) purity scores were further examined and determined that the majority of those barcode groups represent rare cases where two cells were encapsulated into one droplet, and the occasional coalescence of two single-cell containing droplets (FIG. 14).

Figure 5C:
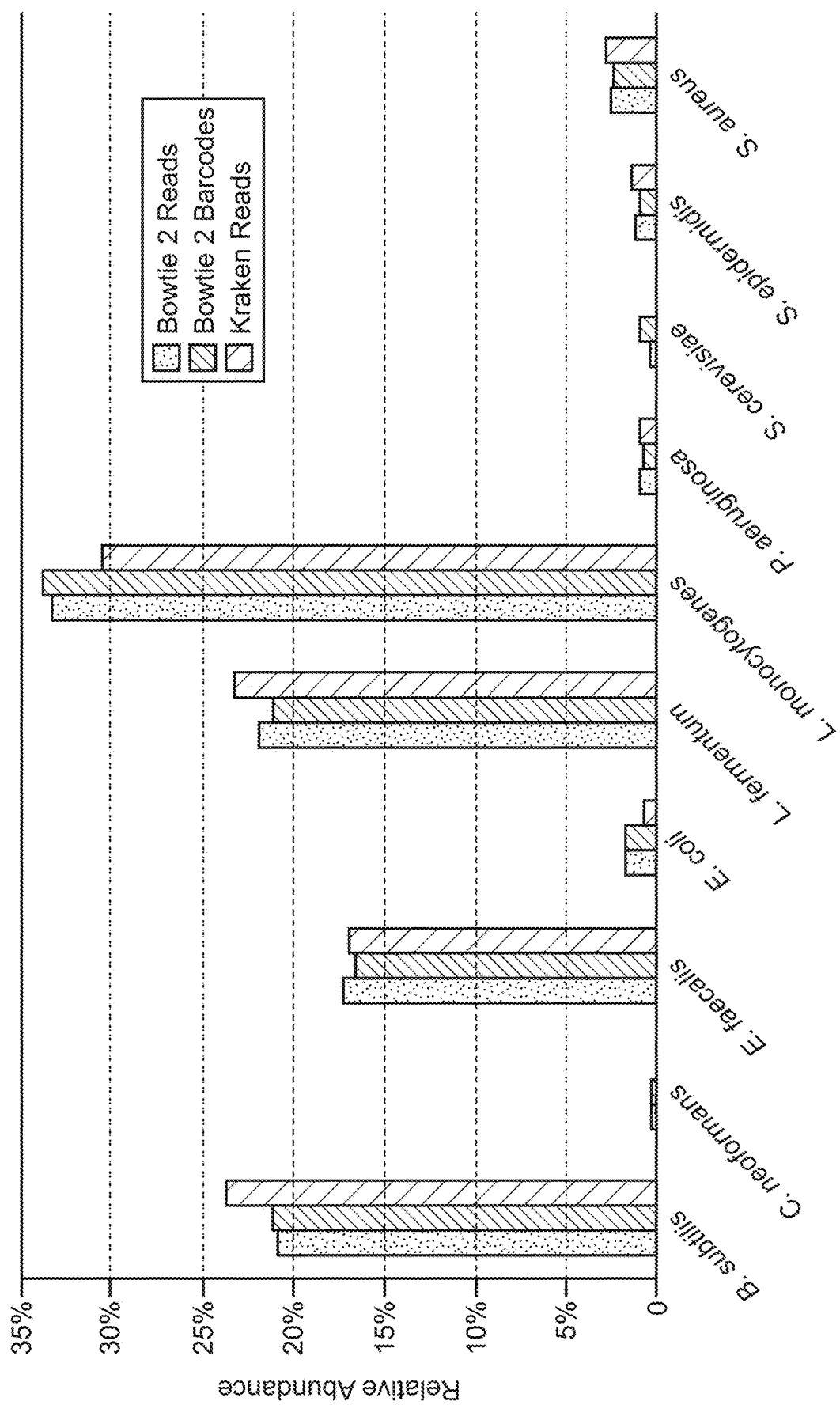
Figure 15:
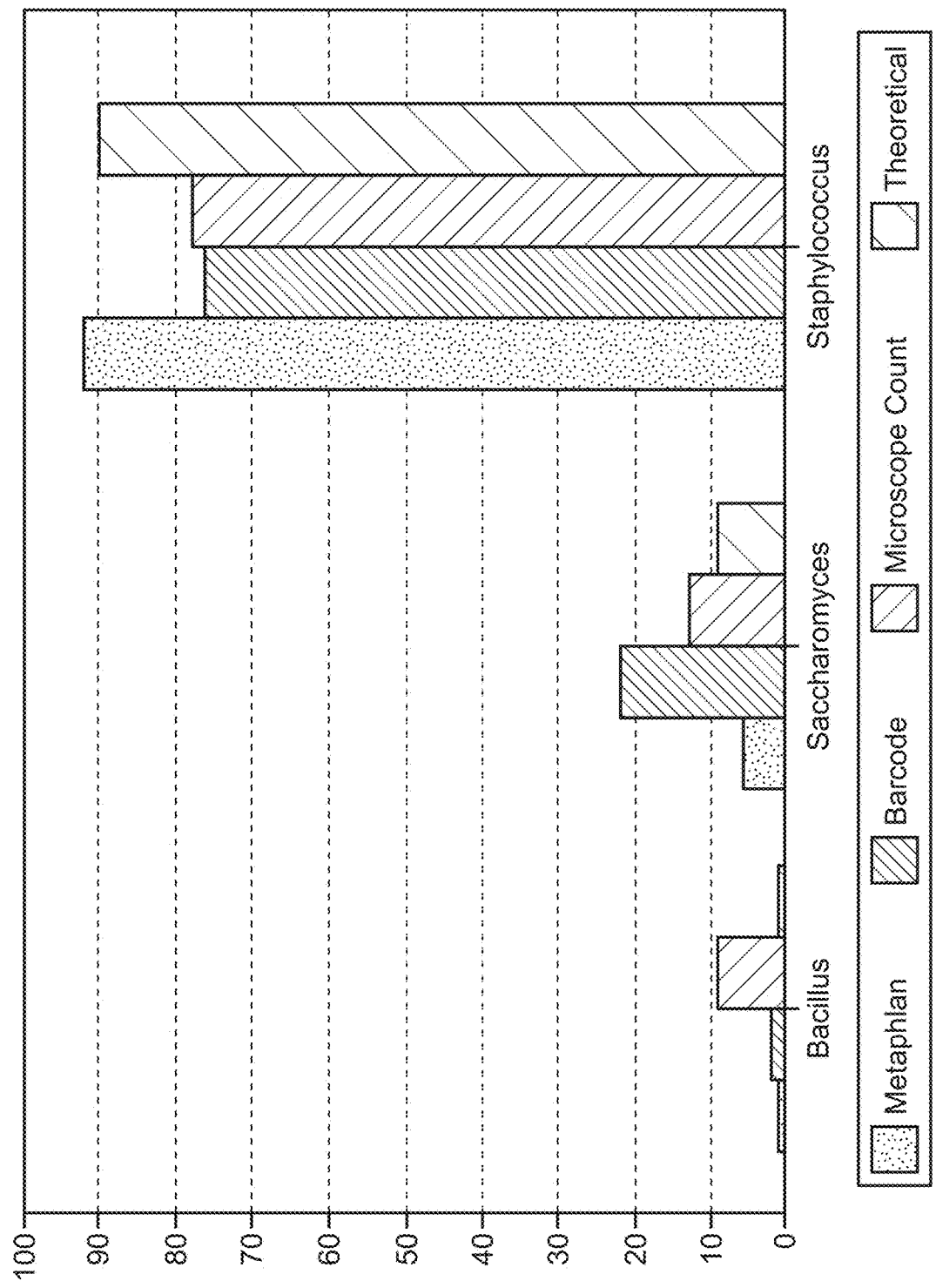
FIG. 15 depicts a plot showing SiC-seq performance on an artificially constructed microbial community consisting of *Staphylococcus, Bacillus,* and *Saccharomyces*. Relative abundance estimates of each species are calculated using from left to right for each species: marker gene counting without barcodes (Metaphlan), barcode counting (Barcode), manual counting under the microscope after cell encapsulation (Microscope count), and while in culture (Theoretical).

To determine whether SiC-seq barcodes abundances reflect the organism abundances in the dataset, abundance estimates calculated via short-read alignment, metagenomic sequence classification, and counting under bright-field microscopy were compared (FIG. 5C and FIG. 15). It was found that all methods are in reasonable agreement when reads are pooled and analyzed in bulk using these methods and also when species identities are assigned to each barcode based on the most commonly mapped species in a group. This demonstrates that SiC-seq enables estimation of species abundance in a microbial population consistent with accepted metagenomic methods.

Figure 5D:
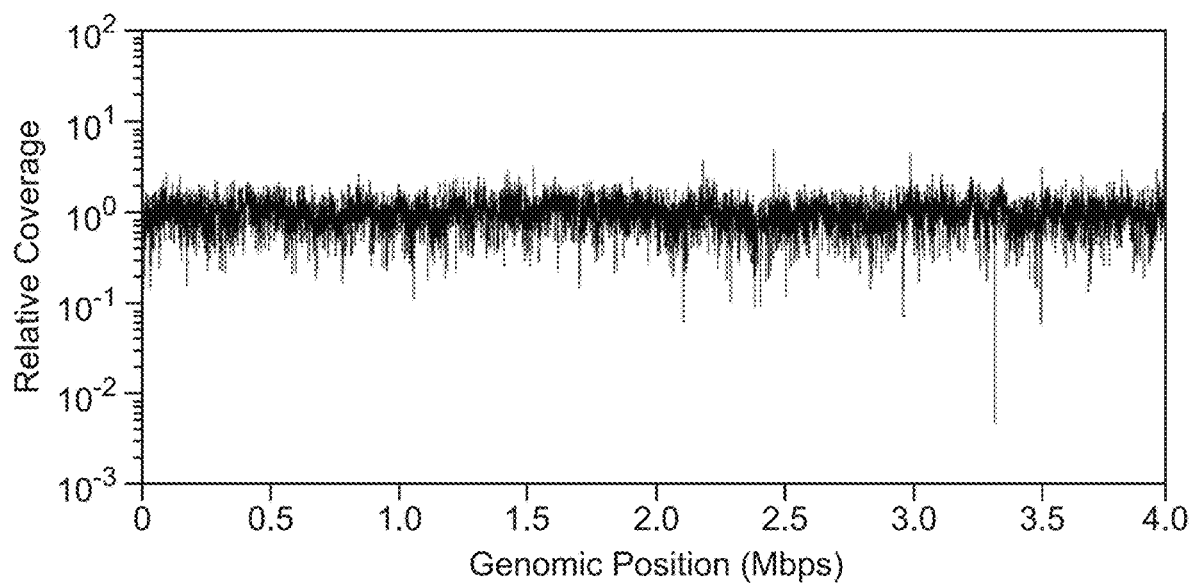
Figure 5E:
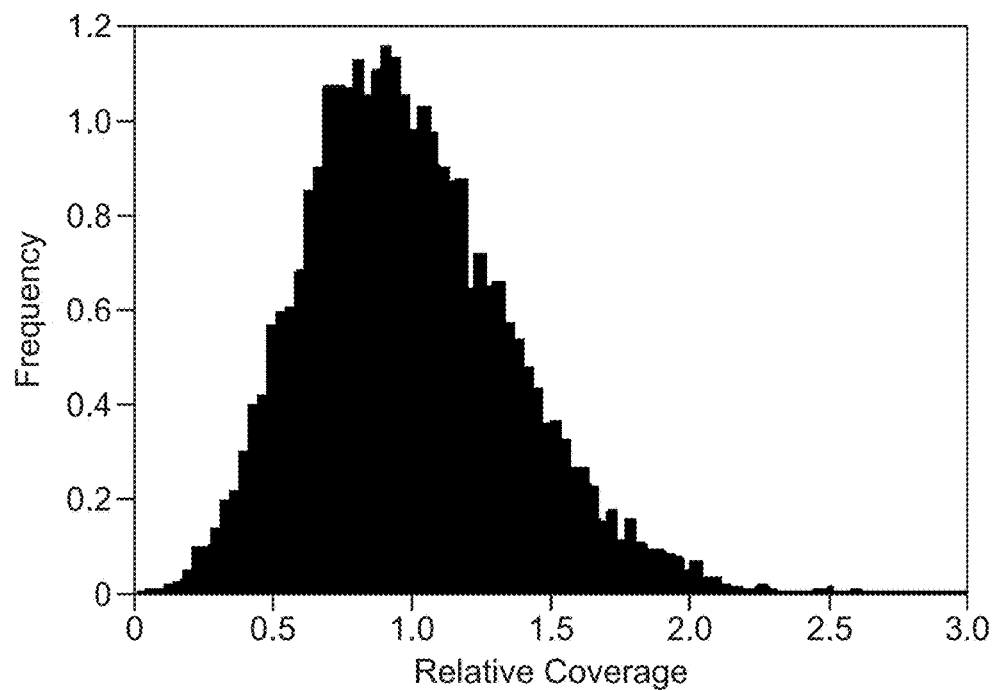
Figure 6A:
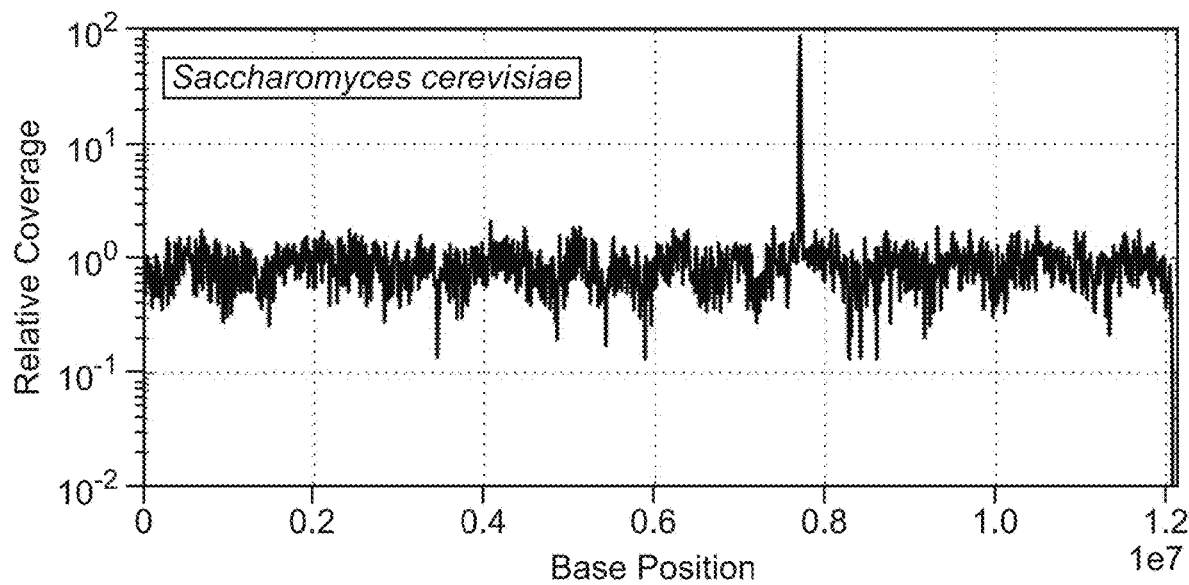
Figure 6A:
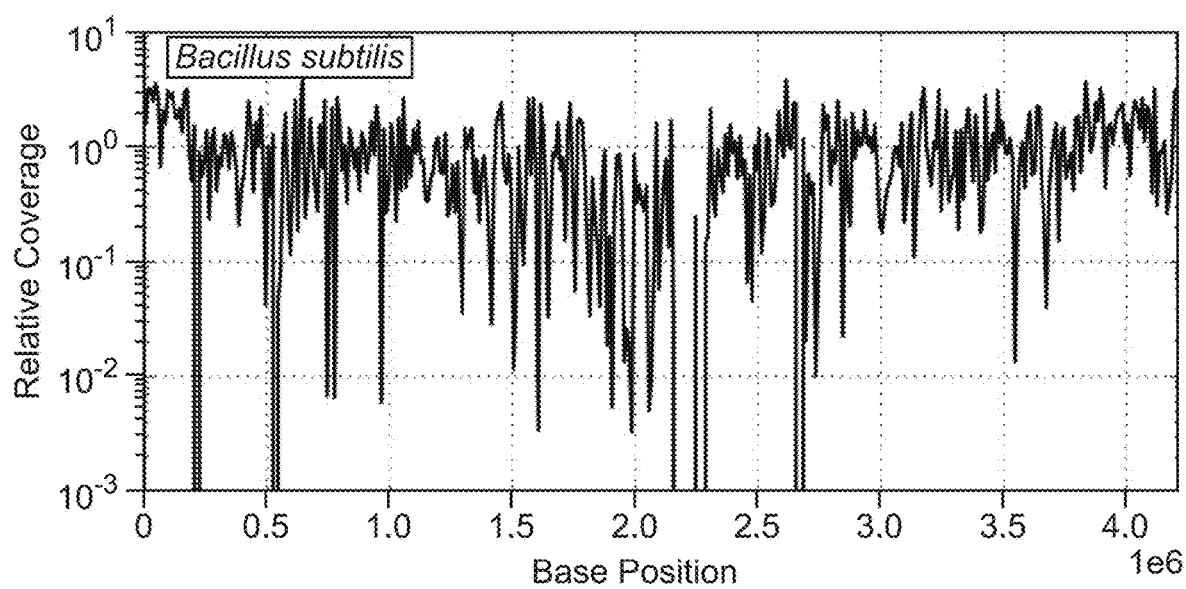
Figure 16:
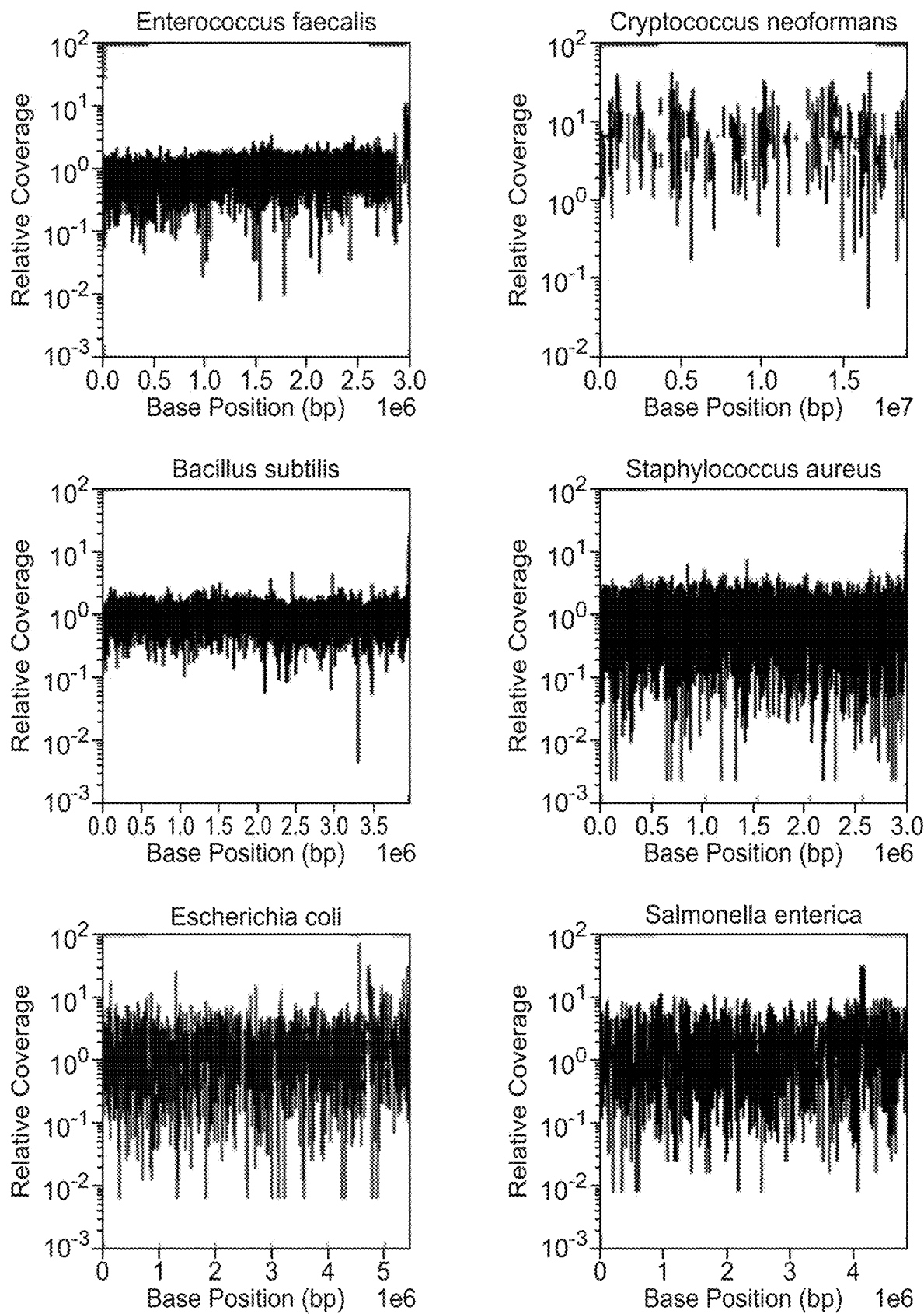
FIG. 16 depicts plots showing the aggregate genomic coverage of all the barcode groups for species in the synthetic microbial community. Species at low abundance show frequent dropouts characterized by dips in the graph, but instances of systematic bias characterized by sharp peaks are rarely observed.
Figure 16:
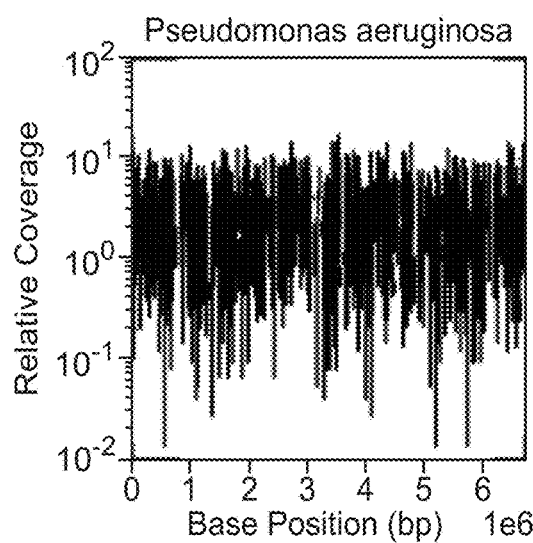
Figure 16:
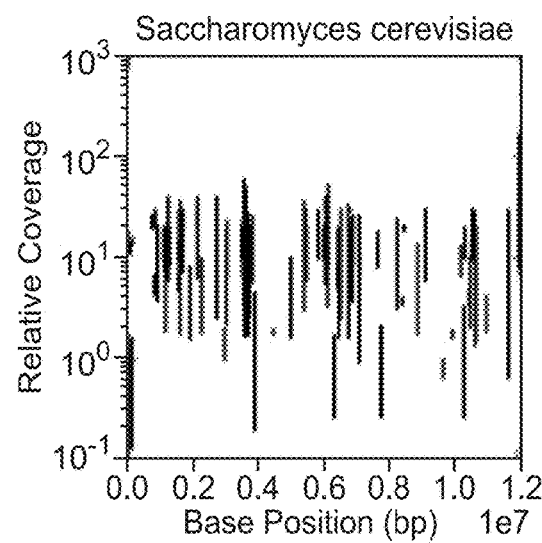
Figure 16:
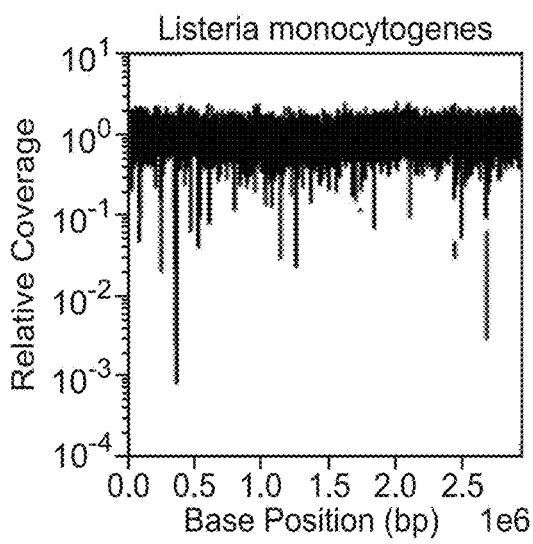
Figure 16:
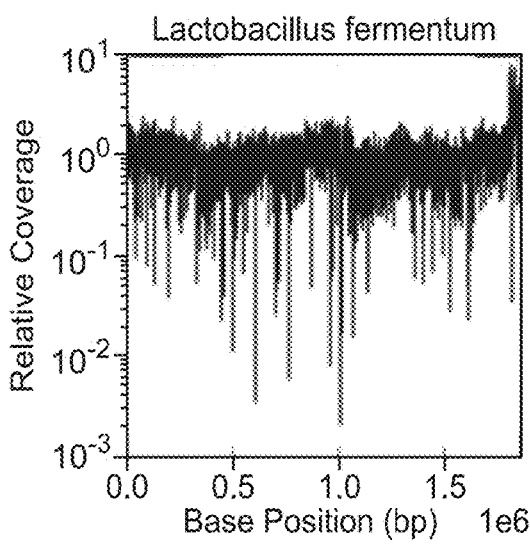

To investigate coverage distribution bias in SiC-seq, the normalized coverage distribution was plotted for reads aggregated from all barcode groups for each microbe (FIG. 5D, FIG. 5E and FIG. 16). With the exception of coverage gaps due to differences between the genomic DNA abundances of cells within the standard microbial community, no significant coverage bias was observed. This indicated that the sampling of each genome within a barcode group was random, so that when all groups were overlaid a uniform distribution was obtained. The distribution of reads in individual barcode groups were further inspected and no significant bias was found (FIG. 6A, FIG. 6B) In addition, bias was minimal because each genome was amplified in a tiny volume of ~65 pL, which has been shown to curtail bias-inducing runaway of exponential amplification. Moreover, the sequencing library was composed of ~50,000 amplified genomes and, as such, the amplification of each genome can be limited by the tiny volume while still producing sufficient total DNA for sequencing.

Figure 7:
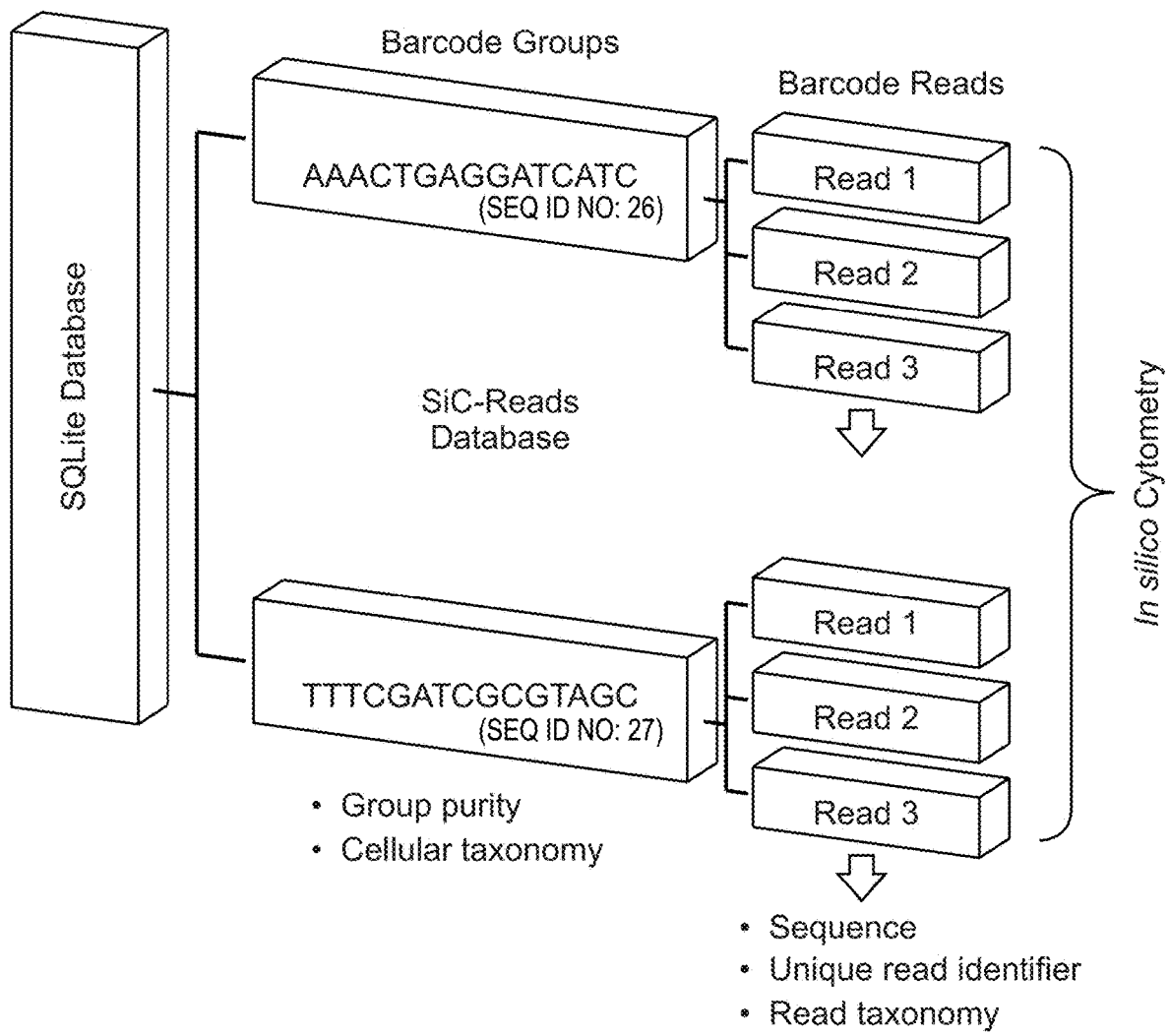
FIG. 7 depicts a schematic illustrating an example framework of a SiC-Reads database. Reads which contain properties such as sequence, read ID, and taxonomy are stored inside barcode groups which contain properties such as purity and taxonomy. Sequences shown are for example purposes only and are not limiting.

SiC-Seq Generates a Novel Type of Data which can be Analyzed Using in Silico Cytometry:

The genomic sequences generated using SiC-seq were grouped by according to single cells, which was complementary to the sequences of short-read metagenomic sequencing. Existing computational tools were ill-suited to analyzing this data, because they do not exploit the single cell barcode information unique to SiC-seq. To address this, a novel sequence analysis pipeline was utilized in which reads are organized hierarchically as barcode groups, generating a Single Cell Reads database (SiC-Reads) (FIG. 7). To build SiC-Reads, raw sequences were filtered by quality, grouped by barcode, and a taxonomic classification of each group was estimated using phylogenetic profilers. A purity score was also estimated based on the reads classifiable by the profiler, assigning a value equal to the fraction of reads mapping to the dominant taxon within the classifiable set. Additional properties of barcode groups and reads, such as presence of sequences corresponding to antibiotic resistance genes, can be added to the database as they are discovered during analysis The massive set of single cell genomes present in SiC-Reads provides new opportunities for discovering associations between sequences within single cells, in a process called in silico cytometry. SiC-Reads include a multidimensional collection of single cell genomes that can be sorted in silico, in analogy to what is commonly done with flow cytometry on single cells. While flow cytometry requires that a target biomarker be selected a priori and is limited in the number of biomarkers that can be used, in silico cytometry can be performed as many times and with as many sequence biomarkers as desired. The database can be sorted repeatedly to mine for correlations between different genetic sequences and structures. Moreover, as new associations are learned, new sorting parameters can be defined, enabling new discoveries without having to repeat the experiment, ultimately limited only by the completeness and accuracy of the single cell database.

Figure 8:
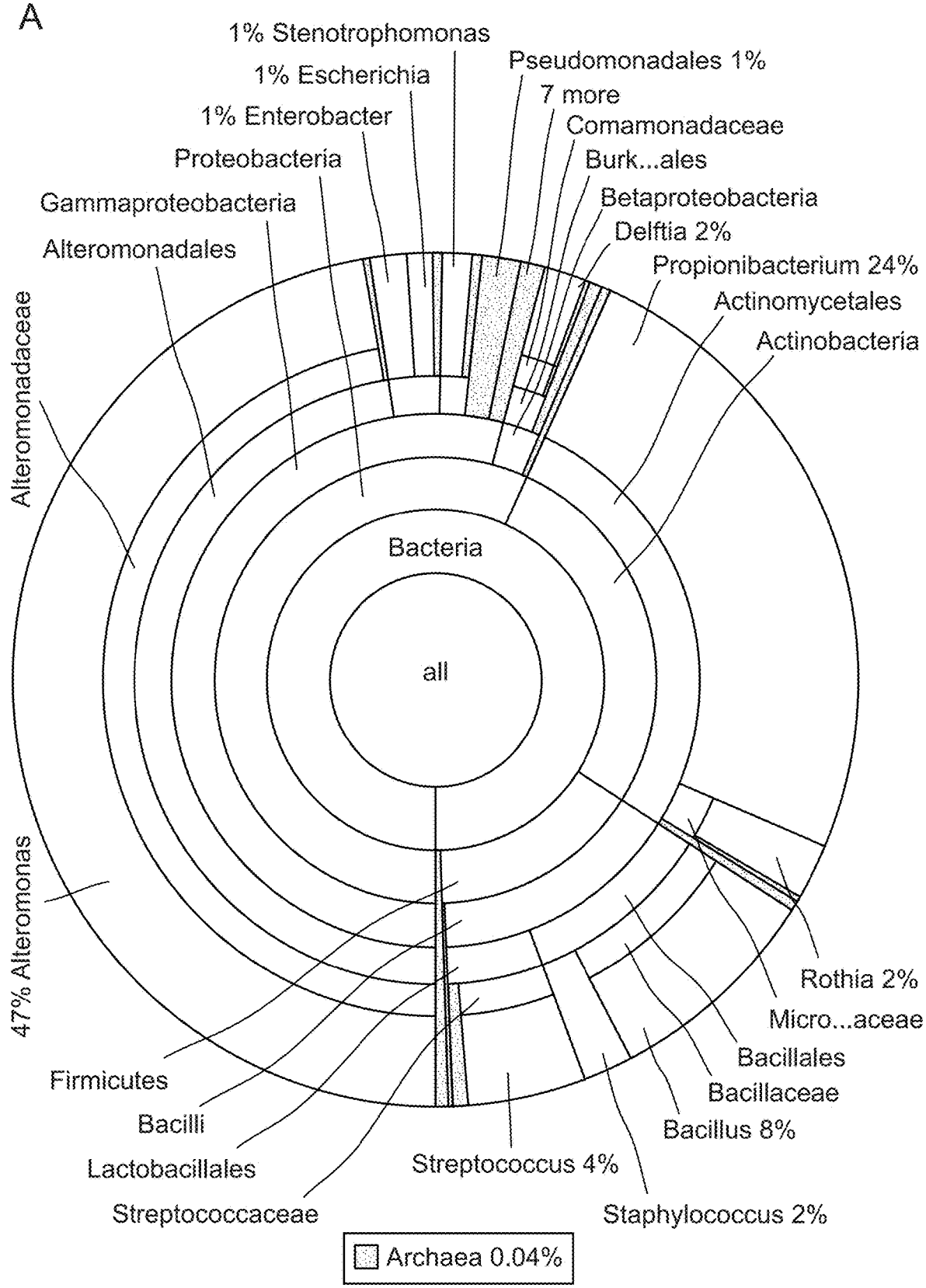
FIG. 8 illustrates the marine microbial community used to demonstrate in silico cytometry as described in the Examples herein. a) Taxonomic abundance of the SiC-Reads database by barcode groups. b) Distribution of purity of barcode groups in the database at the genus level.
Figure 8:
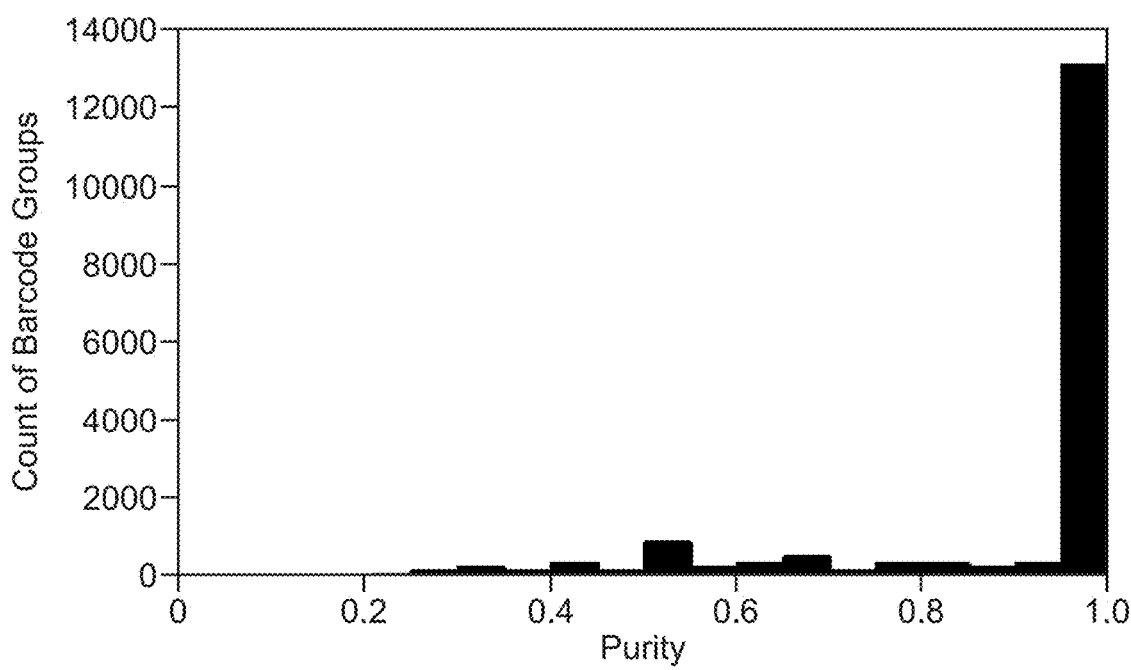

To illustrate the power of SiC-seq and in silico cytometry, a microbial community recovered from coastal sea water of San Francisco was sequenced (see, Materials and Methods). ~8 million reads of 150 bp length was obtained after quality filtering (representing of ~55% of raw reads, with which a SiC-Reads database was generated (FIG. 7). 601,348 (6.89%) of reads were classified into taxa representing 99.8% bacteria, 0.04% archaea, and 0.16% viruses (FIG. 8, Panel A). Barcode groups were assigned a taxonomic classification based on the reads they contained, following the rule that more than 10% of reads must have a classification, and the group is classified according to the taxon with the most supporting reads. Most barcode groups were estimated to be high purity based on the classifiable sequences (~91%), in accordance with the control sample (~94%) (FIG. 8, Panel B). Using this data, in silico cytometry was demonstrated by exploring the distribution of antibiotic resistance, virulence factors, and phage sequences in the microbial community.

Taxonomic Distribution of Antibiotic Resistance in Microbes Inhabiting the San Francisco Coastline:

Antibiotic resistance (AR) has become increasingly common and represents a significant threat to global human health. Because antibiotics are the primary tool for fighting bacterial infections, understanding how AR genes spread in the natural environment is essential to maintaining effective counter-measures for bacterial diseases. Microbes can gain AR through numerous mechanisms, including mutation, acquisition of resistance-conferring genes, or even deletion of genes. While AR genes can be identified in most environments by short-read sequencing, scant information on how they are distributed among taxa is available, because obtaining this information usually requires testing or whole genome sequencing of single species; however, most species are uncultivable, precluding such analyses.

SiC-seq provides a unique opportunity to characterize the distribution of AR genes amongst all species in a sample, including uncultivable ones because species can be classified based on reads in the barcode group, and then associated with AR genes also present. To determine the distribution of AR genes among taxa in the dataset, the SiC-Reads database was searched for known AR genes, and 1,081(0.012% of reads) were found, representing 108 (0.30%) of barcode groups. The taxonomic distribution of AR genes had a clear structure (FIG. 9A and FIG. 10, Panel A); differences are expected in the natural coastline environment compared to the environment of the isolated and sequenced strains. The most abundant taxa associated with AR were not the most abundant community members overall, suggesting that in this community certain taxa tend to associate more with AR genes. For example, Aminoglycoside resistance was primarily found in *Alteromonas* spp., while Beta lactam resistance was widely spread, found in 4 out of 5 taxa. While not intending to be bound by any particular theory, it is possible that the broad-spectrum activity of Beta-lactams has encouraged their heavy use by humans and, correspondingly, has resulted in widespread resistance in the costal microbes of San Francisco. Aminoglycoside antibiotics, on the other hand, are not commonly used by humans and, thus, resistance against them is rare, with identified instances possibly representing genes naturally found in *Alteromonas* where its primary purpose is not to avoid Aminoglycoside antibiotics mediated killing.

Associating Virulence Factors with Host Bacteria in a Microbial Community:

Virulence factors (VFs), like AR genes, are important in determining the threat that specific microbes pose to human health. Many opportunistic pathogens reside in natural communities in the environment and cause outbreaks when transmitted to a suitable host. Therefore, monitoring and detecting potentially pathogenic microbes is important for public health. While metagenomics shotgun sequencing or DNA microarray methods can detect the abundance of VFs in a community, they cannot determine which microbes carry them, or whether multiple VFs are present in the same microbes—both of which are important determinants for the pathogenic potential of a species. Here, again, SiC-seq affords a unique opportunity to characterize VFs in a community and to associate them with specific host species.

The coastal microbial community database was searched for known VF genes, and yielded matches in 1,949 (0.022%) reads in 101 (0.28%) barcode groups consisting of 29 prevalent VFs distributed among 13 microbial genera. The abundances of taxa with VFs did not reflect that of the total population, suggesting that certain genera tend to carry more VFs than others. To quantify this, the VF ratio was calculated, the ratio between the number of barcode groups containing VFs and the total number of barcodes in the community for that species, and the results were normalized to the highest VF ratio for comparison (FIG. 9B). *Haemophilus* and *Escherichia* stood out amongst all species, both of which are known opportunistic human pathogens. Upon closer inspection, the main VFs detected in *Haemophilus* were lipooligosaccharides, which are the major constituents of *Haemophilus* outer membranes and an important determinant of host immune evasion. In *Escherichia*, the main VFs detected are the K1 capsule and Type III secretion system, both commonly present in virulent strains. Comparing the VF ratios of the San Francisco coastline community with ones calculated for publically-available whole genomes, and down sampled to match the per-cell read depth (FIG. 10, Panel B), the ratios were found to be higher for the public genomes, indicating a bias towards pathogenic strains in currently-sequenced genomes.

Determining Transduction Potential Between Bacteria in a Microbial Community: Many virulent bacterial strains are thought to arise from horizontal gene transfer aided by cross-infection of bacteriophages. Phages can modify the genomes of their hosts, leaving a copy of their own genome behind, or transporting fragments of one species to another in a process thought to be an important mechanism for generating virulent bacterial strains, known as transduction. Nevertheless, as with AR and VF genes, characterizing the distribution of these mobile elements is challenging in an ecological context because confident identification of foreign genomic fragments within a specific host requires sequencing cultures of single species or single cells. Nevertheless, this information is extremely valuable for understanding how bacteria transfer genetic material in general, and how virulent new strains may emerge via this mechanism in particular.

Figure 9C:
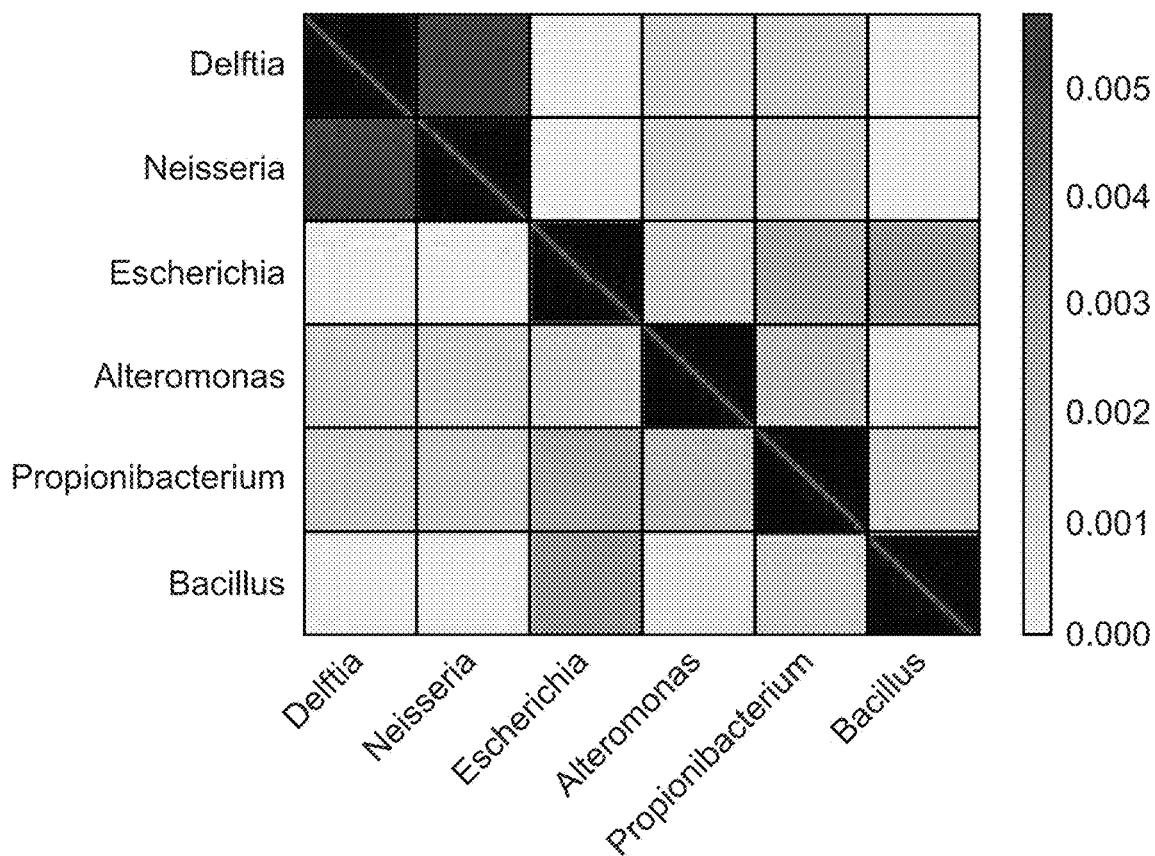

To explore transduction in the microbial community, the SiC-Reads database of the San Francisco coastal community was searched for barcode groups containing phage sequences. A phage sequence found in a bacterial genome is evidence that it could potentially infect the host, an association that is normally extremely difficult to make for uncultivable microbes and their likely uncultivable infecting phages. Matches were found in 6,805 (0.078%) reads representing 260 (0.72%) barcode groups and 106 phage genomes. Since transduction can occur between two host cells infectable by the same phage, the potential for transduction depends on how many types of phages infect both hosts, and how often these phages infect both taxa. To visualize this, the sum of the number of times the sequences matching to the same phage in two bacterial taxa was detected were plotted, normalized by the number of barcode groups in those genera (FIG. 9C). According to this analysis, Delftia and *Neisseria*, which are closest related out of the taxa in this analysis, have the highest potential for transduction. Nevertheless, SiC-seq's ability to detect these sequences and correlate them within single genomes provides a novel and powerful approach for studying phage-host interactions. Such interactions are understudied due to the lack of high throughput methods with which to sequence single cells but critical to understanding microbial community dynamics.

Example 2: Microfluidic Barcoding of Single-Cells by MALBAC Reaction

In this example, a synthetic community of cells with known composition is used to evaluate amplification and barcoding performance. Cells encapsulated in hydrogels may be used in the place of the cell suspension described in this procedure.

Materials and Methods:
Microfluidic Devices:
To fabricate the microfluidic devices, poly(dimethylsiloxane) (Dow Corning, Sylgard 184) was poured over a negative photoresist (MicroChem, catalog no. SU-8 3025) patterned on a silicon wafer (University Wafer) using UV photolithography. The PDMS devices were cured in an oven for 1 hour, extracted with a metal scalpel, and punched with a 0.75 mm biopsy core (World Precision Instruments, catalog no. 504529) to create inlets and outlets. Devices were bonded to a glass slide using an oxygen plasma cleaner (Harrick Plasma) and the channels treated with Aquapel (PPG Industries) and baked at 80° C. for 10 min to render them hydrophobic.

Barcode Emulsions:
Barcode emulsions were prepared through asymmetric digital PCR process wherein barcode oligonucleotides were amplified as single molecules in droplets containing PCR reagents. The asymmetric PCR favors production of single-stranded barcode products. Barcode oligonucleotide BD23 (GTATGCGACTTCAGTACATCGTCCCGATGCTC-TGCACAGTCGACCGCTGANNNN NNNNNNNNNN-NCAGCGATCCCGAGTCAGATCGATGCCACTGA-GACCTGTGAGTG ATGGTTGAGGTAGTGTGGAG) (SEQ ID NO:9) (IDT) at 0.01 pM concentration was added to a PCR reaction mix containing 1×NEB Phusion Hot Start Flex Master Mix (NEB, catalog no. M0536L), 2% (v/v) Tween 20 (Sigma-Aldrich, catalog no. P9416), 5% (w/v) PEG-6000 (Santa Cruz Biotechnology, catalog no. sc-302016), 0.2 µM limiting primer BD27 (CTCCACAC-TACCTCAACCATCACTCACAGGTCTCAGTGGC) (SEQ ID NO:10), and 1 µM excess primer BD28 (GTATGCGACTTCAGTACATCGTCCCGATGC-TCTGCACA) (SEQ ID NO: 11) (IDT). The PCR mixture and HFE-7500 fluorinated oil (3M) with 2% (w/w) PEG-PFPE amphiphilic block copolymer surfactant (008-Fluoro-surfactant, Ran Technologies) were loaded into separate 1 mL syringes (BD) and injected at 300 and 500 µL/hr, respectively, into a co-flow droplet maker (FIG. 21) using syringe pumps (New Era, catalog no. NE-501) controlled with a custom Python script ("https:" followed by "//github." followed by "com/AbateLab/Pump-Control-Program"). The emulsion was collected in PCR tubes, and the oil underneath the emulsion removed via pipette and replaced with FC-40 fluorinated oil (Sigma-Aldrich, catalog no. 51142-49-5) with 5% (w/w) PEG-PFPE amphiphilic block copolymer surfactant for improved thermal stability. The emulsion was thermal cycled (Bio-Rad, T100) with the following program: 98° C. for 3 min, followed by 40 cycles with 2° C. per second ramp rates of 98° C. for 10 s, 63° C. for 20 s, and 72° C. for 20 s, followed by a hold at 12° C. Fluorescent DNA staining using 10× SYBR Green I (Thermo Fisher Scientific) in HFE-7500 oil was used to quantify barcode encapsulation rate under a fluorescent microscope (Life Technologies, catalog no. AMAFD1000).

Preparation of Cell Suspension:
To prepare the artificial community for processing through the SiC-seq workflow, the frozen stock of cells (Zymo Research, catalog no. D6300) were thawed gently in a room-temperature water bath. Cell concentration was determined by manual cell counting under a microscope, and diluted to an appropriate concentration for single cell encapsulation. The calculated volume of cell solution was transferred to a 1.5 mL centrifuge tube (Fisher Scientific) and washed twice in 1 mL PBS. The cells were re-suspended in a 1 mL solution of 1 mM Tris-HCl pH 8.0 (Teknova).

Figure 21:
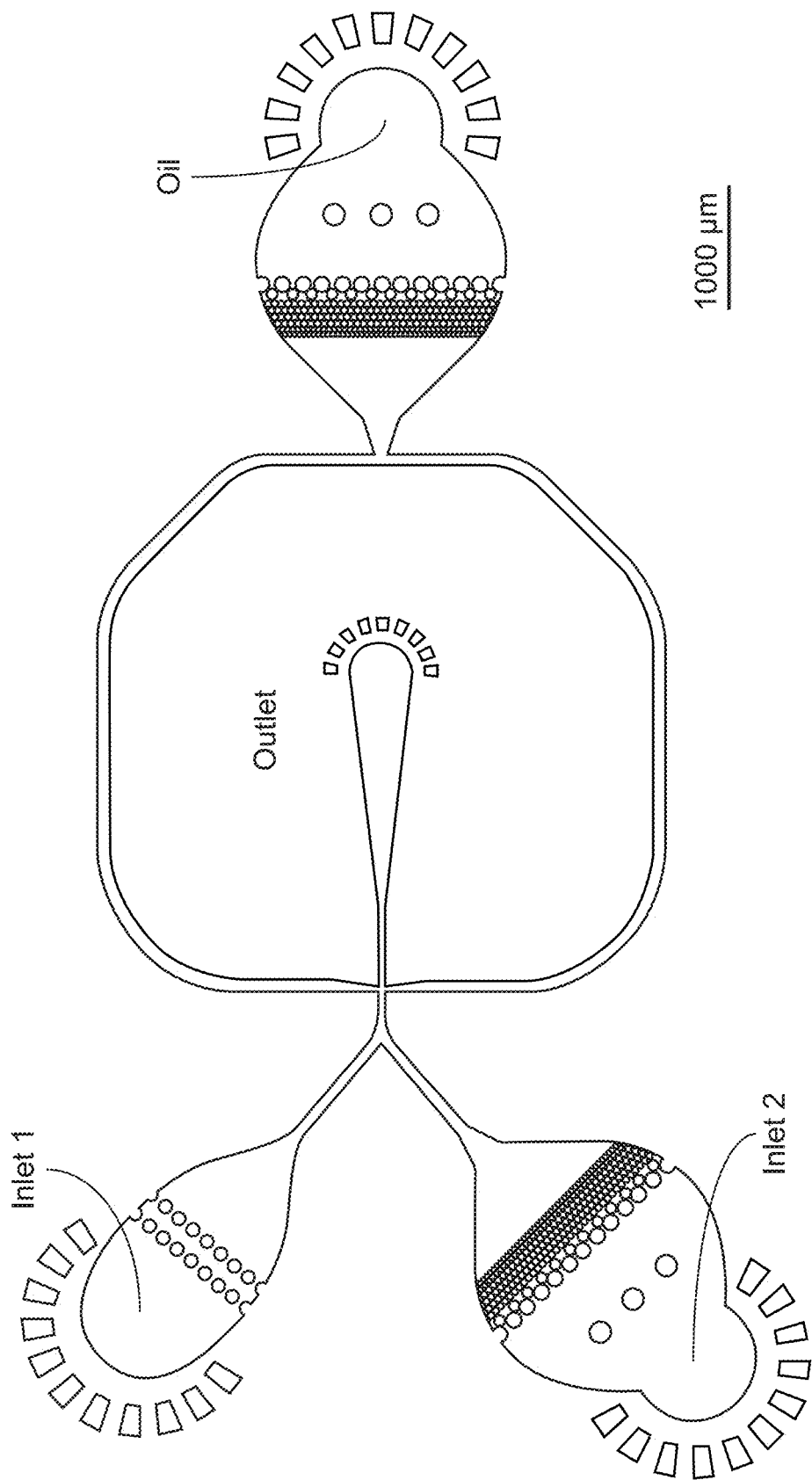
FIG. 21 provides a schematic of a microfluidic device for generation of 30 m water-in-oil emulsions containing a mixture of two aqueous phases. For digital barcode droplet generation, the device is operated with Inlet 1 plugged.

MALBAC Amplification of Single Cells:
MALBAC amplification mix was prepared containing 2× ThemoPol Buffer (NEB, catalog no. B9004S), 2% (v/v) Tween 20, 6% (w/v) PEG-6000, 1.2 mM dNTPs (NEB, catalog no. N0447S), 0.64 pM GAT-8N primer (GTGAGT-GATGGTTGAGGTAGTGTGGAGNNNNNNNN) (SEQ ID NO: 1) (IDT), 4 mM MgSO$_4$ (NEB, catalog no. B1003 S), and 0.12 U/µL Deep Vent (exo-) polymerase (NEB, catalog no. M0259S). The MALBAC amplification mix, cell suspension, and HFE-7500 fluorinated oil (3M) with 2% (w/w) PEG-PFPE amphiphilic block copolymer surfactant were loaded into separate 1 mL syringes and injected at 200, 200, 1000 µL/hr, respectively, into a co-flow droplet maker (FIG. 21). The emulsion was collected in PCR tubes, and the oil underneath the emulsion removed via pipette and replaced with FC-40 fluorinated oil with 5% (w/w) PEG-PFPE amphiphilic block copolymer surfactant for improved thermal stability. The emulsion was thermal cycled (Bio-Rad, T100) with the following program: 95° C. for 5 min, followed by 8 cycles of 20° C. for 50 s, 30° C. for 50 s, 40° C. for 45 s, 50° C. for 45 s, 65° C. for 4 min, 95° C. for 20 s, and 58° C. for 20 s, followed by a hold at 12° C. Although this particular example did not use hydrogels, it is noted that hydrogels could have been integrated into the workflow in the place of the cell suspension.

Figure 22:
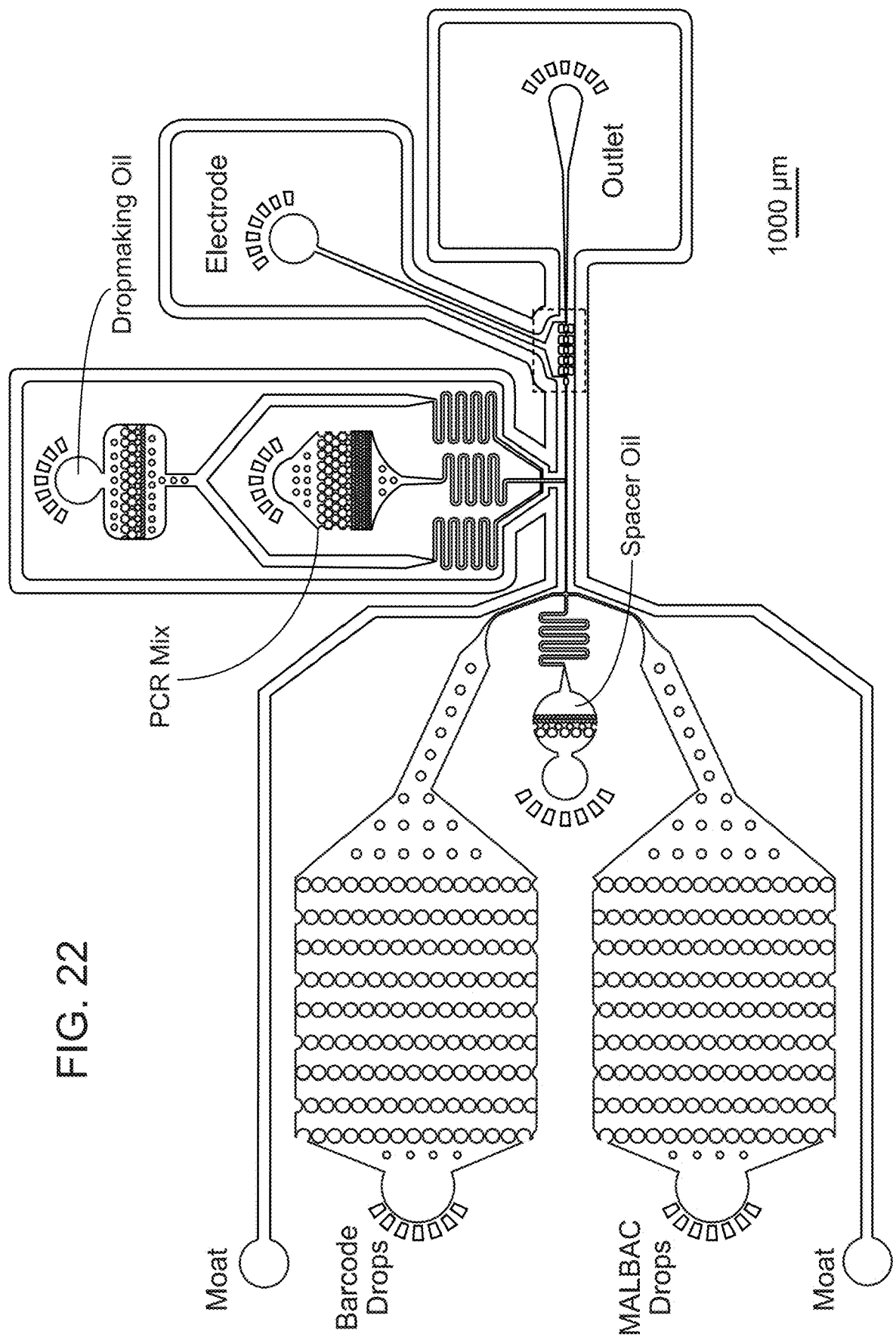
FIG. 22 provides a schematic of a microfluidic device for merger of a MALBAC-amplified cell droplet with a digital PCR barcode droplet. The shaded rectangle indicates the merger region where droplets subjected to a high electric field gradient merge.

Microfluidic Barcoding of Amplified Cells:

MALBAC-amplified cell droplets, barcode droplets, and 300 µL of extension solution containing 1× ThemoPol Buffer, 1% (v/v) Tween 20, 3% (w/v) PEG-6000, 0.5 mM dNTPs, 2 mM MgSO$_4$, and 0.06 U/pL Deep Vent (exo-) polymerase were each loaded into a 1 mL syringe and injected into the merger device as shown in FIG. 22. HFE-7500 fluorinated oil with 2% (w/w) 008-Fluorosurfactant was used as the continuous phase of the emulsion. Merger of the barcode and cell droplet emulsions was achieved using an electrode connected to a cold cathode fluorescent inverter and DC power supply (Mastech). A voltage of 2.0 V at the power supply produced a ~2 kV AC potential at the electrode which causes touching droplets to merge. The emulsion was collected in PCR tubes and the HFE-7500 replaced with FC-40 with 5% (w/w) 008-Fluorosurfactant prior to single-cycle PCR with the following protocol: 95° C. for 2 mins, 55° C. for 30 s, 72° C. for 5 min, and then 12° C. hold. After thermal cycling, the emulsion was broken by addition of 20 µL of perfluorooctanol and brief centrifugation in a micro-centrifuge. The upper aqueous phase was collected and the DNA library was purified and primers were removed using Agencourt AMPure XP beads (Beckman Coulter) at a 0.5× volume ratio of beads to PCR product. The large bead-bound DNA fragments were eluted in water.

Digestion of Single-Stranded Hairpin Loops:

Single-stranded MALBAC amplicons without a barcode were digested by mung bean nuclease, an endonuclease selectively targeting ssDNA. A digestion reaction was prepared containing the barcoded PCR product, 1× mung bean nuclease reaction buffer (NEB, catalog no. M0250S), and 0.033 U/µL mung bean nuclease (NEB, catalog no. M0250S). The reaction was incubated at 30° C. for 30 min and then stopped by addition of 0.5% (w/v) sodium dodecyl sulfate (Sigma-Aldrich) to a final concentration of 0.02% (w/v). A size selection with Agencourt AMPure XP beads at a 0.5× volume ratio of beads to PCR product was performed to remove small digestion products.

Figure 23:
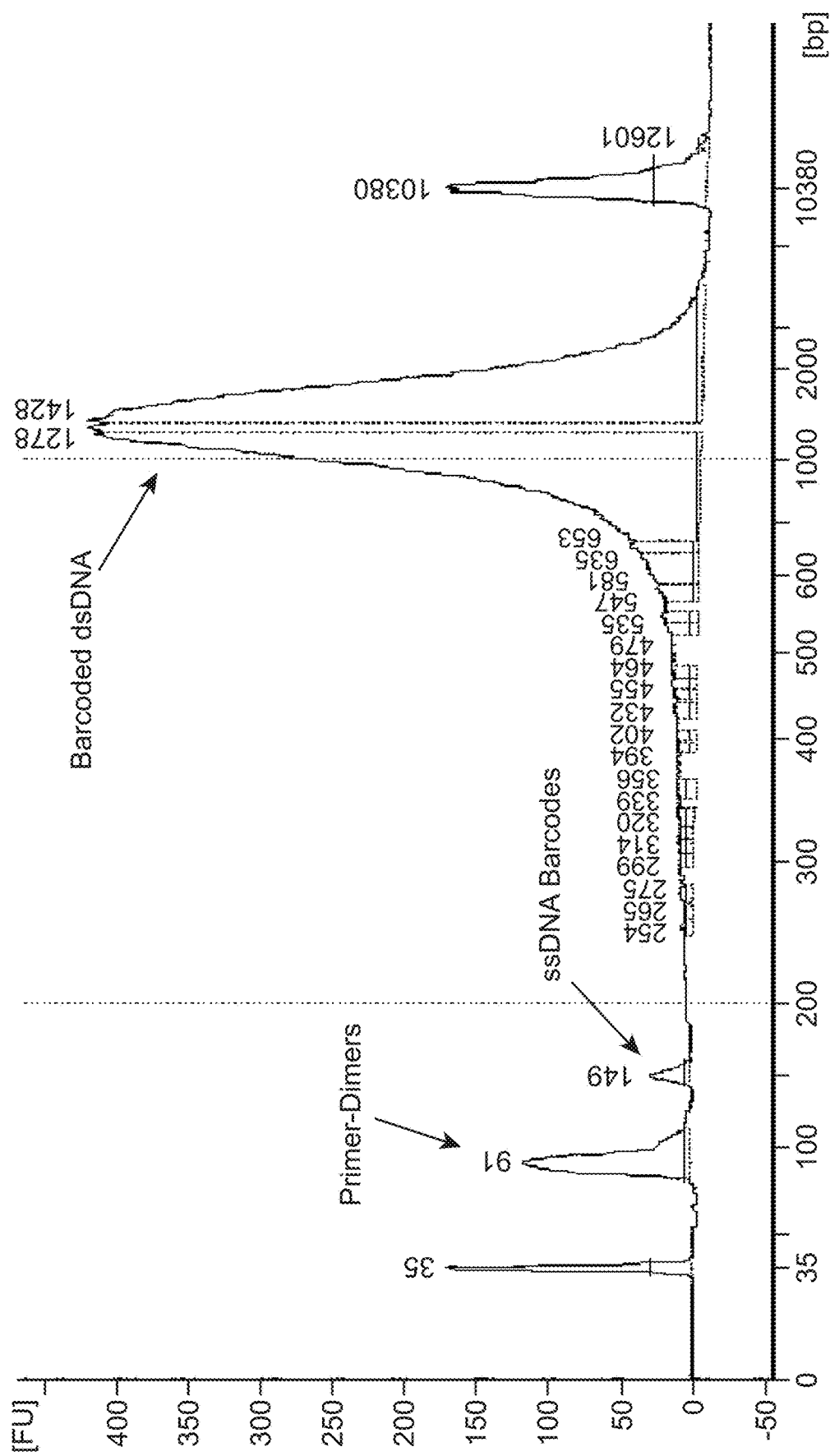
FIG. 23 provides a representative electropherogram of DNA products resulting from an exemplary MALBAC barcode fusion reaction (before size-selection).
Figure 24:
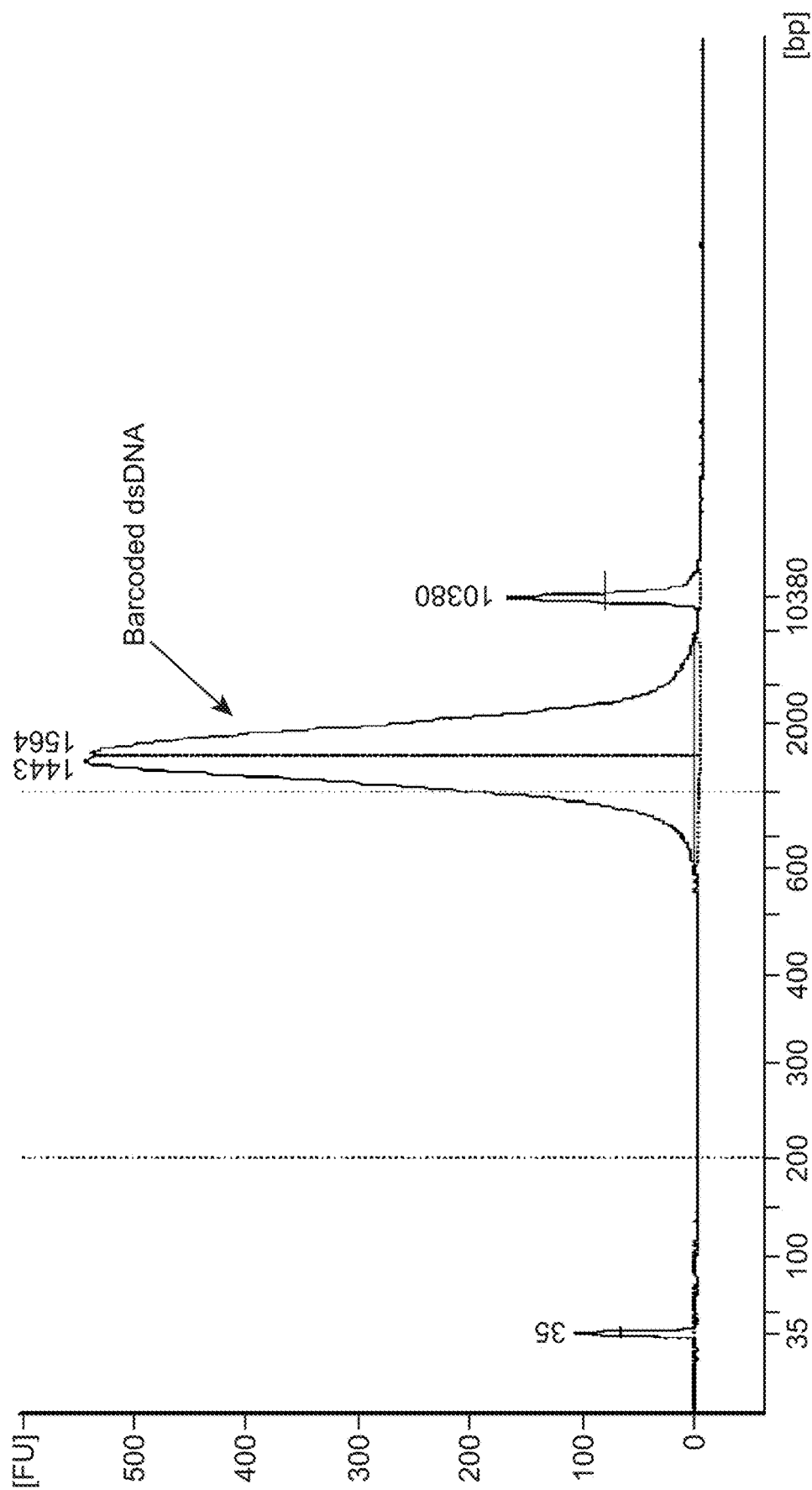
FIG. 24 provides a representative electropherogram of DNA products resulting from an exemplary MALBAC barcode fusion reaction (after size-selection).

Enrichment PCR of Barcoded Genomic DNA:

The barcoded DNA product from the digestion reaction was amplified by PCR in a solution containing 1× Invitrogen Platinum Multiplex PCR Master Mix (Thermo Fisher Scientific, catalog no. 4464268), 0.5 µM GAT-COM primer (GTGAGTGATGGTTGAGGTAGTGTGGAG) (SEQ ID NO:2) (IDT), and 0.5 M BD24 primer (GTATGCGACTTCAGTACATCGTCCCGATGCT-CTGCACAGTCGACCGCTGA) (SEQ ID NO: 12) (IDT) using the following protocol: 95° C. for 1 min, 25 cycles of 95° C. for 20 s, 80° C. for 5 s, 55° C. for 20 s (0.3° C./s ramp rate), 72° C. for 3 min, followed by a final 5 min extension at 72° C. with 12° C. hold. The PCR product was purified using a Zymo DNA Clean & Concentrator-5 kit (Zymo Research). Fragment size selection with Agencourt AMPure XP beads at a 0.5× volume ratio of beads to PCR product was performed to remove PCR primers. The DNA fragments before (FIG. 23) and after (FIG. 24) size-selection was quantified with a Bioanalyzer 2100 instrument and High Sensitivity DNA chip (Agilent). Barcoded dsDNA fragments had an average length of approximately 1500 bp.

Library Preparation and Next-Generation Sequencing:

The Nextera XT DNA Library Prep Kit (Illumina, catalog no. FC-131-1024) was used to prepare a sequencing library according to the manufacturer protocol. Briefly, 600 pg of the barcoded DNA was used as input to the tagmentation reaction. After neutralization, the transposomes were amplified by 12 cycles of PCR using Nextera PCR Master Mix, 0.2 µM custom primer BD29 (AATGATACGGCGAC-CACCGAGATCTACACGTATGCGACTTCAGTACATC-GTCCC GATGCTCTGCACAGTCGACCGCTGA (SEQ ID NO: 13), containing P5 sequencing adapter) (IDT) and 0.2 µM of Illumina Nextera N706 primer (CAAGCAGAA-GACGGCATACGAGATCATGCCTAGTCTCGTGG-GCTCGG (SEQ ID NO: 14), containing P7 sequencing adapter) (IDT). A final size selection for 300-600 bp DNA fragments was conducted using a BluePippin instrument (Sage Science). The library was quantified by Qubit 3.0 Fluorometer (Invitrogen) and Bioanalyzer 2100 instrument with High Sensitivity DNA chip. The library was sequenced on a MiSeq instrument using a 300-cycle MiSeq Reagent Nano Kit v2 (Illumina, catalog no. MS-103-1001). Custom Read 1 (CAGCGATCCCGAGTCAGATCGATGCCACT-GAGACCTGTGAGTGATGGTTGAGGT AGTGTGGAG) (SEQ ID NO: 15) (IDT) and Index 1 (GTATGCGACTTCAGTACATCGTCCCGATGCTC-TGCACAGTCGACCGCTGA) (SEQ ID NO: 12) (IDT) primers were used according to the manufacturer protocol.

Generating the SiC-Reads Database:

Raw reads from the MiSeq-generated FASTQ files were filtered by quality and grouped by barcode sequence using the Python script barcodeCleanup.py. A given read was discarded if more than 20% of its bases had a Q-score less than Q20, and all reads associated with a barcode containing less than 50 reads were discarded. This step ensured that all barcode groups, representing single cells, contain a sufficient number of high-quality reads. The resulting reads were exported to a table in a SQLite database with fields containing the barcode sequence, barcode group size, a unique read ID number, and read sequence. For the synthetic cell population experiment, the reads were aligned using bowtie2 v2.2.9 with default settings and the SQLite table was updated with relevant alignment information for each read.

Figure 25:
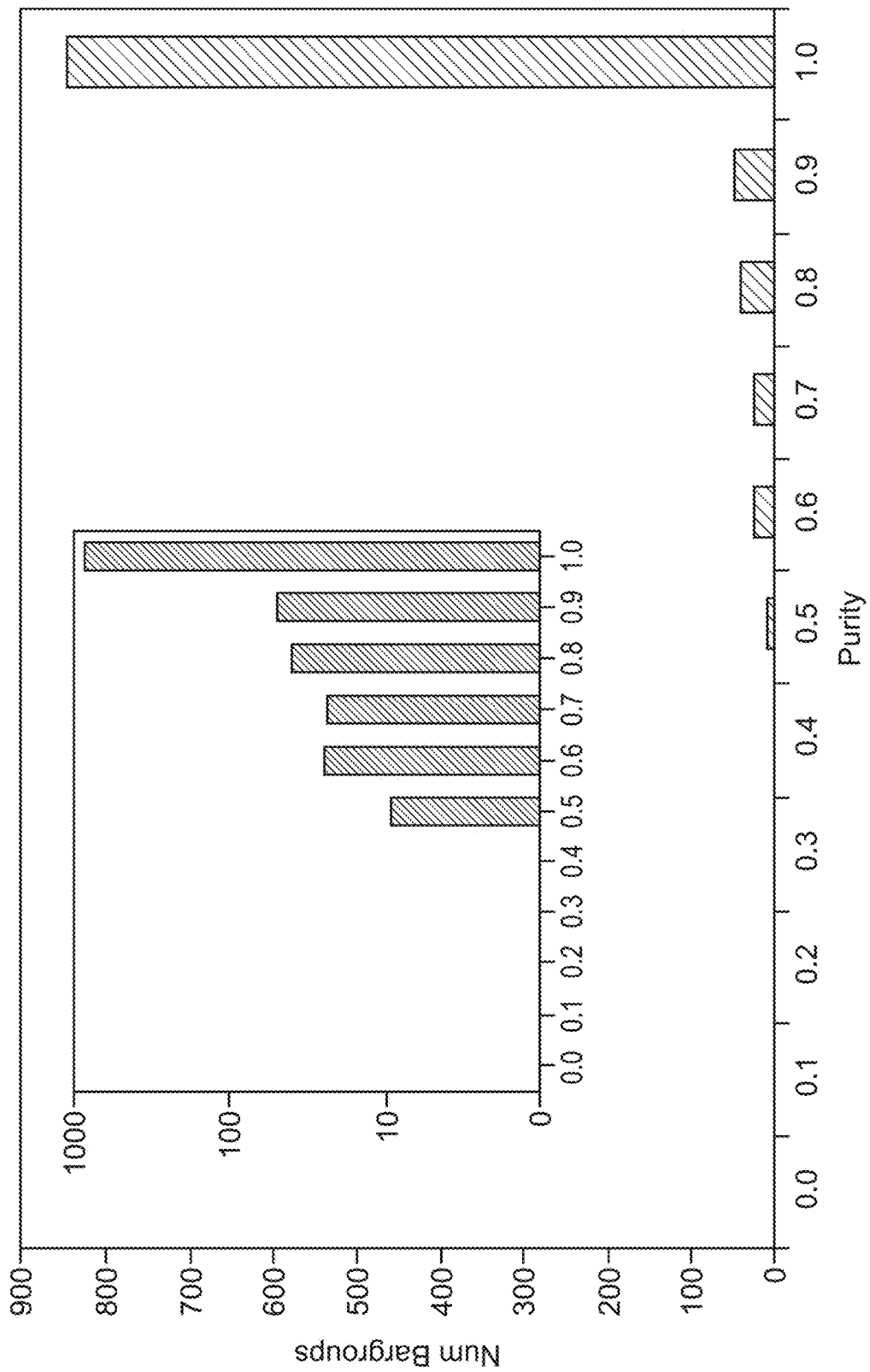
FIG. 25 depicts a histogram displaying the frequencies of barcode group purities for all barcode groups in Example 2. The inset is plotted on a log-scale. The average purity of all barcode groups in the experiment is 0.950 (min. group size of 50 reads).
Figure 26:
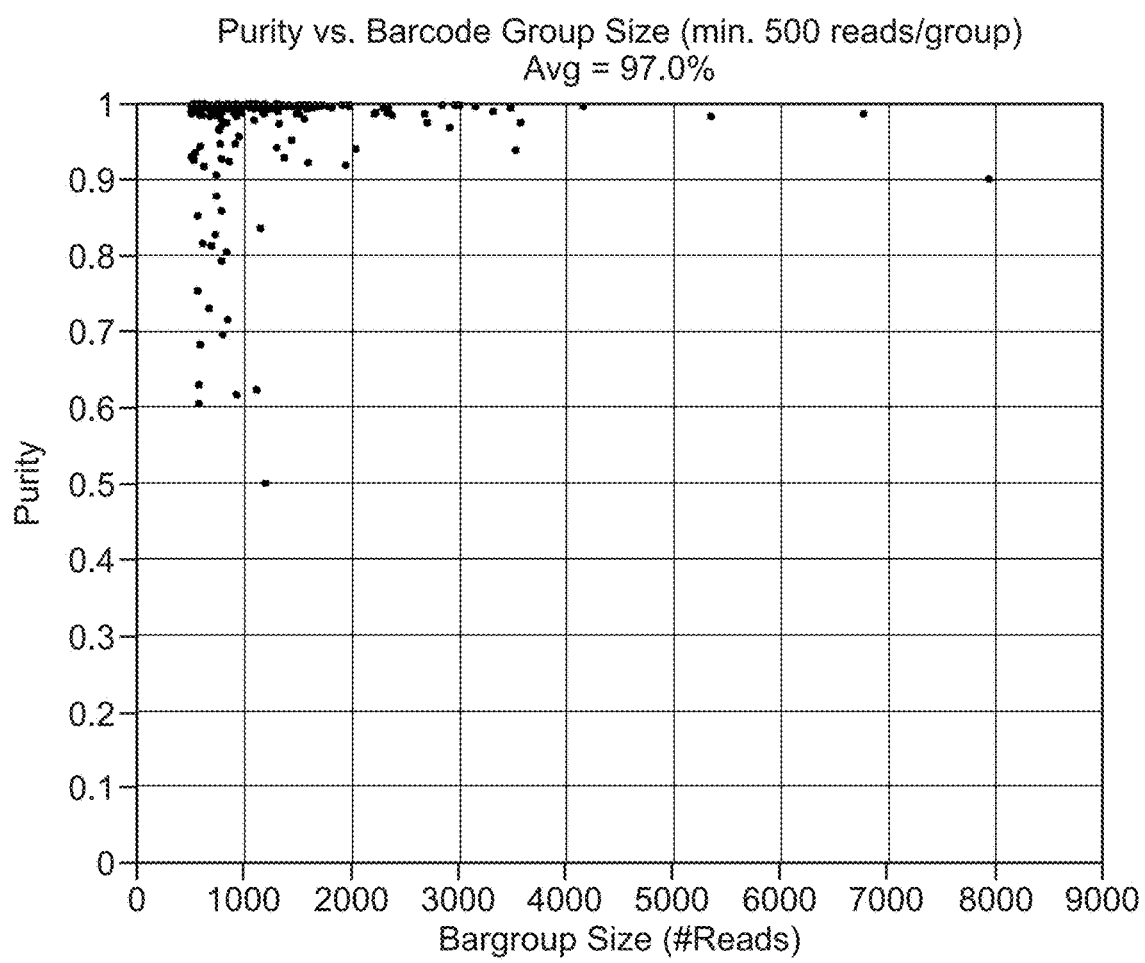
FIG. 26 depicts a scatter plot of barcode group purity vs. the number of reads in a barcode group for Example 2. Each point represents a barcode group. Only barcode groups with a minimum of 500 reads are shown.
Figure 27:
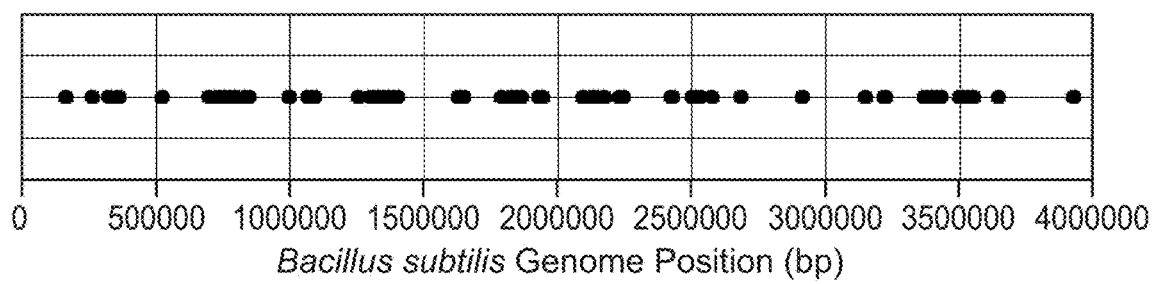
FIG. 27 depicts a genome-wide coverage map for a representative barcode group (species: *Bacillus subtilis*). A dot is placed at all positions along the *Bacillus subtilis* genome where reads from the barcode group align.

Results:

Library sequencing yielded 800,189 reads, 596,357 (74.5%) of which belong to a barcode group containing a minimum of 50 reads. 2,186 barcode groups (min. 50 reads) were obtained. Of reads belonging to these barcode groups, 99.3% aligned to one of the ten reference genomes from the synthetic community. The purity metric for evaluating cross-contamination between barcodes was defined as follows: the purity of a barcode group is defined as the fraction of aligned reads in a barcode group which align to the most common reference genome in that group. A purity of 1.0 means that all reads in a given barcode group align to the same genome. FIG. 25 shows the distribution of purity scores for all barcode groups in the experiment (min. 50 reads per group). The groups are generally highly pure, with an average purity of 0.950. Barcodes with a greater number of reads maintain a high purity (FIG. 26). Reads within individual barcode groups align across the entire reference genomes (FIG. 27), a result of the low-bias amplification characteristics of MALBAC.

What is claimed is:

1. A method of sequencing single cell genomic DNA, the method comprising:
   encapsulating, in a plurality of emulsions, a population of single cells in molten gel droplets to provide a population of molten gel droplets, wherein each molten gel droplet of the population contains zero or one cell;
   solidifying the population of molten gel droplets, within the plurality of emulsions, to provide a population of solidified microgel droplets;
   breaking the plurality of emulsions comprising the solidified microgel droplets to provide a population of solidified microgels;
   subsequent to breaking the plurality of emulsions, exposing the population of solidified microgels in bulk to lysis conditions sufficient to lyse cells contained within the population of solidified microgels;
   purifying genomic DNA from cells contained within the population of solidified microgels in bulk to provide a population of solidified microgels comprising purified genomic DNA;
   encapsulating the population of solidified microgels comprising purified genomic DNA into droplets to provide a population of purified genomic DNA-containing droplets;
   fragmenting the purified genomic DNA within the population of purified genomic DNA-containing droplets to provide a population of fragmented genomic DNA-containing droplets;
   barcoding the fragmented genomic DNA or an amplification product thereof in the population of fragmented genomic DNA-containing droplets to provide a population of barcoded, fragmented genomic DNA-containing droplets;
   purifying barcoded, fragmented genomic DNA from the barcoded, fragmented genomic DNA-containing droplets to provide purified, barcoded, fragmented genomic DNA; and
   sequencing the purified, barcoded, fragmented genomic DNA.

2. The method of claim 1, wherein the barcoding comprises merging the fragmented genomic DNA-containing droplets with barcode-containing droplets.

3. The method of claim 2, wherein one or more of the barcode-containing droplets comprises a unique nucleic acid barcode sequence.

4. The method of claim 1, wherein the molten gel droplets comprise polyethylene glycol (PEG) and polyacrylamide.

5. The method of claim 4, wherein the solidifying comprises one or more of cooling the population of molten gel droplets, chemically crosslinking of the PEG, photo-crosslinking of the PEG or chemical- or photo-crosslinking the polyacrylamide.

6. The method of claim 1, wherein the molten gel droplets comprise alginate and wherein the solidifying comprises adding calcium to the molten gel droplets.

7. The method of claim 1, wherein the solidified microgels comprise pores sized to retain genomic DNA within the solidified microgels.

8. The method of claim 1, wherein the exposing comprises contacting the population of solidified microgels in bulk with a lytic enzyme to lyse cells contained within the population of solidified microgels and wherein the lytic enzyme is selected from zymolyase, lysostaphin, mutanolysin, lysozyme, or a combination thereof.

9. The method of claim 1, wherein the step of purifying genomic DNA from cells contained within the population of solidified microgels comprises contacting the population of solidified microgels with a detergent to solubilize cellular material contained within the population of solidified microgels and wherein the detergent is selected from lithium dodecyl sulfate, sodium dodecyl sulfate, or a combination thereof.

10. The method of claim 1, wherein the step of purifying genomic DNA from cells contained within the population of solidified microgels comprises contacting the population of solidified microgels with a protease to digest cellular proteins contained within the population of solidified microgels and wherein the protease is proteinase K.

11. The method of claim 1, wherein the step of purifying genomic DNA from cells contained within the population of solidified microgels comprises a step of washing the population of solidified microgels, wherein the step of washing the population of solidified microgels comprises contacting the population of solidified microgels with a washing buffer.

12. The method of claim 1, wherein the population of purified genomic DNA-containing droplets comprises complexes comprising a transposase and a transposon.

13. The method of claim 1, wherein the step of fragmenting comprises contacting the purified genomic DNA with a complex comprising a transposase and a transposon and wherein the complex comprises a transposon that comprises an adapter sequence.

14. The method of claim 1, wherein the step of encapsulating a population of single cells in molten gel droplets and the step of barcoding the fragmented genomic DNA or an amplification product thereof are performed using a microfluidic device.

15. The method of claim 1, wherein one or more of the steps of solidifying the population of molten gel droplets to provide a population of solidified microgel droplets;
  breaking the plurality of emulsions comprising the solidified microgel droplets to provide a population of solidified microgels;
  exposing the population of solidified microgels in bulk to lysis conditions sufficient to lyse cells contained within the population of solidified microgels;
  purifying genomic DNA from cells contained within the population of solidified microgels in bulk to provide a population of solidified microgels comprising purified genomic DNA; and
  fragmenting the purified genomic DNA within the population of solidified microgels comprising purified genomic DNA in bulk to provide a population of solidified microgels comprising fragmented genomic DNA,
are not performed using a microfluidic device.

* * * * *

UNITED STATES PATENT AND TRADEMARK OFFICE
CERTIFICATE OF CORRECTION

PATENT NO. : 11,124,830 B2
APPLICATION NO. : 16/849344
DATED : September 21, 2021
INVENTOR(S) : Freeman Lan et al.

Page 1 of 1

It is certified that error appears in the above-identified patent and that said Letters Patent is hereby corrected as shown below:

In the Specification

In Column 18, Line 18, "63 – 50 sec" should read --60 - 30 sec--
In Column 34, Line 65, "Delfia" should read --Delftia--
In Column 42, Line 61, "0.64 pM" should read --0.64 µM--
In Column 43, Line 19, "0.06 U/pL" should read --0.06 U/µL--
In Column 43, Line 60, "0.5 M" should read --0.5 µM-- and In the Claims In Column 56, Claim 15, Line 21, delete "in bulk"

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*